US009599620B2

(12) United States Patent
Benner et al.

(10) Patent No.: US 9,599,620 B2
(45) Date of Patent: Mar. 21, 2017

(54) METHODS AND MONITORING OF TREATMENT WITH A DLL4 ANTAGONIST

(71) Applicant: ONCOMED PHARMACEUTICALS, INC., Redwood City, CA (US)

(72) Inventors: Steven Eugene Benner, Seattle, WA (US); Robert Joseph Stagg, Moraga, CA (US); Jakob Dupont, Hillsborough, CA (US)

(73) Assignee: ONCOMED PHARMACEUTICALS, INC., Redwood City, CA (US)

( * ) Notice: Subject to any disclaimer, the term of this patent is extended or adjusted under 35 U.S.C. 154(b) by 0 days.

(21) Appl. No.: 14/068,910

(22) Filed: Oct. 31, 2013

(65) Prior Publication Data
US 2014/0220001 A1 Aug. 7, 2014

Related U.S. Application Data

(60) Provisional application No. 61/720,768, filed on Oct. 31, 2012.

(51) Int. Cl.
*G01N 33/50* (2006.01)
*A61K 39/395* (2006.01)
*C07K 16/30* (2006.01)
*G01N 33/574* (2006.01)
*G01N 33/68* (2006.01)
*A61K 31/282* (2006.01)
*A61K 31/706* (2006.01)
*G01N 33/74* (2006.01)
*A61K 31/4045* (2006.01)

(52) U.S. Cl.
CPC ..... *G01N 33/57488* (2013.01); *A61K 31/282* (2013.01); *A61K 31/4045* (2013.01); *A61K 31/706* (2013.01); *A61K 39/39558* (2013.01); *C07K 16/30* (2013.01); *G01N 33/6893* (2013.01); *G01N 33/74* (2013.01); *G01N 2333/58* (2013.01); *G01N 2800/32* (2013.01); *G01N 2800/52* (2013.01)

(58) Field of Classification Search
None
See application file for complete search history.

(56) References Cited

U.S. PATENT DOCUMENTS

| 3,773,919 A | 11/1973 | Boswell et al. |
| 4,485,045 A | 11/1984 | Regen |
| 4,544,545 A | 10/1985 | Ryan et al. |
| 4,816,567 A | 3/1989 | Cabilly et al. |
| 5,013,556 A | 5/1991 | Woodle et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,730,977 A | 3/1998 | Ooka et al. |
| 5,731,168 A | 3/1998 | Carter et al. |
| 5,750,373 A | 5/1998 | Garrard et al. |
| 5,840,299 A | 11/1998 | Bendig et al. |
| 6,004,528 A | 12/1999 | Bergstein |
| 6,024,955 A | 2/2000 | Asano et al. |
| 6,121,045 A | 9/2000 | McCarthy et al. |
| 6,262,025 B1 | 7/2001 | Ish-Horowicz et al. |
| 6,342,219 B1 | 1/2002 | Thorpe et al. |
| 6,524,583 B1 | 2/2003 | Thorpe et al. |
| 6,582,959 B2 | 6/2003 | Kim |
| 6,664,098 B1 | 12/2003 | Sakano |
| 6,676,941 B2 | 1/2004 | Thorpe et al. |
| 6,689,744 B2 | 2/2004 | Gao et al. |
| 6,887,468 B1 | 5/2005 | Thorpe et al. |
| 6,984,522 B2 | 1/2006 | Clarke et al. |
| 7,022,499 B2 | 4/2006 | Sakano |
| 7,056,509 B2 | 6/2006 | Thorpe et al. |
| 7,060,269 B1 | 6/2006 | Baca et al. |
| 7,118,890 B2 | 10/2006 | Ish-Horowicz et al. |
| 7,183,076 B2 | 2/2007 | Arathoon et al. |
| 7,227,004 B2 | 6/2007 | Kim |
| 7,354,581 B2 | 4/2008 | Cedarbaum et al. |
| 7,449,182 B2 | 11/2008 | Cedarbaum et al. |
| 7,482,005 B2 | 1/2009 | Kim |
| 7,488,806 B2 | 2/2009 | Papadopoulos et al. |

(Continued)

FOREIGN PATENT DOCUMENTS

| CA | 2789446 A1 | 8/2011 |
| EP | 1 004 669 B1 | 5/1998 |

(Continued)

OTHER PUBLICATIONS

Gradman et al. From left ventricular hypertrophy to congestive heart failure: management of hypertensive heart disease. Prog. Cardiovasc. Dis. 48, 326-341, 2006.*

Yen, W.C., et al., "Anti-DLL4 Has Broad Spectrum Activity in Pancreatic Cancer Dependent on Targeting DLL4-Notch Signaling in Both Tumor and Vascularture Cells," *Clin Cancer Res* 18(19):5374-5386, American Association for Cancer Research, United States (2012).

Han, W., et al., "A soluble form of human Delta-like-1 inhibits differentiation of hemapoietic progenitor cells," *Hematopoiesis*95(5):1616-1625, The American Society of Hematology, United States (2000).

Hicks, C., et al., "A Secreted Deltal-Fc Fusion Protein Functions Both as an Activator and Inhibitor of Notch1 Signaling," *Journal of Neuroscience Research* 68:655-667, Wiley-Liss, Inc., United States (2002).

(Continued)

*Primary Examiner* — Elly-Gerald Stoica
(74) *Attorney, Agent, or Firm* — Sterne, Kessler, Goldstein and Fox P.L.L.C.

(57) ABSTRACT

Methods for treating diseases such as cancer comprising administering a DLL4 antagonist, either alone or in combination with other anti-cancer agents, and monitoring for cardiovascular side effects and/or toxicity.

21 Claims, 3 Drawing Sheets

(56) References Cited

U.S. PATENT DOCUMENTS

| | | |
|---|---|---|
| 7,531,172 B2 | 5/2009 | Stahl et al. |
| 7,534,868 B1 | 5/2009 | Papadopoulos et al. |
| 7,750,124 B2 | 7/2010 | Gurney et al. |
| 7,754,206 B2 | 7/2010 | Clarke et al. |
| 7,758,859 B2 | 7/2010 | Fuh et al. |
| 7,910,098 B2 | 3/2011 | Fuh et al. |
| 7,951,917 B1 | 5/2011 | Arathoon et al. |
| 8,048,418 B2 | 11/2011 | Noguera-Troise et al. |
| 8,216,571 B2 | 7/2012 | Ramachandra et al. |
| 8,858,941 B2 | 10/2014 | Gurney et al. |
| 8,883,145 B2 | 11/2014 | Stagg et al. |
| 9,029,508 B2 | 5/2015 | Ghayur et al. |
| 9,228,020 B2 | 1/2016 | Gurney et al. |
| 9,376,488 B2 | 6/2016 | Gurney et al. |
| 9,376,497 B2 | 6/2016 | Gurney et al. |
| 2002/0028488 A1 | 3/2002 | Singh et al. |
| 2002/0032315 A1 | 3/2002 | Baca et al. |
| 2003/0175877 A1 | 9/2003 | Baker et al. |
| 2003/0180784 A1 | 9/2003 | McCarthy et al. |
| 2004/0123343 A1 | 6/2004 | La Rosa et al. |
| 2004/0133357 A1 | 7/2004 | Zhong et al. |
| 2004/0265307 A1 | 12/2004 | Singh et al. |
| 2004/0265309 A1 | 12/2004 | Kandel et al. |
| 2005/0026831 A1 | 2/2005 | Bodmer et al. |
| 2005/0054036 A1 | 3/2005 | Bates et al. |
| 2005/0059093 A1 | 3/2005 | Bodmer et al. |
| 2005/0079184 A1 | 4/2005 | Hsing-Chang et al. |
| 2005/0089518 A1 | 4/2005 | Clarke et al. |
| 2005/0112121 A1 | 5/2005 | Artavanis-Tsakonas et al. |
| 2005/0137130 A1 | 6/2005 | Bodmer et al. |
| 2005/0261477 A1 | 11/2005 | Champion et al. |
| 2005/0276808 A1 | 12/2005 | Cedarbaum et al. |
| 2005/0281822 A1 | 12/2005 | Cedarbaum et al. |
| 2006/0084588 A1 | 4/2006 | Briend et al. |
| 2006/0122373 A1 | 6/2006 | McCarthy et al. |
| 2006/0134080 A1 | 6/2006 | Lyden et al. |
| 2006/0134121 A1 | 6/2006 | Thurston et al. |
| 2006/0280747 A1 | 12/2006 | Fuh et al. |
| 2007/0004909 A1 | 1/2007 | Johnson et al. |
| 2007/0020267 A1 | 1/2007 | Fuh et al. |
| 2007/0036797 A1 | 2/2007 | Kim et al. |
| 2007/0082846 A1 | 4/2007 | Ish-Horowicz et al. |
| 2007/0098712 A1 | 5/2007 | Arathoon et al. |
| 2007/0141065 A1 | 6/2007 | Fuh et al. |
| 2007/0154391 A1 | 7/2007 | Kim |
| 2007/0178552 A1 | 8/2007 | Arathoon et al. |
| 2007/0190573 A1 | 8/2007 | Hess et al. |
| 2007/0190647 A1 | 8/2007 | Clarke et al. |
| 2007/0196374 A1 | 8/2007 | Baca et al. |
| 2007/0202102 A1 | 8/2007 | Bizzini et al. |
| 2007/0212354 A1 | 9/2007 | Yung et al. |
| 2007/0213266 A1 | 9/2007 | Gill et al. |
| 2007/0231325 A1 | 10/2007 | Clarke et al. |
| 2007/0287170 A1 | 12/2007 | Davis et al. |
| 2008/0014196 A1 | 1/2008 | Yan |
| 2008/0063635 A1 | 3/2008 | Takahashi et al. |
| 2008/0069820 A1 | 3/2008 | Fuh et al. |
| 2008/0107648 A1 | 5/2008 | Noguera et al. |
| 2008/0175847 A1 | 7/2008 | Yan et al. |
| 2008/0181893 A1 | 7/2008 | Lobov et al. |
| 2008/0181899 A1 | 7/2008 | Papadopoulos et al. |
| 2008/0187532 A1* | 8/2008 | Gurney et al. ............. 424/133.1 |
| 2008/0220495 A1 | 9/2008 | McCarthy et al. |
| 2009/0004205 A1 | 1/2009 | Clarke et al. |
| 2009/0023591 A1* | 1/2009 | Spanuth ............. 506/7 |
| 2009/0035308 A1 | 2/2009 | Gill et al. |
| 2009/0221549 A1 | 9/2009 | Gerber et al. |
| 2009/0246199 A1 | 10/2009 | Noguera-Troise et al. |
| 2009/0286956 A1 | 11/2009 | McCarthy et al. |
| 2010/0015133 A1 | 1/2010 | Igawa et al. |
| 2010/0076178 A1 | 3/2010 | Ghayur et al. |
| 2010/0086544 A1 | 4/2010 | Mass et al. |
| 2010/0129356 A1 | 5/2010 | Yan |
| 2010/0150940 A1 | 6/2010 | Adam et al. |
| 2010/0215779 A1 | 8/2010 | Currie et al. |
| 2010/0221250 A1 | 9/2010 | Kim et al. |
| 2010/0260668 A1 | 10/2010 | Ghayur et al. |
| 2010/0266589 A1 | 10/2010 | Hedrick et al. |
| 2010/0272733 A1 | 10/2010 | Bates et al. |
| 2010/0286374 A1 | 11/2010 | Kannan et al. |
| 2010/0316637 A1 | 12/2010 | Gurney et al. |
| 2011/0052575 A1 | 3/2011 | Baca et al. |
| 2011/0052576 A1 | 3/2011 | Ferrara et al. |
| 2011/0076279 A1 | 3/2011 | Ramachandra et al. |
| 2011/0081342 A1 | 4/2011 | Baca et al. |
| 2011/0091372 A1 | 4/2011 | Ghayur et al. |
| 2011/0113865 A1 | 5/2011 | Hess et al. |
| 2011/0117079 A1 | 5/2011 | Benatuil et al. |
| 2011/0123532 A1 | 5/2011 | Gurney et al. |
| 2011/0165162 A1 | 7/2011 | Hoey et al. |
| 2011/0172398 A1 | 7/2011 | Borges et al. |
| 2011/0217237 A1 | 9/2011 | Chen et al. |
| 2012/0116057 A1 | 5/2012 | Kannan et al. |
| 2012/0245151 A1 | 9/2012 | Gavai et al. |
| 2012/0288496 A1 | 11/2012 | Gurney et al. |
| 2013/0131076 A1 | 5/2013 | Fernandez et al. |
| 2013/0164295 A1 | 6/2013 | Gurney et al. |
| 2013/0253172 A1 | 9/2013 | Gurney et al. |
| 2013/0266569 A1 | 10/2013 | Gurney et al. |
| 2013/0309250 A1 | 11/2013 | Cogswell et al. |
| 2013/0323265 A1 | 12/2013 | Stagg et al. |
| 2014/0017244 A1 | 1/2014 | Duerr et al. |
| 2014/0206853 A1 | 7/2014 | Foltz et al. |
| 2014/0227252 A1 | 8/2014 | Benner et al. |
| 2015/0098949 A1 | 4/2015 | Gurney et al. |
| 2015/0118232 A1 | 4/2015 | Stagg et al. |

FOREIGN PATENT DOCUMENTS

| | | |
|---|---|---|
| EP | 0 861 894 A1 | 9/1998 |
| EP | 0 662 827 B1 | 4/2002 |
| EP | 0662827 B1 | 4/2002 |
| EP | 1 179 541 B1 | 6/2004 |
| EP | 0 979 281 B1 | 7/2005 |
| EP | 1615036 A1 | 1/2006 |
| EP | 0 972 041 B1 | 10/2006 |
| EP | 1 810 979 A1 | 7/2007 |
| EP | 1 870 459 A1 | 12/2007 |
| EP | 2 066 694 | 6/2009 |
| EP | 2 235 064 | 7/2009 |
| EP | 2 483 314 | 4/2011 |
| EP | 2 424 567 | 3/2012 |
| GB | 2 449 354 A | 11/2008 |
| JP | 2005-511754 A | 4/2005 |
| WO | WO 92/19734 | 11/1992 |
| WO | WO 94/07474 | 4/1994 |
| WO | WO 97/01571 A1 | 1/1997 |
| WO | WO 98/45434 A1 | 10/1998 |
| WO | WO-9845331 A2 | 10/1998 |
| WO | WO 98/51799 | 11/1998 |
| WO | WO 98/57621 A1 | 12/1998 |
| WO | WO 00/06726 A2 | 2/2000 |
| WO | WO 01/40466 A2 | 6/2001 |
| WO | WO 02/12447 | 2/2002 |
| WO | WO 03/041735 A2 | 5/2003 |
| WO | WO 03/050502 A2 | 6/2003 |
| WO | WO 2004/110490 A2 | 12/2004 |
| WO | WO 2006/027693 A2 | 3/2006 |
| WO | WO 2006/028936 A2 | 3/2006 |
| WO | WO 2006/033386 A1 | 3/2006 |
| WO | WO 2006/052128 A1 | 5/2006 |
| WO | WO 2006/106905 A1 | 10/2006 |
| WO | WO 2007/028110 A2 | 3/2007 |
| WO | WO 2007/070671 A2 | 6/2007 |
| WO | WO 2007/143689 A2 | 12/2007 |
| WO | WO 2007/145840 A2 | 12/2007 |
| WO | WO 2007/147901 A1 | 12/2007 |
| WO | WO 2008/042236 A2 | 4/2008 |
| WO | WO 2008/060705 | 5/2008 |
| WO | WO 2008/070042 A2 | 6/2008 |
| WO | WO 2008/076379 A2 | 6/2008 |
| WO | WO 2008/091222 A1 | 7/2008 |
| WO | WO 2008/793326 A2 | 7/2008 |
| WO | WO 2008/139202 A1 | 11/2008 |

(56) References Cited

FOREIGN PATENT DOCUMENTS

| WO | WO 2009/075565 A1 | 6/2009 | | |
|---|---|---|---|---|
| WO | WO 2009/080251 A1 | 7/2009 | | |
| WO | WO 2009/085209 A2 | 7/2009 | | |
| WO | WO 2009/089004 A1 | 7/2009 | | |
| WO | WO-2010010153 A1 | 1/2010 | | |
| WO | WO 2010/054010 A1 | 5/2010 | | |
| WO | WO 2010/124009 A2 | 10/2010 | | |
| WO | WO-2010124009 A2 | 10/2010 | | |
| WO | WO 2010/129304 A2 | 11/2010 | | |
| WO | WO 2011/039370 A1 | 4/2011 | | |
| WO | WO 2011/047442 A1 | 4/2011 | | |
| WO | WO2011047383 | * | 4/2011 | ........... A61K 39/395 |
| WO | WO-2011068840 A1 | 6/2011 | | |
| WO | WO-2011100566 A2 | 8/2011 | | |
| WO | WO-2011109298 A2 | 9/2011 | | |
| WO | WO 2012/068098 A1 | 5/2012 | | |
| WO | WO 2013/044215 A1 | 3/2013 | | |

OTHER PUBLICATIONS

Jimeno, A., et al., "Phase 1 study of REGN421 (R)/SAR153192, a fully-human delta-like ligand 4 (DLL4) monoclonal antibody (mAb), in patients with advanced solid tumors," ASC Univeristy 2013 ASCO Annual Meeting accessed at http://meetinglibrary.asco.org/content/113836-132, 2 pages.

Dupont, J., "Anti-Angiogenic Agents and Cardiovascular Effects: Implications for Clinical Development in Cancer," presentation given in Barcelona, Spain on Nov. 4, 2011, 16 pages.

OncoMed Pharmaceuticals Inc. SEC Form S-1 filed on May 11, 2012, 1032 pages.

OncoMed Pharmaceuticals Inc. SEC Form S-1/A for filed on Jun. 15, 2012, 204 pages.

Unknown Author "Tumor angiogenesis suppression therapy targeting the Notch signaling pathway," *Suizo (Pancreas)* 21(3):249, Japan (2006).

Al-Hajj, M., et al., "Prospective identification of tumorigenic breast cancer cells," *Proc. Nat. Acad. Sci.* 100(7):3983-3988, National Academy of Sciences, Washington, DC, USA (Apr. 2003).

Allenspach, E.J. et al., "Notch signaling in cancer," *Cancer Biol. Ther.* 1(5):466-76, Landes Bioscience, United States (2002).

Artavanis-Tsakonas, S. et al., "Notch signaling: cell fate control and signal integration in development," *Science* 284(5415):770-6, American Association for the Advancement of Science, United States (1999).

Axelson, H., "Notch signaling and cancer: emerging complexity," *Semin. Cancer Biol.* 14(5):317-9, Academic Press, England (2004).

Beachy, P., et al., "Tissue repair and stem cell renewal in carcinogenesis," *Nature* 432:324-331, Nature Publishing Group, New York, NY, U.S.A. (2004).

Bellavia, D., et al., "Constitutive activation of NF-κB and T-cell leukemia/lymphoma in Notch3 transgenic mice," *EMBO J.* 19:3337-3348, Oxford University Press, New York, NY USA (2000).

Benvenuti, et al., "Oncogenic Activation of the RAS/RAF Signaling Pathway Impairsthe Response of Metastatic Colorectal Cancers to Anti-Epidermal Growth Factor Receptor Antibody Therapies," *Cancer Res.* 67(6):2643-2648, American Association for Cancer Research, USA (Mar. 2007).

Besseyrias, V., et al., "Hierarchy of Notch-Delta interactions promoting T cell lineage commitment and maturation," *J. Exp. Med.* 204:331-343, The Rockefeller University Press (2007).

Bonnet, D. and Dick, J.E., "Human acute myeloid leukemia is organized as a hierarachy that originates from a primitive hematopoietic cell," *Nat. Med.* 3:730-737, Nature Publishing Group, New York, NY, U.S.A. (1997).

Bray, S.J., "Notch signalling: a simple pathway becomes complex," *Nature* 7:678-689, Nature Publishing Group (2006).

Brennan, K. and Brown, A.M.C., "Is there a role for Notch signalling in human breast cancer?" *Breast Cancer Res.* 5:69-75, BioMed Central Ltd, London, UK (2003).

Callahan, R. and Raafat, A., "Notch signaling in mammary gland tumorigenesis," *J Mammary Gland Biol Neoplasia* 6(1):23-36, Kluwer Academic/Plenum Publishers, United States (2001).

Carter, P., "Improving the efficacy of antibody-based cancer therapies," *Nat. Rev. Cancer.* 1(2): 118-29, Nature Pub. Group, England (Nov. 2001).

Chau, I. and Cunningham, D., "Treatment in advanced colorectal cancer: what, when and how?," *British Journal of Cancer* 100(11):1704-1719, Cancer Research UK, England (May 2009).

Clarke, M.F., et al., "Cancer Stem Cells-Perspectives on Current Status and Future Directions: AACR Workshop on Cancer Stem Cells," *Cancer Res.* 66:9339-9344, American Association for Cancer Research (2006).

Dalerba, P., et al., "Phenotypic characterization of human colorectal cancer stem cells," *Proc. Nat. Acad. Sci.* 104(24):9913-10294, National Academy of Sciences, Washington, DC, USA (Jun. 2007).

Dando, J. et al., "Notch/Delta4 Interaction in Human Embryonic Liver $CD34^+CD38\_$ Cells: Positive Influence on BGU-E Production in LTC-IC Potential Maintenance," *Stem Cells* 23:550-560 (2005).

Dontu, G., et al., "Role of Notch signaling in cell-fate determination of human mammary stem/progenitor cells," *Breast Cancer Res.* 6:R605-R615, BioMed Central Ltd. (2004).

Dorsch, M., et al., "Ectopic expression of Delta4 impairs hematopoietic development and leads to lymphoproliferative disease," *Blood* 100:2046-2055, American Society of Hematology (2002).

Duarte, A., et al., Dosage-sensitive requirement for mouse Dll4 in artery development, *Genes & Dev.* 18:2474-2478, Cold Spring Harbor Laboratory Press (2004).

Ellisen, L.W., et al., "TAN-1, the Human Homolog of the *Drosophila* Notch Gene, Is Broken by Chromosomal Translocations in T Lymphoblastic Neoplasms," *Cell* 66:649-661, Elsevier Inc., Amsterdam, The Netherlands (1991).

Engin, F., et al., "Dimorphic effects of Notch signaling in bone homeostasis," *Nature Medicine* 14:299-305, Nature Publishing Group (2007).

English language translation of "Tumor angiogenesis suppression therapy targeting the Notch signaling pathway," *Suizo (Pancreas)* 21(3):249, Japan (2006).

English language translation of Oishi, H., et al., "Novel therapeutic strategy for pancreatic cancer targeting Notch signaling pathway," *Proceedings of the Japanese Cancer Association* 65:311-312, Japan (2006).

Farnie, G. and Clarke, R.B., "Mammary Stem Cells and Breast Cancer—Role of Notch Signalling," *Stem Cell Rev.* 3:169-175, Humana Press (2007).

Farnie, G., et al., "Novel Cell Culture Technique for Primary Ductal Carcinoma In Situ: Role of Notch and Epidermal Growth Factor Receptor Signaling Pathways ," *JNCI* 99:616-627, Oxford University Press (2007).

Fleming, R.J. et al., "The Notch receptor and its ligands," *Trends in Cell Biol.* 7:437-441 (1997).

Fre, S. et al, "Notch signals control the fate of immature progenitor cells in the intestine," *Nature* 435(7044):964-8, Nature Publishing Group, England (2005).

Fung, E., et al., "Delta-like 4 induces notch signaling in macrophages: implications for inflammation," *Circulation* 115:2948-2956, Lippincott Williams & Wilkins, Baltimore, MD U.S.A. (2007).

Gale, N.W., et al., "Haploinsufficiency of delta-like 4 ligand results in embryonic lethality due to major defects in arterial and vascular development," *PNAS* 101:15949-15954, National Academy of Sciences (2004).

Gallahan, D. et al., "A New Common Integration Region (*int*-3) for Mouse Mammary Tumor Virus on Mouse Chromosome 17," *J. of Virol.* 61(1):218-220, American Society for Microbiology, USA (Jan. 1987).

Gallahan, D. et al., "Expression of a Truncated *Int3* Gene in Developing Secretory Mammary Epithelium Specifically Retards

(56) References Cited

OTHER PUBLICATIONS

Lobular Differentiation Resulting in Tumorigenesis," *Cancer Research* 56:1775-1785, American Association for Cancer Research, USA (Apr. 1996).
Garber, K., "Notch Emerges as New Cancer Drug Target," *JNCI* 99:1284-1285, Oxford University Press (2007).
Gridley, T., "Notch signaling in vascular development and physiology," *Development* 134:2709-2718, The Company of Biologists (2007).
Gurney, A. and Hoey, T., "Anti-DLL4, a cancer therapeutic with multiple mechanisms of action," *Vasc. Cell* 3:18, BioMed Central, England (2011), 4 pages.
Hainaud, P., et al., "The Role of the Vascular Endothelial Growth Factor-Delta-like 4 ligand/Notch4-Ephrin B2 Cascade in Tumor Vessel Remodeling and Endothelial Cell Functions," *Cancer Res.* 66:8501-8510 (Sep. 2006).
Hallahan, A., et al., "The SmoA1 Mouse Model Reveals That Notch Signaling is Critical for the Growth and Survival of Sonic Hedgehog-Induced Medulloblastomas," *Cancer Research* 64(21):7794-7800, American Society for Cancer Research, USA (Nov. 2004).
Han, W. et al., "A soluble form of human Delta-like-1 inhibits differentiation of hematopoietic progenitor cells," *Blood* 95(5):1616-25, American Society of Hematology, United States (2000).
Harper, J.A. et al., "Notch signaling in development and disease," *Clin Genet.* 64(6):461-72, Munksgaard, Denmark (2003).
Harrington, L.S., et al., "Regulation of multiple angiogenic pathways by Dll4 and Notch in human umbilical vein endothelial cells," *Microvasc. Res.* 75:144-154, Elsevier, Inc. (2008).
Hellström, M., et al., "Dll4 signalling through Notch1 regulates formation of tip cells during angiogenesis," *Nature* 445:776-780, Nature Publishing Group (2007).
Henning, K., et al., "mNotch1 signaling and erythropoietin cooperate in erythroid differentiation of multipotent progenitor cells and upregulate β-*globin*," *Exp. Hematol.* 35:1321-1332, Elsevier, Inc. (2007).
Hoey, T., et al., "DLL4 Blockade Inhibits Tumor Growth and Reduces Tumor Initiating Cell Frequency," *Cell Stem Cell* 5(2), 168-177, 2009.
Hofmann, J.J. and Iruela-Arispe, M.L., "Notch Signaling in Blood Vessels: Who Is Talking to Whom About What?," *Circ. Res.* 100:1556-1568 American Heart Association, Inc. (2007).
Hope, K.J., et al., "Acute myeloid leukemia originates from a hierarchy of leukemic stem cell classes that differ in self-renewal capacity," *Nat. Immunol.* 5:738-43, Nature Publishing Group, New York, NY, U.S.A. (2004).
Hopfer, O. et al., "The Notch pathway in ovarian carcinomas and adenomas," *Br J Cancer* 93(6):709-18, Nature Publishing Group on behalf of Cancer Research UK, England (2005).
International Search Report for International Patent Application No. PCT/US11/60773, International Searching Authority, Alexandria, Virginia, United States, mailed on Mar. 26, 2012.
International Search Report with Written Opinion for International Application No. PCT/US2010/58511, International Searching Authority, United States, mailed Mar. 3, 2011.
Ishiko, E., et al., "Notch Signals Inhibit the Development of Erythroid/Megakaryocytic Cells by Suppressing GATA-1 Activity through Induction of HES1," *J. Biol. Chem.* 280:4929-4939, The American Society for Biochemistry and Molecular Biology, Inc. (2005).
Iso, T., et al., "Notch Signaling in Vascular Development," *Arterioscler. Thromb. Vasc. Biol.* 23:543-553, Lippincott Williams & Wilkins, Philadelphia, PA, U.S.A. (2003).
Janeway, C. et al., "Immunobiology: The Immune System in Health and Disease," Appendix L, pp. 579-581, Current Biology Publications, 4th Edition (1999).
Jarriault, S., et al., "Signalling downstream of activated mammalian Notch," *Nature* 377:355-358, Nature Publishing Group (1995).

Jeffries, S. and Capobianco, A.J., "Neoplastic transformation by Notch requires nuclear localization," *Mol Cell Biol.* 20(11):3928-41, American Society for Microbiology, United States (2000).
Jhappan, C., et al., "Expression of an activated *Notch*-related *int*-3 transgene interferes with cell differentiation and induces neoplastic and salviary glands," *Genes & Dev.* 6:345-355, Cold Spring Harbor Laboratory Press, Woodbury NY, USA (1992).
Kopper, L. and Hajdú, M., "Tumor Stem Cells," *Pathol. Oncol. Res.* 10:69-73, Arányi Lajos Foundation, Budapest, Hungary (2004).
Krebs, L.T., et al., "Haploinsufficient lethality and formation of arteriovenous malformations in Notch pathway mutants," *Genes Dev.* 18:2469-2473, Cold Spring Harbor Laboratory Press (2004).
Krebs, L.T., et al., "Notch signaling is essential for vascular morphogenesis in mice," *Genes & Dev.* 14:1343-1352, Cold Spring Harbor Laboratory Press, Woodbury NY, U.S.A. (2000).
Lapidot, T., et al., "A cell initiating human acute myeloid leukaemia after transplantation into SCID mice," *Nature* 367:645-648, Nature Publishing Group, New York, NY, USA (1994).
Lauret, E. et al., "Membrane-bound Delta-4 Notch ligand reduces the proliferative activity of primitive human hematopoietic $CD34^+CD38^{low}$ cells while maintaining their LTC-IC potential," *Leukemia* 18:788-797 (Feb. 2006).
Leethanakul, C., et al., "Distinct pattern of expression of differentiation and growth-related genes in squamous cell carcinomas of the head and neck revealed by the use of laser capture microdissection and cDNA arrays," *Oncogene* 19:3220-3224, Nature Publishing Group, New York, NY, USA (2000).
Leong, K. G. and Karsan, A., "Recent insights into the role of Notch signaling in tumorigenesis," *Blood* 107(6):2223-2233, The American Society of Hematology, USA (Mar. 2006).
Li, J.-L. and Harris, A.L., "Notch signaling from tumor cells: A new mechanism of angiogenesis," *Cancer Cell* 8:1-3, Cell Press (2005).
Limbourg, A., et al., Notch Ligand Delta-Like 1 Is Essential for Postnatal Arteriogenesis, *Circ. Res* 100:363-371, American Heart Association, Inc. (2007).
Liu, S., et al., "Mammary stem cells, self-renewal pathways, and carcinogenesis," *Breast Cancer Research* 7:86-95, BioMed Central Ltd. (2005).
Liu, Z.-J., et al., "Regulation of *Notch1* and *Dll4* by Vascular Endothelial Growth Factor in Arterial Endothelial Cells: Implications for Modulating Arteriogenesis and Angiogenesis," *Molecular and Cellular Biology* 23:14-25, American Society for Microbiology (2003).
Liu, Z-J., et al., "Inhibition of endothelial cell proliferation by Notch1 signaling is mediated by repressing MAPK and P14K/Akt pathways and requires MAML1," *FASEB J.* 20:E201-E210 (May 2006).
Lobov, I.B., et al., "Delta-like ligand 4 (Dll4) is induced by VEGF as a negative regulator of angiogenic sprouting," *PNAS* 104:3219-3224, National Academy of Sciences (2007).
Mailhos, C., et al., "Delta4, an endothelial specific Notch ligand expressed at sites of physiological and tumor angiogenesis," *Differentiation* 69:135-144, Blackwell Wissenschafts-Verlag (2001).
Mazella, J., et al., "Expression of Delta-Like Protein 4 in the Human Endometrium," *Endocrinology* 149:15-19, The Endocrine Society (2008).
Miele, L. and Osborne, B., "Arbiter of Differentiation and Death: Notch Signaling Meets Apoptosis," *Journal of Cellular Physiology* 181:393-409, Wiley-Liss, Inc. (1999).
Miele, L., "Notch Signaling," *Clin. Cancer Res.* 12:1074-1077, American Association for Cancer Research (2006).
Milano, J., et al., Modulation of Notch Processing by γ-Secretase Inhibitors Causes Intestinal Goblet Cell Metaplasia and Induction of Genes Known to Specify Gut Secretory Lineage Differentiation, *Toxicol Sci* 82:341-358, Society of Toxicology (2004).
Morrison, S.J. et al., "Transient Notch activation initiates an irreversible switch from neurogenesis to gliogenesis by neural crest stem cells," *Cell* 101(5):499-510, Cell Press, United States (2000).
Morrison, S.J., et al., "Hematopoietic stem cells: challenges to expectations," *Curr. Op. Immun.* 9:216-221, Current Biology, Ltd., England (1997).
Morrison, S.J., et al., "Regulatory Mechanisms in Stem Cell Biology," *Cell* 88:287-298, Cell Press, St. Louis, MO, U.S.A. (1997).

(56) References Cited

OTHER PUBLICATIONS

Morrison, S.J., et al., "The Biology of Hematopoietic Stem Cells," *Annu. Rev. Cell Dev. Biol.* 11:35-71, Annual Reviews, USA (1995).
Nam, Y. et al., "Notch signaling as a therapeutic target," *Curr Opin Chem Biol.* 6(4):501-9, Elsevier, England (2002).
NCT00744562, "A Phase 1 Dose Escalation Study of OMP-21M18 in Subjects With Solid Tumors," ClinicalTrials.gov archive, accessed at http://clinicaltrials.gov/archive/NCT01189968/2010_10_28, accessed on Feb. 2, 2012, 4 pages.
NCT01189968, "A Phase 1b Study of Carboplatin and Permetrexed Plus OMP-21M18 as 1st-line Treatment in Subject With Non-Squamous Non-Small Cell Lung Cancer," ClinicalTrials.gov archive, accessed at http://clinicaltrials.gov/archive/NCT01189968/2010_10_28, accessed on Feb. 7, 2012, 4 pages.
Noguera, I., et al., "Delta-like ligand 4 (Dll4) is critical for tumor growth and angiogenesis" *Proceedings of the Annual Meeting of the American Association for Cancer Research* 47: 1342, American Association for Cancer Research, United States (Apr. 2006).
Noguera, I., et al., "Expression of Delta-like 4 (DII4) ligand in mouse tumor models" *Proceedings of the Annual Meeting of the American Association for Cancer Research* 46(Suppl. S): 1104, American Association for Cancer Research, United States (Apr. 2005).
Noguera-Troise, I., et al., "Blockade of Dll4 inhibits tumour growth by promoting non-productive angiogenesis," *Nature* 444:1032-1037, Nature Publishing Group, New York, NY, USA (2006).
International Search Report of the International Searching Authority for International application No. PCT/US2007/020889, mailed Apr. 9, 2008, United States Patent and Trademark Office, United States.
Written Opinion of the International Searching Authority for International application No. PCT/US2007/020889, mailed Apr. 9, 2008, United States Patent and Trademark Office, United States.
Oishi, H., et al., "Novel therapeutic strategy for pancreatic cancer targeting Notch signaling pathway," *Proceedings of the Japanese Cancer Association* 65:311-312, Japan (2006).
Parks, A.L., et al., "Structure-Function Analysis of Delta Trafficking, Receptor Binding and Signaling in *Drosophila*," *Genetics* 174:1947-1961, The Genetics Society of America (2006).
Parr, C., et al., "The possible correlation of Notch-1 and Notch-2 with clinical outcome and tumour clinicopathological parameters in human breast cancer," *Int J. Mol. Med.* 14:779-786, Spandidos Publications Ltd., Athens, Greece (2004).
Patel, N.S., et al., "Up-regulation of Delta-like 4 Ligand in Human Tumor Vasculature and the Role of Basal Expression in Endothelial Cell Function," *Cancer Res.* 65:8690-8697, The American Association for Cancer Research (2005).
Paul, William E., *Fundamental Immunology*, 3rd Edition, Chapter 8, p. 242, Raven Press, New York, United States, (1993).
Pear, W.S. and Aster, J.C., "T cell acute lymphoblastic leukemia/lymphoma: a human cancer commonly associated with aberrant NOTCH1 signaling," *Curr. Opin. Hematol.* 11:426-433, Lippincott Williams & Wilkins, Philadelphia, PA, USA (2004).
Pear, W.S., et al., "Exclusive Development of T cell Neoplasms in Mice Transplanted with Bone Marrow Expressing Activated *Notch* Alleles," *J. Exp. Med.* 183:2283-2291, the Rockefeller University Press, New York, NY, USA (1996).
Phng, L.-K., et al., "Nrarp Coordinates Endothelial Notch and Wnt Signaling to Control Vessel Density in Angiogenesis," *Dev. Cell* 16:70-82, Elsevier, Inc. (2009).
Politi, K., et al., "Notch in mammary gland development and breast cancer," *Semin. Cancer Biol.* 14:341-347, Elsevier Inc., Amsterdam, The Netherlands (2004).
Purow, B.W., et al., "Expression of Notch-1 and its Ligands, Delta-Like-1 and Jagged-1, is Critical for Glioma Cell Survival and Proliferation," *Cancer Res.* 65:2353-2363, BioMed Central Ltd, London, UK (2005).
Rae, F.K., et al., "Novel Association of a Diverse Range of Genes with Renal Cell Carcinoma as Identified by Differential Display," *Int. J. Cancer* 88:726-732, Wiley-Liss, Inc., Massachusetts, U.S.A (2000).

Rao, P.K., et al., "Isolation and Characterization of the Notch Ligand Delta4," *Cell Res.* 260:379-386, Elsevier, Inc. (2008).
Dixit, R., "Cardiovascular Safety of Biologics: Challenges and Opportunities," Medimmune, Safety Pharmacology Society, Annular Meeting Speakers Presentations (Oct. 2, 2012).
Reya, T., et al., "Stem cells, cancer, and cancer stem cells," *Nature* 414:105-111, Nature Publishing Company (2001).
Ridgeway., J., et al., "Inhibition of Dll4 signaling inhibits tumour growth by deregulating angiogenesis," *Nature* 444:1083-1087, Nature Publishing Group, New York, NY, U.S.A. (2006).
Robey, E., et al., "An Activated Form of Notch Influences the Choice between CD4 and CD8 T Cell Lineages," *Cell* 87:483-492, Elsevier Inc., Amsterdam, The Netherlands (1996).
Sainson, R.C.A. and Harris, A.L., "Anti-Dll4 therapy: can we block tumour growth by increasing angiogenesis?," *Trends Mol. Med.* 13:389-395, Elsevier, Inc. (2007).
Scehnet, J.S., et al., "Inhibition of DII4-mediated signaling induces proliferation of immature vessels and results in poor tissue perfusion," *Blood* 109:4753-4760, American Society of Hematology (2007).
Seina, A., et al., "Biomarkers Predicting Clinical Outcome of Epidermal Growth Factor Receptor-Targeted Therapy in Metastatic Colorectal Cancer," *JNCI* 101(19):1308-1324, Oxford University Press, England (Oct. 2009).
Shawber, C.J., et al., "Notch Signaling in Primary Endothelial Cells," *Ann. N.Y. Acad. Sci.* 995:162-170, New York Academy of Sciences (2003).
Shutter, J.R., et al., "*Dll4*, a novel Notch ligand expressed in arterial endothelium," *Genes & Dev.* 14:1313-1318, Cold Spring Harbor Laboratory Press, Woodbury NY, U.S.A. (2000).
Siekmann, A.F. and Lawson, N.D., "Notch signalling limits angiogenic cell behaviour in developing zebrafish arteries," *Nature* 445:781-784, Nature Publishing Group (2007).
Smith et al., "A First-in-Human, Phase 1 Trial of the Anti-DLL4 Antibody (OMP-21M18) Tageting Cancer Stem CellS (CSCs) in Patients with Advanced Solid Tumors," http://www.oncomed.com/news/pr/study1posterfinalNov10.pdf, accessed Feb. 2, 2012, 1 page.
Smith, G.H., et al., "Constitutive Expression of a Truncated *INT3* Gene in Mouse Mammary Epithelium Impairs Differentiation and Functional Development," *Cell Growth Differ.* 6:563-577, the American Association for Cancer Research, Philadelphia, PA, USA (1995).
Soriano, J.V., et al., "Expression of an Activated Notch4(int-3) Oncoprotein Disrupts Morphogenesis and Induces an Invasive Phenotype in Mammary Epithelial Cells In Vitro," *Int. J. Cancer* 86:652-659, Wiley-Liss, Inc., Massachusetts, USA (2000).
Sugimoto, A. et al., "Delta-4 Notch ligand promotes erythroid differentiation of human umbilical cord blood CD34+ cells," *Exp. Hematol.* 34:424-432 (Apr. 2006).
Supplementary European Search Report issued in the corresponding European Patent Application No. 07 83 8966, European Patent Office, Munich, Germany, mailed on Apr. 6, 2010.
Suzuki, T., et al., "Imbalanced expression of *TAN-1* and human *Notch4* in endometrial cancers," *Int. J. Oncol.* 17:1131-1139, Spandidos Publications Ltd., Athens, Greece (2000).
Tannok, I. and Hill, R., "The Basic Science of Oncology," pp. 357-358, New York: McGraw-Hill (1998).
Tax, F.E., et al., "Sequence of *C. elegans lag-*2 reveals a cell-signalling domain shared with *Delta* and *Serrate of Drosophila*," *Nature* 368:150-154, Nature Publishing Company (1994).
Thélu, J. et al., "Notch signalling is linked to epidermal cell differentiation level in basal cell carcinoma, psoriasis and wound healing," *BMC Dermatol.* 2(1):7, BioMed Central, England (2002).
Thurston, G., et al., "The Delta paradox: DLL4 blockade leads to more tumour vessels but less tumour growth," *Nature Reviews Cancer* 7:327-331, Nature Publishing Group, New York, NY, USA (2007).
U.S. Appl. No. 12/497,405, inventors Yan et al., filed Jul. 2, 2009 (Now Abandoned).
Uyttendaele, H., et al., "Notch4 and Wnt-1 Proteins Function to Regulate Branching Morphogenesis of Mammary Epithelial Cells in an Opposing Fashion," *Dev. Biol.* 196:204-217, Elsevier Inc., Amsterdam, The Netherlands (1998).

(56) References Cited

OTHER PUBLICATIONS

Van Es, J.H., and Clevers, H., "Notch and Wnt inhibitors as potential new drugs for intestinal neoplastic disease," *Trends Mol. Med.* 11:496-502, Elsevier Inc., Amsterdam, The Netherlands (2005).
Van Limpt, V., et al., "SAGE Analysis of Neuroblastoma Reveals a High Expression of the Human Homologue of the *Drosophila delta* Gene," *Med. Pediatr. Oncol.* 35:554-558, Wiley-Liss, Inc., Massachusetts, U.S.A (2000).
Wang, J.C.Y., et al., "Primitive Human Hematopoeitic Cells Are Enriched in Cord Blood Compared with Adult Bone Marrow or Mobilized Peripheral Blood as Measured by the Quantitative In Vivo SCID-Repopulating Cell Assay," *Blood* 89:3919-3924, The American Society of Hematology (1997).
Weijzen, S., et al., "Activation of Notch-1 signaling maintains the neoplastic phenotype in human Ras-transformed cells," *Nat. Med.* 8:979-986, Nature Publishing Group, New York, NY, USA (2002).
Weng, A.P. et al., "Growth suppression of pre-T acute lymphoblastic leukemia cells by inhibition of notch signaling," *Mol Cell Biol.* 23(2):655-64, American Society for Microbiology, United States (2003).
Weng, A.P., et al., "Activating Mutations of *NOTCH1* in Human T Cell Acute Lymphoblastic Leukemia," *Science* 306:269-371, American Association for the Advancement of Science (2004).
Williams, C.K., et al., "Up-regulation of the Notch ligand Delta-like 4 inhibits VEGF-induced endothelial cell function," *Blood* 107:931-939 (Feb. 2006).
Wilson, A. and Radtke, F., "Multiple functions of Notch signaling in self-renewing organs and cancer," *FEBS Lett.* 580:2860-2868, Elsevier, Inc. (2006).
Written Opinion of the International Searching Authority for International Patent Application No. PCT/US11/60773, International Searching Authority, Alexandria, Virginia, United States, mailed Mar. 26, 2012.
Xu, A., et al., "Regions of *Drosophila* Notch that contribute to ligand binding and the modulatory influence of Fringe," *J. Biol. Chem.* 280(34): 30158-65, American Society for Biochemistry and Molecular Biology, United States (Aug. 2005; Epub: Jun. 2005).
Yan, M., et al., "Chronic DLL4 blockade induces vascular neoplasms," *Nature* 463:E6-E7, Macmillan Publishers Limited, England (2010).
Yan, X.-Q., et al., "A novel Notch ligand, *Dll4*, induces T-cell leukemia/lymphoma when overexpressed in mice by retroviral-mediated gene transfer," *Blood* 98:3793-3799, the American Society of Hematology, Washington, DC, USA (2001).
Yen, W.-C., et al., "Targeting Cancer Stem Cells and Vasculature by a Novel Anti-Dll4 Antibody Inhibits Pancreatic Tumor Growth and Delays Tumor Recurrence," presented at the 100th Annual Meeting of the American Association for Cancer Research in Denver, Colorado, on Apr. 18-22, 2009, 1 page.
Zagouras, P., et al., "Alterations in Notch signaling in neoplastic lesions of the human cervix," *PNAS* 92:6414-6418, the National Academy of Sciences, Washington, DC, USA (1995).
Nickoloff, B.J., et al., "Notch signaling as a therapeutic target in cancer: a new approach to the development of cell fate modifying agents," *Oncogene* 22(42):6598-6608, Nature Publishing Group, England (2003).
Office Action mailed Apr. 5, 2013 in U.S. Appl. No. 12/768,650, inventors Gurney, et al., filed Apr. 27, 2010.
Rudikoff, S., et al., "Single amino acid substitution altering antigen-binding specificity," *Proc. Natl. Acad. Sci. USA* 79:1979-1983, National Academy of Sciences, United States (1982).
Colman, P.M., "Effects of amino acid sequence changes on antibody-antigen interactions," *Res. Immunol.* 145(1):33-36, Elsevier, France (1994).
Portolano, S., et al., Lack of promiscuity in autoantigen-specific H and L chain combinations as revealed by human H and L chain "roulette," *J. Immunol.* 150(3):880-887, American Association of Immunologists, United States (1993).
Skolnick, J. and Fetrow, J.S., "From genes to protein structure and function: novel applications of computational approaches in the genomic era," *Trends Biotechnol.* 18(1):34-39, Elsevier Science Publishers, England (2000).
Burgess, W.H., "Possible dissociation of the heparin-binding and mitogenic activities of heparin-binding (acidic fibroblast) growth factor-1 from its receptor-binding activities by site-directed mutagenesis of a single lysine residue," *J. Cell Biol.* 111(5 Pt 1):2129-2138, Rockefeller University Press, United States (1990).
Lazar, E., et al., "Transforming growth factor alpha: mutation of aspartic acid 47 and leucine 48 results in different biological activities," *Mol. Cell Biol.* 8(3):1247-1252, American Society for Microbiology, United States (1988).
Merchant, A.M., et al., "An efficient route to human bispecific IgG," *Nat. Biotechnol.* 16(7):677-681, Nature America Publishing, United States (1998).
Barbas, III, C., et al., "In vitro evolution of a neutralizing human antibody to human immunodeficiency virus type 1 to enhance affinity and broaden strain cross-reactivity," *Proc Nat. Acad. Sci. USA* 91:3809-3813, National Academy of Sciences, United States (1994).
Bloom, J., et al., "Intrachain disulfide bond in the core hinge region of human IgG4," *Protein Science* 6:407-415, Cambridge University Press, United States (1997).
Boerner, P., et al., "Production of Antigen-Specific Human Monoclonal Antibodies From In Vitro-Primed Human Splenocytes," *J. Immunol.* 147:86-95, The American Association of Immunologists, United States (1991).
Brennan, M., et al., "Preparation of Bispecific Antibodies by Chemical Recombination of Monoclonal Immunoglobin $G_1$ Fragments," *Science* 229:81-83, National Academy of Sciences, United States (1985).
Carter, P., et al., "Humanization of an anti-p185$^{HER2}$ antibody for human cancer therapy," *Proc. Natl. Acad. Sci. USA* 89:4285-4289, Academy of Sciences, United States (1992).
Chothia, C., et al., "Domain Association in Immunoglobin Molecules: The Packing of Variable Domains," *J. Mol. Biol.* 186:651-663, Academic Press, United Kingdom (1985).
Chothia, C. and Lesk, A., "Canonical Structures for the Hypervariable Regions of Immunoglobulins," *J. Mol. Biol.* 196:901-917, Academic Press Limited, United States (1987).
Chowdhury, P. and Pastan, I., "Improving antibody affinity by mimicking somatic hypermutation in vitro," *Nat.Biotechnol.* 17:568-572, Nature Publishing Co., United States (1999).
Cole, S., et al., "The EBV-Hybridoma Technique and Its Application to Human Lung Cancer," pp. 77-96, Monoclonal Antibodies and Cancer Therapy, Proceedings of the Roche-UCLA Symposium, Park City, Utah, USA, Alan R. Liss, Inc., Jan. 26-Feb. 2, 1985.
Deisenhofer, J., "Crystallographic Refinement and Atomic Models of a Human Fc Fragment and Its Complex with Fragment B of Protein A from *Staphyloccocus aureus* at 2.9 and 2.8-A Resolution," *Biochemistry* 20:2361-2370, the American Chemical Society, United States (1981).
Dreher, M., et al., "Colony assays for antibody fragments expressed in bacteria," *J. Immunol. Methods* 139:197-205, Elsevier Science Publishers B.V., Netherlands (1991).
Eppstein, D., et al., "Biological activity of liposome-encapsulated murine interferon γ is mediated by a cell membrane receptor," *Proc. Natl. Acad. Sci. USA* 82:3688-3692, National Academy of Sciences, United States (1985).
Gruber, M., et al., "Efficient Tumor Cell Lysis Mediated by a Bispecific Single Chain Antibody Expressed in *Escherichia coli*," *J. Immunol.* 152:5368-5374, The American Association of Immunologists, United States (1994).
Harlow, E. and Lane, D., eds., "Chapter 14: Immunoassays," in *Antibodies: A Laboratory Manual*, pp. 553-612, Cold Spring Harbor Laboratory, Cold Spring Harbor, NY (1988).
Harris, W., "Therapeutic Monoclonals," *Biochem. Soc. Transactions* 23:1035-1038, Industrial Biochemistry and Biotechnology Group Colloquium, University of Manchester, United Kingdom (1995).

(56) References Cited

OTHER PUBLICATIONS

Hawkins, R., et al., "Selection of Phage Antibodies by Binding Affinity Mimicking Affinity Maturation," *J. Mol. Biol.* 226:889-896, Academic Press Limited, United States (1992).
Hermentin, P. and Seiler, F., "Investigations with Monoclonal Antibody Drug (Anthracycline) Conjugates," *Behring Inst. Mitt.* 82:197-215, Die Medizinische Verlagsgesellschaft mbH, W. Germany (1988).
Hoogenboom, H. and Winter, G., "By-passing Immunisation: Human Antibodies from Synthetic Repertoires of Germline $V_H$ Gene Segments Rearranged in Vitro," *J. Mol. Biol.* 227:381-388, Academic Press Limited, United States (1992).
Humphreys, D., et al., "Formation of dimeric Fabs in *Escherichia coli*: effect of hinge size and isotype, presence of interchain disulphide bond, Fab' expression levels, tail piece sequences and growth conditions," *J. Immunol. Methods* 209:193-202, Elsevier Science B.V., Netherlands (1997).
Hurle, M. and Gross, M., "Protein engineering techniques for antibody humanization," *Curr. Opin. Biotech.* 5:428-433, Current Biology Ltd., United States (1994).
Hwang, K., et al., "Hepatic uptake and degradation of unilamellar sphingomyelin/cholesterol liposomes: A kinetic study," *Proc. Natl. Acad. Sci. USA* 77:4030-4034, National Academy of Sciences, United States (1980).
Jackson, J., et al., "In Vitro Antibody Maturation," *J. Immunol.* 154:3310-3319, The American Association of Immunologists, United States (1995).
Jones, P., et al., "Replacing the complementarity-determining regions in a human antibody with those from a mouse," *Nature* 321:522-525, Nature Publishing Group, United Kingdom (1986).
Kingsman, A., et al., "Replication in *Saccharomyces cerevisiae* of Plasmid pBR313 Carrying DNA From the Yeast *trpl* Region," *Gene* 7:141-152, Elsevier/North-Holland Biomedical Press, Netherlands (1979).
Kostelny, S., et al., "Formation of a Bispecific Antibody by the Use of Leucine Zippers," *J. Immunol.* 148:1547-1553, The American Association of Immunologists, United States (1992).
Lee, H., et al., "Generation of characterization of a novel single-gene-encoded single-chain immunoglobulin molecular with antigen binding activity and effector functions," *Mol. Immunol.* 36:61-71, Elsevier Science Ltd., Netherlands (1999).
Maeda, H., et al., "Construction of reshaped human antibodies with HIV-neutralizing activity," *Hum. Antibod. Hybridomas* 2:124-134, Butterworth-Heinemann, United Kingdom (1991).
Marks, J., et al., "By-passing Immunization: Human Antibodies from V-gene Libraries Displayed on Phage," *J. Mol. Biol.* 222:581-597, Academic Press Limited, United Kingdom (1991).
Marks, J., et al., "By-Passing Immunization: Building High Affinity Human Antibodies by Chain Shuffling," *Bio/Technology* 10:779-783, Nature Publishing Co., United States (1992).
Milstein, C., et al., "Hybrid hybridomas and their use in immunohistochemistry," *Nature* 305:537-539, Nature Publishing Group, United Kingdom (1983).
Morimoto, K., et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Methods* 24:107-117, Elsevier Science Publishers B.V., Netherlands (1993).
Morrison, S., et al., "Chimeric human antibody molecules: Mouse antigen-binding domains with human constant region domains," *Proc. Natl. Acad. Sci. USA* 81:6851-6855, National Academy of Sciences, United States (1984).
Nohaile, M., et al., "Altering dimerization specificity by changes in surface electrostatics," *Proc. Natl. Acad. Sci. U.S.A.* 98:3109-3114, United States National Academy of Sciences, United States (2001).
Novotny, J. and Haber, E., "Structural invariants of antigen binding: Comparison of immunoglobin $V_L$-$V_H$ domain dimers," *Proc. Natl. Acad. Sci. USA* 82:4592-4596, National Academy of Sciences, United States (1985).
Presta, L., et al., "Humanization of an Antibody Directed Against IgE," *J. Immunol.* 151:2623-2632, The American Association of Immunologists, United States (1993).
Riechmann, L., et al., "Reshaping human antibodies for therapy," *Nature* 332:323-329, Nature Publishing Group, United States (1988).
Sal-Man, N., et al., "Arginine mutations within a transmembrane domain of Tar, an *Escherichia coli* aspartate receptor, can drive homodimer dissociation and heterodimer association in vivo," *Biochem. J.* 385:29-36, Portland Press, United Kingdom (2005).
Schier, R., et al., "Identification of function and structural amino-acid residues by parsimonious mutagenesis," *Gene* 169:147-155, Elsevier Science B.V., Netherlands (1996).
Shalaby, M., et al., "Development of Humanized Bispecific Antibodies Reactive with Cytotoxic Lymphocytes and Tumor Cells Overexpressing the HER2 Protooncogene," *J. Exp. Med.*175:217-225, The Rockefeller University Press, United States (1992).
Sheets, M., et al., "Efficient construction of a large nonimmune phage antibody library: The production of high-affinity human single-chain antibodies to protein antigens," *Proc. Natl. Acad Sci. USA* 95:6157-6162, National Academy of Sciences, United States (1998).
Sims, M., et al., "A Humanized CD18 Antibody Can Block Function without Cell Destruction," *J. Immunol.*151:2296-2308, The American Association of Immunologists, United States (1993).
Stinchcomb, D., et al., "Isolation and characterisation of a yeast chromosomal replicator," *Nature* 282:39-43, Nature Publishing Group, United Kingdom (1979).
Suresh, M., et al., "Bispecific Monoclonal Antibodies from Hybrid Hybridomas," *Methods Enzymol.* 121:210-228, Academic Press Inc., United Kingdom (1986).
Traunecker, A., et al., "Bispecific single chain molecules (Janusins) target cytotoxic lymphocytes on HIV infected cells," *EMBO J.*10:3655-3659, Oxford University Press, United Kingdom (1991).
Tutt, A., et al., "Trispecific F(ab')$_3$ Derivatives That Use Cooperative Signaling Via the TCR/CD3 Complex and CD2 to Activate and Redirect Resting Cytotoxic T Cells," *J. Immunol.* 147:60-69, The American Association of Immunologists, United States (1991).
Urlaub, G. and Chasin, L., "Isolation of Chinese hamster cell mutants deficient in dihydrofolate reductase activity," *Proc. Natl. Acad. Sci. USA* 77: 4216-4220, National Academy of Sciences, United States (1980).
Vaswani, S. and Hamilton, R., "Humanized antibodies as potential therapeutic drugs," *Ann. Allergy Asthma Immunol.* 81:105-119, American College of Allergy, Asthma, & Immunology, United States (1998).
Vaughan, T., et al., "Human Antibodies with Sub-nanomolar Affinities Isolated from a Large Non-immunized Phage Display Library," *Nat. Biotech.* 14:309-314, Nature Publishing Co., United States (1996).
Verhoeyen, M., et al., "Reshaping Human Antibodies: Grafting an Antilysozyme Activity," *Science* 239:1534-1536, American Association for the Advancement of Science, United States (1988).
Ward, E., "Antibody Engineering Using *Escherichia coli* as Host," *Adv. Pharmacol.* 24:1-20, Academic Press, Inc., United Kingdom (1993).
Wu, C., et al., "Simultaneous targeting of multiple disease mediators by a dual-variable-domain immunoglobulin," *Nat. Biotech.* 25:1290-1297, Nature Publishing Co., United States (2007).
Yelton, D., et al., "Affinity Maturation of the BR96 Anti-Carcinoma Antibody by Codon-Based Mutagenesis," *J. Immunol.* 155:1994-2004, The American Association of Immunologists, United States (1995).
International Search Report with the Written Opinion of the International Searching Authority for International application No. PCT/US10/32625, mailed on Dec. 17, 2010, United States Patent and Trademark Office, United States.
International Search Report with the Written Opinion of the International Searching Authority for International application No. PCT/US12/56886, mailed Feb. 28, 2013, United States Patent and Trademark Office, United States.
Co-pending U.S. Appl. No. 14/068,890, filed Oct. 31, 2013, inventors Benner et al. (Not Published).

(56) References Cited

OTHER PUBLICATIONS

Amado, R.G., et al., "Wild-Type KRAS is Required for Panitumumab Efficacy in Patients with Metastatic Colorectal Cancer," Journal of Clinical Oncology 26(10):1626-1634, American Society of Clinical Oncology, United States (2008).
Beviglia, L., et al., "Anti-DLL4 reduces tumor growth and tumorigenicity in B-RAF V600E melanomas including those with acquired resistance to B-RAF inhibitors," AACR 103rd Annual Meeting 2012, Mar. 31-Apr. 4, Abstract LB-196, 1 page (2012).
Beviglia, L., et al., "Anti-DLL4 Treatment Inhibits Melanoma Tumor Growth, Recurrence, Metastases and Reduces Frequency of Cancer Stem Cells in a Clinically Relevant Tumor Model in NOD/SCID Mice," Cancer Research 71(8 Suppl.):Abstract 2834, AACR 102nd Annual Meeting 2011, Apr. 2-6, 2011.
Beviglia, L., et al., "In vivo evaluation of anti-tumor activity by an anti-VEGF and anti-DLL4 bispecific antibody in a humanized model of skin graft," AACR 104th Annual Meeting 2013, Abstract 4330, Apr. 6-10, 1 page (2013).
Sica, D.A., "Angiogenesis Inhibitors and Hypertension," US Cardiovascular Disease 79-80, Touch Briefings, United States (2007).
Sullivan, D.C. and Bicknell, R., "New molecular pathways in angiogenesis," British Journal of Cancer 89:228-231, Cancer Research UK, United Kingdom (2003).
Brorson, K., et al., "Mutational Analysis of Avidity and Fine Specificity of Anti-Levan Antibodies," Journal of Immunology 163(12):6694-6701, American Association of Immunologists, United States (1999).
Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).
Burks, E.A., et al., "In vitro Scanning Saturation Mutagenesis of an Antibody Binding Pocket," Proceedings of the National Academy of Sciences of the United States of America 94(2):412-417, National Academy of Sciences, United States (1997).
Takeda, T. and Kohno, M., "Brain Natriuretic peptide in Hypertension," Hypertension Research 18(4):259-266, Nature Publishing Group, England (1995).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Chi, A.S., et al., "Angiogenesis as a Therapeutic Target in Malignant Gliomas," Oncologist 14(6):621-636, AlphaMed Press, United States (2009).
Claxton, S. and Fruttiger, M., "Periodic Delta-like 4 expression in developing retinal arteries," Gene Expression Pattern 5:123-127, Elsevier B.V., Netherlands (2004).
Cubillo, A., et al., "A Phase lb study of demcizumab (DEM, anti-DLL4) with gemcitabine (GEM) in patients with first line locally advanced or metastatic pancreatic cancer," Proceedings of the AACR-NCI-EORTC International Conference on Molecular Targets and Cancer Therapeutics, Oct. 19-23, 2013, Abstract B78, 2 pages (2013).
Deonarain, M.P., et al., "Antibodies Targeting Cancer Stem Cells: A New Paradigm in Immunotherapy?," mAbs 1(1):12-25,Taylor & Francis, United States (2009).
Tavares, M.J., et al., "Inhibition of Vascular Endothelium by the Notch-Ligand Delta-4 Unveils a Novel Therapeutic Target," Abstract#1944, Poster Board Session: 115-11, Blood 102(11):3 pages, American Society of Hematology, United States (2003).
Thurston, G., and Gale, N.W., "Vascular Endothelial Growth Factor and Other Signaling Pathways in Developmental and Pathologic Angiogenesis," International Journal of Hematology 80:7-20, The Japanese Society of Hematology, Japan (2004).
European Search Report for EP Application No. EP10824244.7, Munich, Germany, mailed on Feb. 18, 2013, 6 pages.
Ton, N.C. and Jayson, G.C., "Resistance to Anti-VEGF Agents," Current Pharmaceutical Design 10:51-64, Bentham Science Publishers Ltd., Netherlands (2004).

Fischer, M., et al., "Anti-DLL4 Inhibits Growth and Reduces Tumor-Initiating Cell Frequency in Colorectal Tumors with Oncogenic KRAS Mutations," Cancer Research 71(5):1520-1525, American Association for Cancer Research, United States (2011).
Wong, O.K., et al., "Voreloxin (formerly SNS-595) is a potent DNA intercalator and topoisomerase II poison that induces cell cycle dependent DNA damage and rapid apoptosis in cancer cell lines," 24th EORTC-NCI-AACR Symposium, Nov. 9, Poster 169, 1 page (2012).
Gagnon, M.L., et al., "Identification of a natural soluble neuropilin-1 that binds vascular endothelial growth factor: In vivo expression and antitumor activity," Proceedings of the National Academy of Sciences 97(6):2573-2578, National Academy of Sciences, United States (2000).
Yen, W-C., et al., "Anti-DLL4 (demcizumab) inhibits tumor growth and reduces cancer stem cell frequency in patient-derived ovarian cancer xenografts," AACR 104th Annual Meeting 2013, Abstract 3725, Apr. 6-10, 1 page (2013).
Yen, W-C., et al., "Dual targeting of DLL4 and VEGF signaling by a novel bispecific antibody inhibits tumor growth and reduces cancer stem cell frequency," AACR Annual Meeting 2014, Apr. 5-9, 2014, Abstract 207, 1 page (2014).
Gracian, A.C., et al., "A phase 1b study of the anticancer stem cell agent demcizumab (DEM) and gemcitabine (GEM) with or without paclitaxel protein bound particles (nab-paclitaxel) in patients with pancreatic cancer," 2014 Gastrointestinal Cancers Symposium, Abstract 279, 2 pages (2014).
Gray-Schopfer, V.C., et al., "The Role of B-RAF in Melanoma," Cancer Metastasis Reviews 24(1):165-183, Springer Science + Business Media, Inc., Netherlands (2005).
Gridley, T., "Notch Signaling During Vascular Development," Proceedings of the National Academy of Sciences 98(10):5377-5378, National Academy of Sciences, United States (2001).
Gronberg, B.H., et al., "Phase III Study by the Norwegian Lung Cancer Study Group: Pemetrexed Plus Carboplatin Compared with Gemcitabine Plus Carboplatin as First-line Chemotherapy in Advanced Non-small-cell Lung Cancer," Journal of Clinical Oncology 27(19):3217-3224, American Society of Clinical Oncology, United States (2009).
Yen, W-C., et al., "Targeting cancer stem cells by an anti-DLL4 antibody inhibits epithelial-to-mesenchymal transition, delays tumor recurrence and overcomes drug resistance in breast and pancreatic cancer," AACR 103rd Annual Meeting 2012, Mar. 31-Apr. 4, Abstract 3357, 1 page (2013).
Hidalgo, M., et al., "A Phase 1b Study of the Anti-Cancer Stem Cell Agent Demcizumab (DEM, anti-DLL4) and Gemcitabine (GEM) with or without Nab-Paclitaxvel in Patients with Pancreatic Cancer," European Society for Medical Oncology 2014 Congress, Sep. 17 and Sep. 28, Poster 616PD, 1 page (2014).
Holash, J., et al., "Inhibitors of growth factor receptors, signaling pathways and angiogenesis as therapeutic molecular agents," Cancer Metastasis Rev 25:243-252, Dordrecht, Netherlands (2006).
Holash, J., et al., "VEGF-Trap: A VEGF Blocker with Potent Antitumor Effects," Proceedings of the National Academy of Sciences USA 99(17):11393-11398, National Academy of Sciences, United States (2002).
OncoMed Pharmaceuticals Inc. SEC Form S-1 filed on Apr. 2, 2013, 21 pages.
Yen, W-C., et al., "The combination of gemcitabine/nab-paclitaxel and anti-DLL4 (demcizumab) produces synergistic growth inhibition, delays tumor recurrence and reduces tumor initiating cells in pancreatic cancer," American Association for Cancer Research Annual Meeting 2014, Abstract 1898, 1 page (2014).
International Preliminary Report on Patentability and Written Opinion for International Application No. PCT/US2010/53064, International Searching Authority, mailed on Feb. 14, 2011, 7 pages.
International Preliminary Report on Patentability for International Application No. PCT/US2013/065015, The International Bureau of WIPO, Switzerland, mailed on Apr. 22, 2014, 17 pages.
International Search Report for International Application No. PCT/US2010/53064, mailed on Feb. 14, 2011, 3 Pages.

(56) References Cited

OTHER PUBLICATIONS

Izzedine, H., et al., "Management of Hypertension in Angiogenesis Inhibitor-Treated Patients," Annals of Oncology 20(5):807-815, Oxford University Press, England (2009).
Lenihan, D.J., "How is cardiac toxicity defined and what impact does this have on cancer outcome or drug development," PowerPoint Presentation from the DIA Meeting, 42 slides (2011).
Jang, Y.J., et al., "The Structural Basis for DNA Binding by an Anti-DNA Autoantibody," Molecular Immunology 35(18):1207-1217, Pergamon Press, England (1998).
NCT01189968, "A Phase 1b Study of Carboplatin and Pemetrexed Plus OMP-21M18 as $1^{st}$-line Treatment in Subjects with Non-Squamous Non-Small Cell Lung Cancer" as updated on Aug. 26, 2010, ClinicalTrials.gov archive, accessed at https://clinicaltrials.gov/archive/NCT01189968/2010_08_26, accessed on Apr. 20, 2015,, 5 pages.
Kim, E.S., et al., "Potent VEGF blockade causes regression of coopted vessels in a model of neuroblastoma," Proceedings of the National Academy of Sciences 99(17):11399-11404, National Academy of Sciences, United States (2002).
OncoMed Pharmaceuticals Inc. SEC Form S-1 filed on Jul. 17, 2013, 26 pages.
NCT01189968, "A Phase 1b Study of Carboplatin and Pemetrexed Plus OMP-21M18 as $1^{st}$-line Treatment in Subjects with Non-Squamous Non-Small Cell Lung Cancer" as updated on Dec. 15, 2011, ClinicalTrials.gov archive, accessed at https://clinicaltrials.gov/archive/NCT01189968/2011_12_15, accessed on Apr. 20, 2015, 5 pages.
Kuo, C.J., et al., "Comparative evaluation of the antitumor activity of antiangiogenic proteins delivered by gene transfer," Proceedings of the National Academy of Sciences 98(8):4605-4610, National Academy of Sciences, United States (2001).
Li, X., et al., "Notch3 Signaling is Required for the Development of Pulmonary Arterial Hypertension," Nature Medicine 15(11):1289-1297, Nature Publishing Company, United States (2009).
Lievre, A., et al., "KRAS Mutation Status is Predictive of Response to Cetuzimab Therapy in Colorectal Cancer," Cancer Research 66(8):3992-3995, American Association for Cancer Research, United States (2006).
NCT01189929, "A Phase 1b Study of Gemcitabine Plus OMP-21M18 as $1^{st}$-line Treatment in Subjects With Locally Advanced of Metastatic Pancreatic Cancer" as updated on Aug. 26, 2010, ClinicalTrials.gov archive, accessed at http://clinicaltrials.gov/archives/NCT01189929/2010_08_26, accessed on Apr. 20, 2015, 5 pages.
Lu, K.V., and Bergers, G., "Mechanisms of evasive resistance to anti-VEGF therapy in glioblastoma," CNS Oncology 2(1):49-65, Future Medicine, Inc., United States (2013).
Luca, V.C., et al., "Structural basis for Notch1 engagement of Delta-like 4," Science, 347(6224):847-853, American Association for the Advancement of Science, United States (2015).
Maccallum, R.M., et al., "Antibody-Antigen Interactions: Contact Analysis and Binding Site Topography," Journal of Molecular Biology 262(5):732-745, Elsevier, England (1996).
McKeage, M., et al., "A Phase 1b study of demcizumab (DEM, anti-DLL4) plus pemetrexed and carboplatin in patients with first line stage IIIb/IV non-squamous non-small cell lung cancer," Proceedings of the AACR-NCI-EORTC International Conference on Molecular Targets and Cancer Therapeutics, Oct. 19-23, 2013, Abstract A71, 2 pages (2013).
McKeage, M.J., et al., "A phase 1b study of the anticancer stem cell agent demcizumab (DEM), pemetrexed (PEM), and carboplatin (CARBO) in pts with first-line nonsquamous NSCLC," 2014 ASCO Annual Meeting, Abstract 2544, 2 pages (2014).
NCT01189929, "A Phase 1b Study of Gemcitabine Plus OMP-21M18 as $1^{st}$-line Treatment in Subjects With Locally Advanced or Metastatic Pancreatic Cancer" as updated on Dec. 15, 2011, ClinicalTrials.gov archive, accessed at https://clinicaltrials.gov/archives/NCT01189929/2011_12_15, accessed on Apr. 20, 2015, 5 pages.

Office Action mailed Mar. 20, 2015 in U.S. Appl. No. 14/068,910, Benner, et al., filed Oct. 31, 2013.
OncoMed Pharmaceuticals, Press Release, "Clinical Cancer Research Publishes OncoMed Data Demonstrating Anti-Cancer Activity for Anti-DLL4 (Demcizumab) in Pancreatic Cancer," Sep. 6, 2012, 2 pages.
OncoMed Pharmaceuticals, Press Release, "OncoMed Announces Abstracts Accepted at the 2014 ASCO Annual Meeting," Apr. 23, 2014, 2 pages.
OncoMed Pharmaceuticals, Press Release, "OncoMed Anti-Cancer Stem Cell Antibody OMP-21M18 Demonstrates Potent Activity in Preclinical Studies Against Human Colon Cancer Tumors Regardless of KRAS Mutation Status," Mar. 1, 2011, 3 pages.
OncoMed Pharmaceuticals, Press Release, "OncoMed's Demcizumab Phase 1b Clinical Trials Show Encouraging Safety and Anti-Tumor Activity at ESMO," Sep. 28, 2014, 3 pages.
OncoMed Pharmaceuticals, Press Release, "OncoMed Pharmaceuticals Announces Presentations of Anti-Notch2/3 and Demcizumab Clinical Data at EORTC-NCI-AACR Meeting," Nov. 9, 2012, 3 pages.
OncoMed Pharmaceuticals, Press Release, "OncoMed Pharmaceuticals Initiates Phase 1b/2 Clinical Trial of Demcizuman (Anti-DLL4) in Combination with Paclitaxel in Ovarian Cancer," Sep. 19, 2013, 3 pages.
OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals, Press Release, "OncoMed Pharmaceuticals Presents Data From Demcizumab Phase 1b Clinical Study in Pancreatic Cancer at the 2014 Gastrointestinal Cancers Symposium," Jan. 17, 2014, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Data from Two Clinical Programs in Advanced Pancreatic Cancer at the 2014 Gastrointestinal Cancers Symposium," Jan. 9, 2014, 2 pages.
OncoMed Pharmaceuticals, Press Release, "OncoMed Pharmaceuticals Updates Phase 1b Data for Demcizumab With Pemetrexed and Carboplatin in Patients With First-Line Stage IIIb/IV Non-Small Cell Lung Cancer at the AACR-NCO-EORTC International Conference on Molecular Targets and Cancer Therapeutics in Boston, Oct. 19-23, 2013," Oct. 20, 2013, 3 pages.
OncoMed Pharmaceuticals, Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed Presents New Clinical and Biomarker Data From Its Tarextumab and Demcizumab Clinical Trials at the EORTC-NCI-AACR Symposium," Nov. 21, 2014, 3 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed to Present Clinical and Preclinical Data at the 26th EORTC-NCI-AACR Symposium on Molecular Targets and Cancer Therapeutics Meeting," Oct. 30, 2014, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present New and Emerging Data from Demcizumab (anti-DLL4, OMP-

(56) References Cited

OTHER PUBLICATIONS

21M18) and Tarextumab (anti-Notch2/3, OMP-59R5) Clinical Studies at the European Society for Medical Oncology 2014 Congress," Sep. 17, 2014, 2 pages.
OncoMed Pharmaceuticals Press Release, "OncoMed to Present New Data in Six Anti-Cancer Stem Cell Programs at AACR," Apr. 2, 2013, 2 pages.
McKeage, M., et al., "Phase 1b Study of Demcizumab plus Pemetrexed and Carboplatin in Patients with 1$^{st}$ line Non-Small Cell Lung Cancer (NSCLC)," AACR-NCI-EORTC International Conference on Molecular Targets and Cancer Therapeutics, Oct. 19-23, 2013, Poster (2013), 8 pages.
Pisano, C., et al., "Undersulfated, low-molecular-weight glycol-split heparin as an antiangiogenic VEGF antagonist," Glycobiology 15(2):1C-6C, Oxford University Press, England (2005).
McKeage, M., et al., "A Phase 1b Study of Demcizumab plus Pemetrexed and Carboplatin in Patients with 1$^{st}$ line Non-Squamous Non-Small Cell Lung Cancer (NSCLC)," 24$^{th}$ EORTC-NCI-AACR Symposium on Molecular Targets and Cancer Therapeutics, Nov. 6-9, 2012, Poster (2012), 9 pages.
Cubillo, A., et al., "A Ph1b Study of Demcizumab (DEM, anti-DLL4) with Gemcitabine (GEM) in Patients with 1$^{st}$ Line Locally Advanced or Metastatic Pancreatic Cancer," AACR-NCI-EORTC International Conference on Molecular Targets and Cancer Therapeutics, Oct. 19-23, 2013, Poster (2013), 8 pages.
Rehman, A.O. and Wang, C-U, "Notch signaling in the regulation of tumor angiogenesis," Trends in Cell Biology 16(6):293-300, Elsevier Ltd., England (2006).
OncoMed Pharmaceuticals Inc. SEC Form S-1 filed on May 11, 2012, 19 pages.
OncoMed Pharmaceuticals Inc. SEC Form S-1 filed on Jun. 15, 2012, 20 pages.
OncoMed Pharmaceuticals Inc. SEC Form S-1 filed on Jul. 3, 2012, 20 pages.
Shields, J.M., et al., "Lack of Extracellular Signal-Regulated Kinase Mitogen-Activated Protein Kinase Signaling Shows a New Type of Melanoma," Cancer Research 67(4):1502-1512, American Association for Cancer Research, United States (2007).
OncoMed Pharmaceuticals Inc. SEC Form S-1 filed on Oct. 25, 2012, 20 pages.
OncoMed Pharmaceuticals Inc. SEC Form S-1 filed on Dec. 3, 2012, 20 pages.
International Search Report for International Application No. PCT/US2015/024251, ISA/US, Alexandria, Virginia, United States, mailed on Jul. 16, 2015, 4 pages.
International Search Report with the Written Opinion of the International Searching Authority for International application No. PCT/US15/58327, United States Patent and Trademark Office, United States, mailed on May 19, 2016, 12 pages.
Janda, C.Y., "Structural Basis of Wnt Recognition by Frizzled," Science 337(6090):59-64, American Association for the Advancement of Science, United States (2012).
Nimmagadda, S., et al., "Expression pattern of Dll4 during chick embryogenesis," Histochem Cell Biol 128(2):147-152, Springer-Verlag, Germany (2007).
Oie, E., et al., "Activation of Notch signaling in cardiomyocytes during post-infarction remodeling," Scandinavian Cardiovascular Journal 44(6):359-366, Informa Healthcare, England (2010).
Smith, D.C., et al., "A First-in-Human, Phase I Trial of the Anti-DLL4 Antibody (OMP-21M18) Targeting Cancer Stem Cells (CSC) in Patients with Advanced Solid Tumors," European Journal of Cancer Supplement 8(7):73, Abstract 222, 1 page (2010).
Vincke, C., and Muyldermans, S., "Introduction to Heavy Chain Antibodies and Derived Nanobodies," Methods in Molecular Biology 911:15-26, Springer Science + Business Media, Germany (2012).
Written Opinion for International Application No. PCT/US2015/024251, ISA/US, Alexandria, Virginia, United States, mailed on Jul. 16, 2015, 7 pages.

Chartier, C., et al., "The Hippo Signaling Pathway Mediates BMP Inhibition of Cancer Stem Cells," 2015 AACR Annual meeting, Apr. 18-22, Abstract 2322, 1 page (2015).
Dupont, J., et al., "A Phase 1b Study of Anti-DLL4 (Delta-Like Ligand 4) Antibody Demcizumab (DEM) with Pemetrexed (PEM) and Carboplatin (CARBO) in Patients with 1st-Line Non-Squamous NSCLC," 2015 European Lung Cancer Conference (ELCC), Geneva, Switzerland, Apr. 15-18, Abstract 114, 2 pages (2015).
Hidalgo, M., et al., "A Phase 1b Study of the Anti-Cancer Stem Cell Agent Demcizumab (DEM, Anti-DLL4) and Gemcitabine (GEM) with or without Paclitaxel Protein Bound Particles (Nab-Paclitaxel) in pts with Pancreatic Cancer," 2015 ASCO Annual Meeting, Abstract 4118, 3 pages (2015).
Hidalgo, M., et al., "Pre-Clinical and Clinical Activity of Anti-DLL4 (Demcizumab) in Combination with Gemcitabine Plus nab-Paclitaxel in Pancreatic Cancer," 26th EORTC-NCI-AACR Symposium on Molecular Targets and Cancer Therapeutics Preclinical Models Poster Session, Abstract 166, 2 pages (Nov. 2014).
Hurwitz, H.I., et al., "Phase I Trial of Pazopanib in Patients with Advanced Cancer," Clinical Cancer Research 15(12):4220-4227, American Association for Cancer Research, United States (2009).
McKeage, M.J., et al., "A Phase 1b Study of the Anti-Cancer Stem Cell Agent Demcizumab (DEM), Pemetrexed (PEM) and Carboplatin (CARBO) inPatients with 1st Line Non-Squamous Non-Small Cell Lung Cancer (NSCLC)," 2015 ASCO Annual Meeting, Abstract 8045, 2 pages (2015).
Office Action mailed Mar. 20, 2015 in U.S. Appl. No. 13/826,103, Gurney, A.L., et al., filed Mar. 14, 2013.
OncoMed Pharmaceuticals Press Release, "OncoMed and Lilly Enter Clinical Supply Agreement to Evaluate the Combination of Demcizumab and Alimta(R) (pemetrexed for injection) in Lung Cancer," Apr. 2, 2015, 4 pages.
OncoMed Pharmaceuticals Press Release, "OncoMed Announces Abstracts Accepted for Presentation at the 2015 ASCO Annual Meeting," Apr. 21, 2015, 2 pages.
OncoMed Pharmaceuticals Press Release, "OncoMed Doses First Patient in Phase 1 Clinical Trial of Novel Anti-DLL4/VEGF Bispecific Antibody," Jan. 5, 2015, 2 pages.
OncoMed Pharmaceuticals Press Release, "OncoMed Highlights Immuno-Oncology Discoveries During 2015 Research & Development Day," Apr. 29, 2015, 3 pages.
OncoMed Pharmaceuticals Press Release, "OncoMed Initiates Dosing in Phase 2 Clinical Trial of Demcizumab for the Treatment of Non-Small Cell Lung Cancer," Feb. 4, 2015, 3 pages.
OncoMed Pharmaceuticals Press Release, "OncoMed Initiates Dosing in Randomized Phase 2 Clinical Trial of Demcizumab in Pancreatic Cancer Patients," Apr. 22, 2015, 3 pages.
Smith, D.C., et al., "A Phase I Dose Escalation and Expansion Study of the Anticancer Stem Cell Agent Demcizumab (Anti-DLL4) in Patients with Previously Treated Solid Tumors," Clinical Cancer Research 20(24):6295-6303, American Association for Cancer Research, United States (2014).
Srivastava, M., et al., "Dual Targeting of Delta-Like Ligand 4 (DLL4) and Programmed Death 1 (PD1) Inhibits Tumor Growth and Generates Enhanced Long-Term Immunological Memory," 2015 AACR Annual Meeting, Apr. 19, Abstract255, 1 page (2015).
Yan, Wei., "Design and Engineering of Fc Heterodimers for the Production of Bispecific Antibodies," Symposium Abstract, Keystone Symposia on Molecular and Cellular Biology, Accelerating Life Science Discovery, Mar. 27-Apr. 1, 2009, Whistler, British Columbia.
Yan, Wei, The Design and Engineering of Fc Heterodimers for the Production of Bispecific Antibodies and Other Heterodirner Fusion Proteins, Symposium Abstract, 20th Annual International Conference, Antibody Engineering, Antibody Engineering and Immunotherapeutics for the 21st Century, Dec. 6-10, 2009, San Diego, California.
Yan, Wei, "The Design and Engineering of Fc Heterodimers for the Production of Bispecific Antibodies," Symposium Abstract, Eleventh Annual Phage Display of Antibodies and Peptides, Approaches for 2nd Generation Biologics, Apr. 6-Apr. 7, 2009, Boston, Massachusetts.

(56) References Cited

OTHER PUBLICATIONS

Yen, W., et al., "Targeting Cancer Stem Cells and Vasculature by a Novel Anti-Delta-Like 4 Ligand (DLL4) Antibody for Treatment Triple Negative Breast Cancer," Cancer Research 69(Suppl.)(24):788s-789s, Abstract 5071, American Association for Cancer Research, United Sates (2009).

Yoneya, T., et al., "Molecular Cloning of Delta-4, A New Mouse and Human Notch Ligand," Journal of Biochemistry 129(1):27-34, Japanese Biochemical Society, Japan (2001).

OncoMed Pharmaceuticals Press Release, "OncoMed Pharmaceuticals to Review Key ASCO Data for Demcizumab and Tarextumab During Conference Call on Tuesday, Jun. 2, 2015," May 28, 2015, 2 pages.

OncoMed Pharmaceuticals Press Release, "OncoMed Presents Updated Demcizumab Data in Non-Small Cell Lung Cancer at the 2015 ASCO Annual Meeting," Jun. 1, 2015, 3 pages.

OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.

OncoMed Pharmaceuticals Press Release, "OncoMed Presents Demcizumab Data From Phase 1b Clinical Trial in Non-Small Cell Lung Cancer Patients at the European Lung Cancer Conference," Apr. 16, 2015, 3 pages.

OncoMed Pharmaceuticals Press Release, "OncoMed Presents Data From Phase 1b Trial of Demcizumab in Pancreatic Cancer at the 2015 ASCO Annual Meeting," Jun. 1, 2015, 3 pages.

OncoMed Pharmaceuticals Press Release, "OncoMed to Present Clinical Data for Demcizumab at the European Lung Cancer Conference," Apr. 9, 2015, 2 pages.

Schmidt, C., "Drug Makers Chase Cancer Stem Cells," Nature Biotechnology 26(4):366-367, Nature Publishing Group, United States (2008).

\* cited by examiner

Figure 1

| Patient No. | Cohort | Days on Study | BNP Trend pg/ml | LVEF[1] Trend | PTV[2] Trend | Comment |
|---|---|---|---|---|---|---|
| 1 | I: 5Q3w | 133 | Increased | All > 60% | ND | Discontinued Study paused |
| 7 | II: 2.5Q3w | 144 | 204 at d140 | All > 60% | All < 3.4 m/s | PD[3] at d140 Carvedilol at d142 |
| 8 | II: 2.5Q3w | 105 | 106 at d42 dec. to normal | All > 60% | All < 3.4 m/s | PD at d105 |
| 9 | II: 2.5Q3w | 112 | 165 at d42 dec. to normal | All > 60% | | PD at d112 ACE inhibitor |
| 14 | III: 5Q3w | 21 | 514 at d14 154 at d21 | All > 60% | All < 3.4 m/s | Discontinued Carvedilol and ACE inhibitor |
| 15 | III: 5Q3w | 126+ | 141 at d42 112 at d56 124 at d70 | All > 60% | All < 3.4 m/s | Ongoing Carvedilol |
| 17 | III: 5Q3w | 149+ | 100 at d14 dec. to normal | All > 60% | All < 3.4 m/s | Ongoing |
| 18 | III: 5Q3w | 106+ | 121 at d14 106 at d28 dec. to normal 150 at d56 119 at d70 213 at d84 | All > 50% | All < 3.4 m/s | Ongoing ACE inhibitor |

1. LVEF – Left ventricular ejection fraction
2. PTV – Peak triscupid velocity
3. PD - Progressive Disease

METHODS AND MONITORING OF TREATMENT WITH A DLL4 ANTAGONIST

CROSS-REFERENCE TO RELATED APPLICATIONS

This application claims priority benefit of U.S. Provisional Application No. 61/720,768, filed Oct. 31, 2012 which is hereby incorporated by reference herein in its entirety.

FIELD OF INVENTION

The present invention relates to the field of treating diseases with a DLL4 antagonist. More particularly, the invention provides methods for treating cancer comprising administering a DLL4 antagonist, either alone or in combination with other anti-cancer agents, and monitoring for cardiovascular side effects and/or toxicity.

REFERENCE TO SEQUENCE LISTING SUBMITTED ELECTRONICALLY VIA EFS-WEB

The content of the electronically submitted sequence listing (Name: 2293.0980002_SeqListing_07272015.txt; Size: 16.7 kilobytes; and Date of Creation: Jul. 27, 2015) is herein incorporated by reference in its entirety.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate-account for almost half of all new cases (Siegel et al., 2011, *CA: A Cancer J. Clin.* 61:212-236).

The Notch pathway is involved in multiple aspects of vascular development including proliferation, migration, smooth muscle differentiation, angiogenesis, and arterial-venous differentiation (Iso et al., 2003, *Arterioscler. Thromb. Vasc. Biol.* 23:543). The Notch receptor ligand DLL4 (Delta-like ligand 4) is an important component of the Notch pathway and plays a role in angiogenesis. Heterozygous loss of DLL4 results in severe defects in arterial development and yolk sac vascularization, leading to embryonic lethality (Duarte et al., 2004, *Genes Dev.*, 18:2474-78; Gale et al., 2004, *PNAS*, 101:15949-54; Krebs et al., 2004, *Genes Dev.*, 18:2469-73). Furthermore, tumor cells and tumor vasculature often over-express DLL4, suggesting that DLL4 expression is an important player in tumor angiogenesis (Patel et al., 2005, *Cancer Res.*, 65:8690-97; Yan et al., 2001, *Blood*, 98:3793-99). Thus, blocking DLL4 signaling has emerged as a promising path for the development of new anti-cancer therapies.

Blocking DLL4 signaling, such as by an anti-DLL4 antibody, has been shown to reduce tumor growth by multiple different mechanisms (Ridgway et al., 2006, *Nature*, 444:1083-87; Noguera-Troise et al., *Nature*, 444:1032-37; Hoey et al. 2009, *Cell Stem Cell*, 5:168-77). For example, DLL4 blocking antibodies have been reported to result in endothelial cell proliferation and the development of blood vessels, however, these blood vessels lack a functional lumen. This dysangiogenic effect has been reported to block tumor growth by promoting the development of only non-functional blood vessels (Ridgway et al., 2006, *Nature*, 444:1083-87; Noguera-Troise et al., *Nature*, 444:1032-37; Scehnet et al., 2007, *Blood*, 109:4753-60). Additionally, DLL4 blocking antibodies have been shown to inhibit tumor growth by reducing the proliferation of tumor cells and reducing cancer stem cell frequency. Although the mechanism behind the reduction of cancer stem cells or CSCs is unknown, it is hypothesized that DLL4 is required for the self-renewal of CSCs and maintains these cells in an undifferentiated state (Hoey et al., 2009, *Cell Stem Cell*, 5:168-77).

Unlike therapeutic approaches that attempt to block the signaling of tumor angiogenic factors, blockade of DLL4 signaling by anti-human DLL4 antibodies can result in endothelial hypertrophy and the creation of non-functional microvessels. Consequently, even in the presence of tumor angiogenic factors, blockade of DLL4 signaling, through administration of anti-human DLL4 antibodies, can result in dysangiogenesis which inhibits the ability of the tumor to induce the functional blood vessel formation needed to support growth of the tumor.

Chemotherapy is a well-established therapeutic approach for numerous cancers, but its efficacy can be limited by side effects and/or toxicity. In addition, targeted therapies such as the anti-ErbB2 receptor (HER2) antibody trastuzumab (HERCEPTIN), tyrosine kinase inhibitors imatinib (GLEEVEC), dasatinib (SPRYCEL), nilotibib (TASIGNA), sunitinib (SUTENT), sorafenib (NEXAVAR), the anti-VEGF antibody bevacizumab (AVASTIN), and anti-angiogenesis drugs sunitinib (SUTENT) and sorafenib (NEXAVAR), are known to cause, or are likely to cause, side effects and/or toxicity in subjects who take them. For example, bevacizumab, sunitinib, and sorfenib are known to cause hypertension in about one-third of patients who take them. In recent studies it has been found that anti-DLL4 antibodies may have side effects and/or toxicity in some subjects. For example, it has been found that anti-DLL4 antibodies can cause hypertension in some patients. This was surprising, since anti-DLL4 antibodies have been reported to inhibit tumor angiogenesis by promoting dysangiogensis, a mechanism different than that of traditional anti-angiogenic treatments.

BRIEF SUMMARY OF THE INVENTION

The present invention provides improved methods for treating diseases comprising administering to a subject a therapeutically effective amount of a DLL4 antagonist. For example, in one aspect the invention provides methods of screening for, detecting, identifying, monitoring, reducing, preventing, and/or attenuating a cardiovascular side effect and/or toxicity related to treatment with a DLL4 antagonist. In some embodiments, the methods comprise determining the level of a natriuretic peptide in a sample from a patient who has received, is receiving, will receive, or is being considered for initial or further treatment with a DLL4 antagonist, including but not limited to an anti-DLL4 antibody.

In another aspect, the invention provides methods of selecting a subject for treatment with a DLL4 antagonist, comprising: obtaining a biological sample from the subject, determining the level of a biomarker in the sample, and selecting the subject for treatment with the DLL4 antagonist if the level of the biomarker is below a predetermined level. In some embodiments, the biomarker is a natriuretic peptide. Thus, in some embodiments, the method of selecting a subject for treatment with a DLL4 antagonist, comprises: obtaining a biological sample from the subject, determining the level of a natriuretic peptide in the sample, and selecting the subject for treatment with the DLL4 antagonist if the level of the natriuretic peptide is below a predetermined level. In some embodiments, the biological sample is blood, serum, or plasma. In some embodiments, the natriuretic peptide is B-type natriuretic peptide (BNP). In some embodiments, the predetermined level is about 300 pg/ml or less in a blood, serum, or plasma sample. In some embodiments, the predetermined level is about 200 pg/ml or less in a blood, serum, or plasma sample. In some embodiments, the predetermined level is about 250 pg/ml or less in a blood, serum, or plasma sample. In some embodiments, the predetermined level is about 200 pg/ml or less in a blood, serum, or plasma sample. In some embodiments, the predetermined level is about 150 pg/ml or less in a blood, serum, or plasma sample. In some embodiments, the predetermined level is about 100 pg/ml or less in a blood, serum, or plasma sample.

In another aspect, the invention provides methods of identifying a subject as eligible for treatment with a DLL4 antagonist, comprising: obtaining a biological sample from the subject, determining the level of a biomarker in the sample, and identifying the subject as eligible for treatment with the DLL4 antagonist if the level of the biomarker is below a predetermined level. In some embodiments, the biomarker is a natriuretic peptide. In some embodiments, the method of identifying a subject as eligible for treatment with a DLL4 antagonist, comprises: obtaining a biological sample from the subject, determining the level of a natriuretic peptide in the sample, and identifying the subject as eligible for treatment with the DLL4 antagonist if the level of the natriuretic peptide is below a predetermined level. In some embodiments, the natriuretic peptide is BNP. In some embodiments, the biological sample is blood, serum, or plasma. In some embodiments, the predetermined level is about 300 pg/ml or less in a blood, serum, or plasma sample. In some embodiments, the predetermined level is about 200 pg/ml or less in a blood, serum, or plasma sample. In some embodiments, the predetermined level is about 250 pg/ml or less in a blood, serum, or plasma sample. In some embodiments, the predetermined level is about 2100 pg/ml or less in a blood, serum, or plasma sample. In some embodiments, the predetermined level is about 150 pg/ml or less in a blood, serum, or plasma sample. In some embodiments, the predetermined level is about 100 pg/ml or less in a blood, serum, or plasma sample.

In another aspect, the invention provides methods of monitoring a subject receiving treatment with a DLL4 antagonist for the development of cardiovascular side effects and/or toxicity, comprising: obtaining a biological sample from the subject receiving treatment, determining the level of a biomarker in the sample, and comparing the level of the biomarker in the sample to a predetermined level of the biomarker, wherein an increase in the level of the biomarker indicates development of cardiovascular side effects and/or toxicity. In some embodiments, the biomarker is a natriuretic peptide. In some embodiments, the method of monitoring a subject receiving treatment with a DLL4 antagonist for the development of cardiovascular side effects and/or toxicity, comprises: obtaining a biological sample from the subject receiving treatment, determining the level of a natriuretic peptide in the sample, and comparing the level of the natriuretic peptide in the sample to a predetermined level of the natriuretic peptide, wherein an increase in the level of the natriuretic peptide indicates development of cardiovascular side effects and/or toxicity. In some embodiments, the natriuretic peptide is BNP.

In another aspect, the invention provides methods of detecting the development of cardiovascular side effects and/or toxicity in a subject receiving treatment with a DLL4 antagonist, comprising: obtaining a biological sample from the subject receiving treatment, determining the level of a biomarker in the sample, and comparing the level of the biomarker in the sample to a predetermined level of the biomarker, wherein an increase in the level of the biomarker indicates development of cardiovascular side effects and/or toxicity. In some embodiments, the biomarker is a natriuretic peptide. In some embodiments, the method of detecting the development of a cardiovascular side effect and/or toxicity in a subject receiving treatment with a DLL4 antagonist, comprises: obtaining a biological sample from the subject receiving treatment, determining the level of a natriuretic peptide in the sample, and comparing the level of the natriuretic peptide in the sample to a predetermined level of the natriuretic peptide, wherein an increase in the level of the natriuretic peptide indicates development of a cardiovascular side effect and/or toxicity. In some embodiments, the natriuretic peptide is BNP.

In another aspect, the invention provides methods for identifying cardiovascular side effects and/or toxicity in a subject receiving treatment with a DLL4 antagonist, comprising: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then a cardiovascular side effect and/or toxicity is indicated. In some embodiments, the biomarker is a natriuretic peptide. In some embodiments, the method for identifying cardiovascular side effects and/or toxicity in a subject receiving treatment with a DLL4 antagonist, comprises: obtaining a biological sample from the subject receiving treatment, determining the level of a natriuretic peptide in the sample, and comparing the level of the natriuretic peptide in the sample to a predetermined level of the natriuretic peptide, wherein if the level of the natriuretic peptide in the sample is higher than the predetermined level of the natriuretic peptide then a cardiovascular side effect and/or toxicity is indicated. In some embodiments, the natriuretic peptide is BNP.

In another aspect, the invention provides methods for monitoring cardiovascular side effects and/or toxicity in a subject receiving treatment with a DLL4 antagonist, comprising: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then a cardiovascular side effect and/or toxicity is indicated. In some embodiments, the biomarker is a natriuretic peptide. In some embodiments, the method for monitoring cardiovascular side effects and/or toxicity in a subject receiving treatment with a DLL4 antagonist, comprises: obtaining a biological sample from the subject receiving treatment, determining the level of a natriuretic peptide in the sample, and comparing the level of the natriuretic peptide in the sample to a predetermined level of the natriuretic peptide, wherein if the level of the natriuretic peptide in the sample is higher than the predetermined level of the natriuretic peptide then a cardiovascular side effect and/or toxicity is indicated. In some embodiments, the natriuretic peptide is BNP.

In some aspects and/or embodiments of the methods described herein, the biological sample is blood, serum, or plasma. In some embodiments, the predetermined level is about 300 pg/ml or less in a blood, serum, or plasma sample. In some embodiments, the predetermined level is about 200 pg/ml or less in a blood, serum, or plasma sample. In some embodiments, the predetermined level is about 250 pg/ml or less in a blood, serum, or plasma sample. In some embodiments, the predetermined level is about 200 pg/ml or less in a blood, serum, or plasma sample. In some embodiments, the predetermined level is about 150 pg/ml or less in a blood, serum, or plasma sample. In some embodiments, the predetermined level is about 100 pg/ml or less in a blood, serum, or plasma sample. In some embodiments, the predetermined level of a biomarker (e.g. natriuretic peptide or BNP) is the amount of the biomarker in a sample obtained at an earlier date. In some embodiments, the predetermined level of a biomarker (e.g., natriuretic peptide or BNP) is the amount of the biomarker in a sample obtained prior to treatment. In some embodiments, the predetermined level of a biomarker (e.g., natriuretic peptide or BNP) is a normal reference level. In some embodiments, the predetermined level for BNP is about 100 pg/ml or less in blood, serum, or plasma.

In some aspects and/or embodiments of the methods described herein, a biological sample is obtained approximately every week, every 2 weeks, every 3 weeks, or every 4 weeks.

In some aspects and/or embodiments of the methods described herein, wherein if the natriuretic peptide level in the sample is above a predetermined level for two consecutive samples, the subject is administered a therapeutically effective amount of a cardioprotective medication such as an ACE inhibitor and/or a β-blocker. In some embodiments, the natriuretic peptide is BNP and the predetermined level is about 100 pg/ml. In some embodiments of the methods described herein, wherein if the natriuretic peptide level in the sample is above a predetermined level for any one sample, the subject is administered a therapeutically effective amount of an inhibitor and/or a β-blocker. In some embodiments, the natriuretic peptide is BNP and the predetermined level is about 200 pg/ml. In some embodiments of the methods described herein, wherein the natriuretic peptide level in the sample is above a predetermined level for any one sample, the subject is administered a therapeutically effective amount of an ACE inhibitor and/or a β-blocker and the DLL4 antagonist is withheld. In some embodiments, the natriuretic peptide is BNP and the predetermined level is about 300 pg/ml. In some embodiments, if the natriuretic peptide level decreases to below about 200 pg/ml after administration of the ACE inhibitor and/or a β-blocker, then administration of the DLL4 antagonist is resumed. In some embodiments, if the natriuretic peptide level decreases to below about 300 pg/ml after administration of the ACE inhibitor and/or a β-blocker, then administration of the DLL4 antagonist is resumed.

In another aspect, the invention provides methods of reducing cardiovascular side effects and/or toxicity in a subject receiving treatment with a DLL4 antagonist, comprising: obtaining a biological sample from the subject receiving treatment, determining the level of a natriuretic peptide in the sample, comparing the level of the natriuretic peptide in the sample to a predetermined level of the natriuretic peptide, and administering to the subject a therapeutically effective amount of a cardioprotective medication such as an ACE inhibitor and/or a β-blocker if the level of the natriuretic peptide in the sample is higher than the predetermined level of the natriuretic peptide. In another aspect, the invention provides methods of preventing or attenuating the development of cardiovascular side effects and/or toxicity in a subject receiving treatment with a DLL4 antagonist, comprising: obtaining a biological sample from the subject prior to treatment with the DLL4 antagonist, determining the level of a natriuretic peptide in the sample, comparing the level of the natriuretic peptide in the sample to a predetermined level of the natriuretic peptide, administering to the subject a therapeutically effective amount of a cardioprotective medication such as an ACE inhibitor and/or a β-blocker, and administering to the subject the DLL4 antagonist. In another aspect, the invention provides methods of ameliorating cardiovascular side effects and/or toxicity in a subject administered a DLL4 antagonist, comprising: determining the level of a natriuretic peptide in the sample, and administering to the subject a therapeutically effective amount of a cardioprotective medication such as an ACE inhibitor and/or a β-blocker. In some embodiments, the natriuretic peptide is BNP.

In another aspect, the invention provides methods of screening a subject for the risk of cardiovascular side effects and/or toxicity from treatment with a DLL4 antagonist, comprising: obtaining a biological sample from the subject prior to treatment with the DLL4 antagonist, determining the level of a natriuretic peptide in the sample, and comparing the level of the natriuretic peptide in the sample to a predetermined level of the natriuretic peptide, wherein if the level of the natriuretic peptide in the sample is higher than the predetermined level then the subject is at risk for cardiovascular side effects and/or toxicity. In some embodiments, if the subject is at risk for cardiovascular side effects and/or toxicity, the subject is administered a therapeutically effective amount of a therapeutic agent directed to the cardiovascular side effect and/or toxicity prior to treatment with the DLL4 antagonist.

In any of the aspects and/or embodiments of the methods described herein, the DLL4 antagonist specifically binds human DLL4. In some embodiments, the DLL4 antagonist is an antibody that specifically binds the extracellular domain of human DLL4. In some embodiments, the DLL4 antagonist specifically binds an epitope within amino acids 27-217 of the extracellular domain of human DLL4 (SEQ ID NO:17). In some embodiments, the DLL4 antagonist binds an epitope comprising amino acids 66-73 (QAVVSPGP, SEQ ID NO:18) of human DLL4. In some embodiments, the DLL4 antagonist binds an epitope comprising amino acids 139-146 (LISKIAIQ, SEQ ID NO: 19) of human DLL4. In some embodiments, the DLL4 antagonist binds an epitope comprising amino acids 66-73 (QAWSPGP, SEQ ID NO:18) and amino acids 139-146 (LISKIAIQ, SEQ ID NO:19) of human DLL4. In some embodiments, the DLL4 antagonist binds human DLL4 with a dissociation constant ($K_D$) of about 100 nM to about 0.1 nM.

In certain embodiments, the DLL4 antagonist is an anti-DLL4 antibody. In certain embodiments, the DLL4 antagonist is an antibody comprising a heavy chain CDR1 comprising TAYYIH (SEQ ID NO: 1), a heavy chain CDR2 comprising YISSYNGATNYNQKFKG (SEQ ID NO:3), and a heavy chain CDR3 comprising RDYDYDVGMDY (SEQ ID NO:5), and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In certain embodiments, the DLL4 antagonist is an antibody comprising a heavy chain variable region comprising the amino acids of SEQ ID NO:10. In certain embodiments, the DLL4 antagonist is an antibody which further comprises a light chain variable region comprising the amino acids of SEQ ID NO: 12. In certain embodiments, the DLL4 antagonist comprises the same heavy and light chain amino acid sequences as an antibody encoded by a plasmid deposited with ATCC having deposit no. PTA-8425 or PTA-8427. In certain embodiments, the DLL4 antagonist comprises the heavy chain CDR amino acid sequences and the light chain CDR amino acid sequences that are contained in the 21M18 antibody produced by the hybridoma deposited with ATCC having deposit no. PTA-8670. In certain embodiments, the DLL4 antagonist is encoded by the plasmid having ATCC deposit no. PTA-8425 which was deposited with American Type Culture Collection (ATCC), at 10801 University Boulevard, Manassas, Va., 20110, under the conditions of the Budapest Treaty on May 10, 2007. In certain embodiments, the DLL4 antagonist is encoded by the plasmid having ATCC deposit no. PTA-8427 which was deposited with American Type Culture Collection (ATCC), at 10801 University Boulevard, Manassas, Va., 20110, under the conditions of the Budapest Treaty on May 10, 2007. In some embodiments, the DLL4 antagonist is the antibody produced by the hybridoma having ATCC deposit no. PTA-8670 which was deposited with the ATCC under the conditions of the Budapest Treaty on Sep. 28, 2007. In some embodiments, the DLL4 antagonist is a humanized version of the antibody produced by the hybridoma having ATCC deposit no. PTA-8670. In certain embodiments, the DLL4 antagonist competes for specific binding to human DLL4 with an antibody encoded by the plasmid deposited with ATCC having deposit no. PTA-8425 or PTA-8427.

In any of the aspects and/or embodiments of the methods described herein, the subject has cancer. In some embodiments, the cancer is selected from the group consisting of: lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma multiforme, cervical cancer, stomach cancer, bladder cancer, hepatoma, and head and neck cancer.

In any of the aspects and/or embodiments of the methods described herein, the subject is treated with the DLL4 antagonist in combination with one or more additional anti-cancer agents.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE FIGURES

FIG. 1. The table is a summary of some of the subjects enrolled in the Phase 1b clinical trial for treatment of NSCLC with OMP-21M18 in combination with carboplatin and pemetrexed.

DETAILED DESCRIPTION OF THE INVENTION

Figure 2:
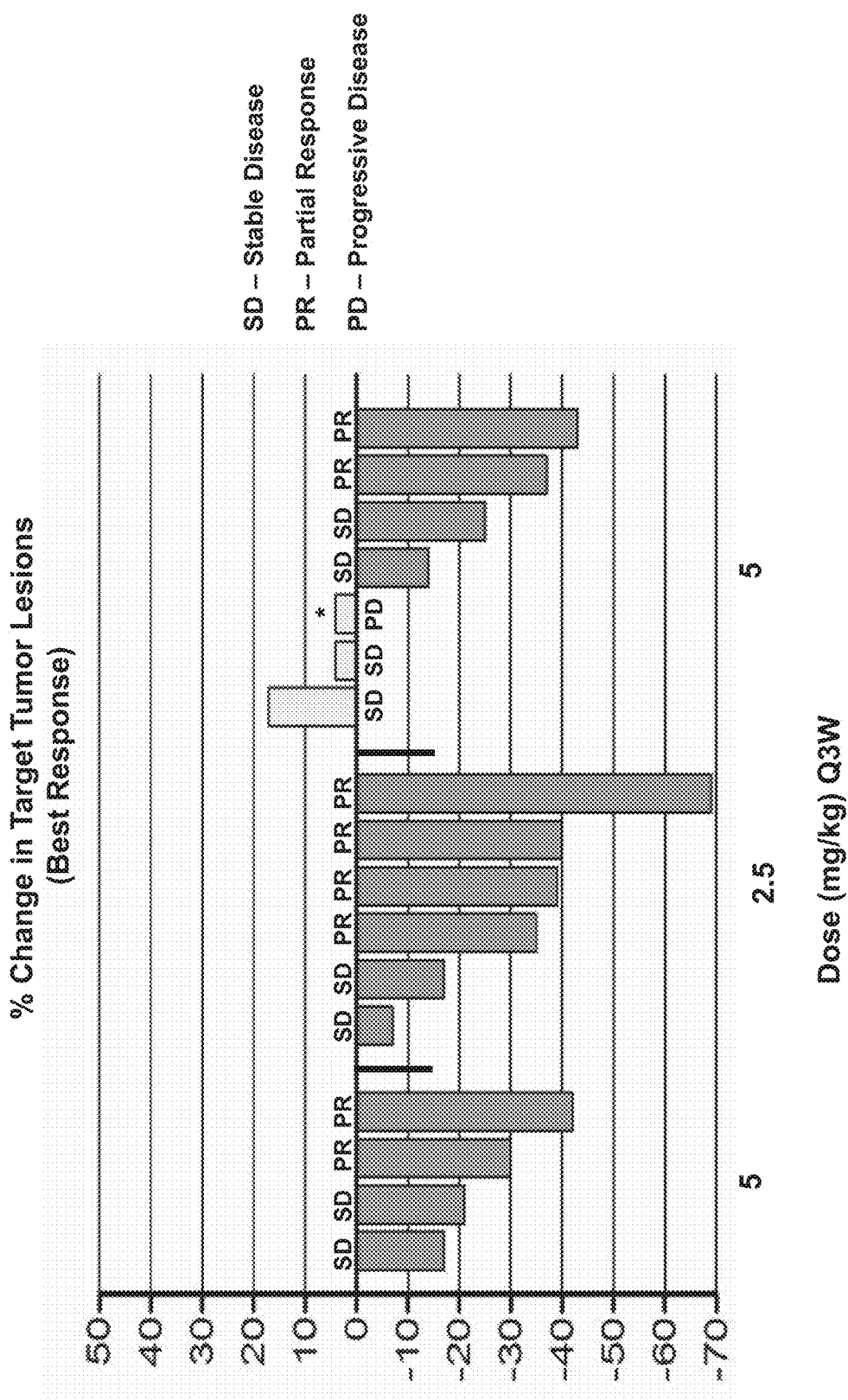
FIG. 2. Percent change in target tumor lesions in subjects enrolled in the Phase 1b clinical trial for treatment of NSCLC with OMP-21M18 in combination with carboplatin and pemetrexed.

The present invention relates to treating diseases with a DLL4 antagonist. More particularly, the invention provides methods for treating cancer comprising administering a DLL4 antagonist, either alone or in combination with other anti-cancer agents, and monitoring for cardiovascular side effects and/or toxicity, including those related to the DLL4 antagonist.

The anti-DLL4 antibody OMP-21M18 was administered to subjects in a Phase 1 single agent dose escalation trial. The data from this early trial, as well as results from animal studies suggested that administration of a DLL4 antagonist such as an anti-DLL4 antibody may result in cardiovascular side effects and/or toxicity in certain patients. Furthermore, the study showed that increased BNP levels may be an early indicator that a patient being treated with a DLL4 antagonist is at risk of developing cardiotoxicity, allowing for intervention with cardioprotective medications.

These results made it desirable to develop risk mitigation and monitoring strategies for cardiovascular side effects and/or toxicities as described herein for subjects receiving treatment with a DLL4 antagonist (e.g. an anti-DLL4 antibody) as a single agent or in combination with additional anti-cancer agents.

I. DEFINITIONS

To facilitate an understanding of the present invention, a number of terms and phrases are defined below.

The terms "antagonist" and "antagonistic" as used herein refer to any molecule that partially or fully blocks, inhibits, reduces or neutralizes a biological activity of a target and/or signaling pathway (e.g. Notch signaling). The term "antagonist" is used herein to include any molecule that partially or fully blocks, inhibits, reduces or neutralizes the activity of a protein (e.g., DLL4). As used herein the term "DLL4 antagonist" refers to a molecule that partially or fully blocks, inhibits, neutralizes, or interferes with the biological activities of a DLL4 protein. This includes, but is not limited to, blocking, inhibiting, reducing, or interfering with DLL4/Notch interactions, DLL4-induced Notch pathway signaling, and/or DLL4 signaling. Suitable antagonist molecules specifically include, but are not limited to, antagonist DLL4 antibodies or antibody fragments.

The terms "modulation" and "modulate" as used herein refer to a change or an alteration in a biological activity. Modulation includes, but is not limited to, stimulating or inhibiting an activity. Modulation may be an increase or a decrease in activity (e.g., a decrease in Notch signaling), a change in binding characteristics, or any other change in the biological, functional, or immunological properties associated with the activity of a protein, pathway, or other biological point of interest.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies such as bispecific antibodies generated from at least two intact antibodies, monospecific antibodies, monovalent antibodies, chimeric antibodies, humanized antibodies, human antibodies, fusion proteins comprising an antigen determination portion of an antibody, and any other modified immunoglobulin molecule comprising an antigen recognition site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of the antibody light chain, or the variable region of the antibody heavy chain, either alone or in combination. The variable regions of the heavy and light chain each consist of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability (i.e., Kabat et al., 1991, *Sequences of Proteins of Immunological Interest, 5th Edition*, National Institutes of Health, Bethesda Md.), and (2) an approach based on crystallographic studies of antigen-antibody complexes (Al-Lazikani et al., 1997, *J. Mol. Biol.,* 273:927-948). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and transgenic animals.

The term "humanized antibody" as used herein refers to forms of antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region residues of a human immunoglobulin are replaced with the corresponding residues in an antibody from a non-human species that has the desired specificity, affinity, and/or binding capability. The humanized antibody can be further modified by the substitution of additional residues either in the Fv framework region and/or within the replaced non-human residues to refine and optimize antibody specificity, affinity, and/or binding capability. In some embodiments, the humanized antibody will comprise substantially all of at least one, and typically two or three, variable domains containing all or substantially all of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in, for example, U.S. Pat. No. 5,225,539.

The term "human antibody" as used herein refers to an antibody produced by a human or an antibody having an amino acid sequence corresponding to an antibody produced by a human made using any of the techniques known in the art. This definition of a human antibody specifically excludes a humanized antibody comprising non-human antigen-binding residues.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions are homologous to the sequences in antibodies derived from another species (e.g., human).

The phrase "affinity-matured antibody" as used herein refers to an antibody with one or more alterations in one or more CDRs thereof that result in an improvement in the affinity of the antibody for antigen, compared to a parent antibody that does not possess those alterations(s). Preferred affinity-matured antibodies will have nanomolar or even picomolar affinities for the target antigen. Affinity-matured antibodies are produced by procedures known in the art. For example, Marks et al., 1992, *Bio/Technology* 10:779-783, describes affinity maturation by VH and VL domain shuffling. Random mutagenesis of CDR and/or framework residues is described by Barbas et al., 1994, *PNAS,* 91:3809-3813; Schier et al., 1995, *Gene,* 169:147-155; Yelton et al., 1995, *J. Immunol.* 155:1994-2004; Jackson et al., 1995, *J. Immunol.* 154:3310-9; and Hawkins et al., 1992, *J. Mol. Biol.,* 226:889-896.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "selectively binds" or "specifically binds" mean that a binding agent or an antibody reacts or associates more frequently, more rapidly, with greater duration, with greater affinity, or with some combination of the above to the epitope, protein, or target molecule than with alternative substances, including unrelated or related proteins. In certain embodiments "specifically binds" means, for instance, that an antibody binds a protein with a $K_D$ of about 0.1 mM or less, but more usually less than about 1 µM. In certain embodiments, "specifically binds" means that an antibody binds a target at times with a $K_D$ of at least about 0.1 µM or less, at other times at least about 0.01 µM or less, and at other times at least about 1 nM or less. Because of the sequence identity between homologous proteins in different species, specific binding can include an antibody that recognizes a protein in more than one species (e.g., human DLL4 and mouse DLL4). Likewise, because of homology within certain regions of polypeptide sequences of different proteins, specific binding can include an antibody (or other polypeptide or binding agent) that recognizes more than one protein. It is understood that, in certain embodiments, an antibody or binding moiety that specifically binds a first target may or may not specifically bind a second target. As such. "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins. In some embodiments, an antibody may be bispecific or multispecific and comprise at least two antigen-binding sites with differing specificities. For example, a bispecific antibody may comprise one antigen-binding site that recognizes an epitope on one protein and further comprise a second, different antigen-binding site that recognizes a different epitope on a second protein. Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains (e.g., dimers).

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value therebetween. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more RSPO protein(s) to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (non-cancerous) or malignant (cancerous) including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates (e.g., via the bloodstream or lymph) from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to approved or approvable by a regulatory agency of the Federal or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the pharmacological activity thereof and is nontoxic when administered in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject. In the case of cancer, the therapeutically effective amount of a drug (e.g., an antibody) has a therapeutic effect and as such can reduce the number of cancer cells; decrease tumorigenicity, tumorigenic frequency, or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. In some embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. DLL4 ANTAGONISTS

In certain embodiments, the DLL4 antagonist specifically binds the extracellular domain of human DLL4. In some embodiments, the DLL4 antagonist is an antibody. In some embodiments, the DLL4 antagonist or antibody specifically binds an epitope within amino acids 27-217 of the extracellular domain of human DLL4 (SEQ ID NO: 17). In some embodiments, the DLL4 antagonist or antibody specifically binds an epitope formed by a combination of the N-terminal region of human DLL4 (SEQ ID NO: 14) and the DSL region of human DLL4 (SEQ ID NO: 15). In some embodiments, the DLL4 antagonist or antibody specifically binds within the N-terminal region of human DLL4 (SEQ ID NO: 14). In some embodiments, the DLL4 antagonist or antibody binds an epitope comprising amino acids 66-73 (QAVVSPGP; SEQ ID NO: 18) of human DLL4. In some embodiments, the DLL4 antagonist or antibody binds an epitope comprising amino acids 139-146 (LISKIAIQ; SEQ ID NO: 19) of human DLL4. In some embodiments, the DLL4 antagonist or antibody binds an epitope comprising amino acids 66-73 (QAVVSPGP; SEQ ID NO: 18) and amino acids 139-146 (LISKIAIQ; SEQ ID NO:19) of human DLL4.

In certain embodiments, the DLL4 antagonist (e.g., an antibody) binds to human DLL4 with a dissociation constant ($K_D$) of about 1 µM or less, about 100 nM or less, about 40 nM or less, about 20 nM or less, about 10 nM or less, or about 1 nM or less. In certain embodiments, the DLL4 antagonist or antibody binds to human DLL4 with a $K_D$ of about 40 nM or less, about 20 nM or less, about 10 nM or less, or about 1 nM or less. In certain embodiments, the DLL4 antagonist binds to human DLL4 with a $K_D$ of about 1 nM. In certain embodiments, the DLL4 antagonist binds to human DLL4 with a $K_D$ of about 0.8 nM. In certain embodiments, the DLL4 antagonist binds to human DLL4 with a $K_D$ of about 0.6 nM. In certain embodiments, the DLL4 antagonist binds to human DLL4 with a $K_D$ of about 0.5 nM. In certain embodiments, the DLL4 antagonist binds to human DLL4 with a $K_D$ of about 0.4 nM. In some embodiments, the $K_D$ is measured by surface plasmon resonance. In some embodiments, the dissociation constant of the antagonist or antibody to DLL4 is the dissociation constant determined using a DLL4 fusion protein comprising a DLL4 extracellular domain (e.g., a DLL4 ECD-Fc fusion protein) immobilized on a Biacore chip.

In certain embodiments, the DLL4 antagonist (e.g., an antibody) binds to DLL4 with a half maximal effective concentration ($EC_{50}$) of about 1 µM or less, about 100 nM or less, about 40 nM or less, about 20 nM or less, about 10 nM or less, or about 1 nM or less. In certain embodiments, the DLL4 antagonist or antibody binds to human DLL4 with an $EC_{50}$ of about 40 nM or less, about 20 nM or less, about 10 nM or less, or about 1 nM or less.

In certain embodiments, the DLL4 antagonist is a polypeptide. In certain embodiments, the DLL4 antagonist or polypeptide is an antibody. In certain embodiments, the antibody is an IgG antibody. In some embodiments, the antibody is an IgG1 antibody. In some embodiments, the antibody is an IgG2 antibody. In certain embodiments, the antibody is a monoclonal antibody. In some embodiments, the antibody is a bispecific antibody. In certain embodiments, the antibody is a humanized antibody. In certain embodiments, the antibody is a human antibody. In certain embodiments, the antibody is an antibody fragment comprising an antigen-binding site.

The DLL4 antagonists (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry. Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see, e.g., Ausubel et al., Editors, 1994-present, *Current Protocols in Molecular Biology*, John Wiley & Sons, Inc., New York. N.Y.).

In some embodiments, the specific binding of a DLL4 antagonist (e.g., an antibody) to human DLL4 may be determined using ELISA. An ELISA assay comprises preparing DLL4 antigen, coating wells of a 96 well microtiter plate with antigen, adding to the wells the DLL4 antagonist or antibody conjugated to a detectable compound such as an enzymatic substrate (e.g., horseradish peroxidase or alkaline phosphatase), incubating for a period of time and detecting the presence of the binding agent or antibody. In some embodiments, the DLL4 antagonist or antibody is not conjugated to a detectable compound, but instead a second conjugated antibody that recognizes the DLL4 antagonist or antibody is added to the well. In some embodiments, instead of coating the well with DLL4 antigen, the DLL4 antagonist or antibody can be coated on the well, antigen is added to the coated well and then a second antibody conjugated to a detectable compound is added. One of skill in the art would be knowledgeable as to the parameters that can be modified and/or optimized to increase the signal detected, as well as other variations of ELISAs that can be used (see, e.g., Ausubel et al. Editors, 1994-present, *Current Protocols in Molecular Biology*, John Wiley & Sons, Inc., New York, N.Y.).

In some embodiments, the specific binding of a DLL4 antagonist (e.g., an antibody) to human DLL4 may be determined using FACS. A FACS screening assay may comprise generating a cDNA construct that expresses an antigen as a fusion protein, transfecting the construct into cells, expressing the antigen on the surface of the cells, mixing the DLL4 antagonist with the transfected cells, and incubating for a period of time. The cells bound by the DLL4 antagonist may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antagonist or antibody to DLL4 and the on-off rate of an antibody-antigen interaction can be determined by competitive binding assays. In some embodiments, a competitive binding assay is a radioimmunoassay comprising the incubation of labeled antigen (e.g., $^3$H or $^{125}$I), or fragment or variant thereof, with the antibody of interest in the presence of increasing amounts of unlabeled antigen followed by the detection of the antibody bound to the labeled antigen. The affinity of the antibody for the antigen and the on-off rates can be determined from the data by Scatchard plot analysis. In some embodiments, Biacore kinetic analysis is used to determine the binding affinities and on-off rates of antagonists or antibodies that bind DLL4. Biacore kinetic analysis comprises analyzing the binding and dissociation of antibodies from antigens (e.g., DLL4 proteins) that have been immobilized on the surface of a Biacore chip. In some embodiments, Biacore kinetic analyses can be used to study binding of different antibodies in qualitative epitope competition binding assays.

In some embodiments, the DLL4 antagonists are polyclonal antibodies. Polyclonal antibodies can be prepared by any known method. Polyclonal antibodies are prepared by immunizing an animal (e.g., a rabbit, rat, mouse, goat, donkey) by multiple subcutaneous or intraperitoneal injections of the relevant antigen (e.g., a purified peptide fragment, full-length recombinant protein, fusion protein, etc.). The antigen can be optionally conjugated to a carrier protein such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from blood, ascites, and the like, of the immunized animal. Polyclonal antibodies can be purified from serum or ascites according to standard methods in the art including, but not limited to, affinity chromatography, ion-exchange chromatography, gel electrophoresis, and dialysis.

In some embodiments, the DLL4 antagonists are monoclonal antibodies. Monoclonal antibodies can be prepared using hybridoma methods known to one of skill in the art (see e.g., Kohler and Milstein, 1975, *Nature* 256:495). Using the hybridoma method, a mouse, hamster, or other appropriate host animal, is immunized as described above to elicit lymphocytes to produce antibodies that will specifically bind the immunizing antigen. In some embodiments, lymphocytes are immunized in vitro. In some embodiments, the immunizing antigen (e.g., DLL4) is a human protein or a portion thereof. In some embodiments, the immunizing antigen (e.g., DLL4) is a mouse protein or a portion thereof. In some embodiments, the immunizing antigen is an extracellular domain of human DLL4. In some embodiments, the immunizing antigen is an extracellular domain of mouse DLL4. In some embodiments, a mouse is immunized with a human antigen. In some embodiments, a mouse is immunized with a mouse antigen.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed against a target antigen may be identified by a variety of techniques including, but not limited to, immunoprecipitation, immunoblotting, and in vitro binding assays (e.g., flow cytometry, enzyme-linked immunosorbent assay (ELISA), or radioimmunoassay (RIA)). The hybridomas can be propagated either in in vitro culture using standard methods (J. W. Goding, 1996, *Monoclonal Antibodies: Principles and Practice*, 3rd Edition, Academic Press, San Diego, Calif.) or in vivo as ascites in a host animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies can be made using recombinant DNA techniques as known to one skilled in the art (see e.g., U.S. Pat. No. 4,816,567). For example, the polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional techniques. The isolated polynucleotides encoding the heavy and light chains are cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins. In certain embodiments, recombinant monoclonal antibodies, or fragments thereof, can be isolated from phage display libraries expressing variable domain regions or CDRs of a desired species (see e.g., McCafferty et al., 1990, *Nature*, 348:552-554; Clackson et al., 1991, *Nature*, 352: 624-628; and Marks et al., 1991, *J. Mol. Biol.*, 222:581-597).

The polynucleotide(s) encoding a monoclonal antibody can be modified, for example, by using recombinant DNA technology to generate alternative antibodies. In some embodiments, the constant domains of the light and heavy chains of, for example, a mouse monoclonal antibody can be substituted for those regions of, for example, a human antibody to generate a chimeric antibody or for a non-immunoglobulin polypeptide to generate a fusion antibody. In some embodiments, the constant regions are truncated or removed to generate the desired antibody fragment of a monoclonal antibody. In some embodiments, site-directed or high-density mutagenesis of the variable region can be used to optimize specificity, affinity, and/or other biological characteristics of a monoclonal antibody. In some embodiments, site-directed mutagenesis of the CDRs can be used to optimize specificity, affinity, and/or other biological characteristics of a monoclonal antibody.

In some embodiments, the DLL4 antagonist is a humanized antibody. Typically, humanized antibodies are human immunoglobulins in which residues from the complementary determining regions (CDRs) are replaced by residues from CDRs of a non-human species (e.g., mouse, rat, rabbit, hamster) that have the desired specificity, affinity, and/or capability by methods known to one skilled in the art. In some embodiments, the Fv framework region residues of a human immunoglobulin are replaced with the corresponding framework region residues from a non-human immunoglobulin that has the desired specificity, affinity, and/or capability. In some embodiments, the humanized antibody is further modified by the substitution of additional residues either in the Fv framework region and/or within the replaced non-human residues to refine and optimize antibody specificity, affinity, and/or capability. In general, the humanized antibody will comprise substantially all of at least one, or typically two or three, variable domains containing all, or substantially all, of the CDRs that correspond to the non-human immunoglobulin whereas all, or substantially all, of the framework regions are those of a human immunoglobulin consensus sequence. In some embodiments, the humanized antibody can also comprise at least a portion of an immunoglobulin constant region or domain (Fc), typically that of a human immunoglobulin. In certain embodiments, such humanized antibodies are used therapeutically because they should be less antigenic and may reduce HAMA (human anti-mouse antibody) responses when administered to a human subject. One skilled in the art would be able to obtain a functional humanized antibody with reduced immunogenicity following known techniques (see, e.g., U.S. Pat. Nos. 5,225,539; 5,585,089; 5,693,761; and 5,693,762).

In some embodiments, the invention provides an antibody that specifically binds the extracellular domain of human DLL4, wherein the antibody comprises one, two, three, four, five, and/or six of the CDRs of antibodies 21M18, 21M18 H9L2, and/or 21M18 H7L2. These antibodies have been described in U.S. Pat. No. 7,750,124, filed Sep. 28, 2007. Antibodies 21M18 H7L2 and 21M18 H9L2 are humanized versions of the murine 21M18 antibody. Antibody 21M18 H17L2 is also referred to as OMP-21M18 and demcizumab.

In certain embodiments, the invention provides a DLL4 antagonist, wherein the antagonist is a DLL4 antibody that specifically binds an epitope within amino acids 27-217 of the extracellular domain of human DLL4, and wherein the antibody comprises: a heavy chain CDR1 comprising TAYYIH (SEQ ID NO: 1), a heavy chain CDR2 comprising YISCYNGATNYNQKFKG (SEQ ID NO:2) YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5). In some embodiments, the antibody further comprises a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the antibody comprises a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the DLL4 antibody comprises a heavy chain CDR1 comprising TAYYIH (SEQ ID NO: 1), a heavy chain CDR2 comprising YISSYNGATNYNQKFKG (SEQ ID NO:3), and a heavy chain CDR3 comprising RDYDYDVGMDY (SEQ ID NO:5); and a light chain CDR1 comprising RASESVDNYGISFMK (SEQ ID NO:6) a light chain CDR2 comprising AASNQGS (SEQ ID NO:7), and a light chain CDR3 comprising QQSKEVPWTFGG (SEQ ID NO:8).

In certain embodiments, the invention provides an antibody that specifically binds an epitope within amino acids 27-217 of the extracellular domain of human DLL4, wherein the antibody comprises a heavy chain variable region having at least about 80% sequence identity to SEQ ID NO:9, SEQ ID NO:10, or SEQ ID NO: 11, and/or a light chain variable region having at least 80% sequence identity to SEQ ID NO: 12. In certain embodiments, the antibody comprises a heavy chain variable region having at least about 85%, at least about 90%, at least about 95%, at least about 97%, or at least about 99% sequence identity to SEQ ID NO:9, SEQ ID NO:10, or SEQ ID NO: 11. In certain embodiments, the antibody comprises a light chain variable region having at least about 85%, at least about 90%, at least about 95%, at least about 97%, or at least about 99% sequence identity to SEQ ID NO: 12. In certain embodiments, the antibody comprises a heavy chain variable region having at least about 95% sequence identity to SEQ ID NO:9, and/or a light chain variable region having at least about 95% sequence identity to SEQ ID NO:12. In certain embodiments, the antibody comprises a heavy chain variable region comprising SEQ ID NO:9, and/or a light chain variable region comprising SEQ ID NO: 12. In certain embodiments, the antibody comprises a heavy chain variable region comprising SEQ ID NO:9 and a light chain variable region comprising SEQ ID NO: 12. In certain embodiments, the antibody comprises a heavy chain variable region having at least about 95% sequence identity to SEQ ID NO: 10, and/or a light chain variable region having at least about 95% sequence identity to SEQ ID NO: 12. In certain embodiments, the antibody comprises a heavy chain variable region comprising SEQ ID NO: 10, and/or a light chain variable region comprising SEQ ID NO: 12. In certain embodiments, the antibody comprises a heavy chain variable region comprising SEQ ID NO: 10 and a light chain variable region comprising SEQ ID NO: 12. In certain embodiments, the antibody comprises a heavy chain variable region having at least about 95% sequence identity to SEQ ID NO: 11, and/or a light chain variable region having at least about 95% sequence identity to SEQ ID NO: 12. In certain embodiments, the antibody comprises a heavy chain variable region comprising SEQ ID NO: 11, and/or a light chain variable region comprising SEQ ID NO: 12. In certain embodiments, the antibody comprises a heavy chain variable region comprising SEQ ID NO: 11 and a light chain variable region comprising SEQ ID NO: 12.

In certain embodiments, the anti-DLL4 antibody is the antibody produced by the hybridoma deposited with ATCC on Sep. 28, 2007 and having ATCC deposit number PTA-8670, also known as murine 21M18. The murine 21M18 antibody is described in detail in U.S. Pat. No. 7,750,124, filed Sep. 28, 2007.

In certain embodiments, the anti-DLL4 antibody is the antibody encoded by the plasmid deposited with ATCC on May 10, 2007, having ATCC deposit number PTA-8425, also known as 21M18 H7L2 and OMP-21M18. The OMP-21M18 antibody is described in detail in U.S. Pat. No. 7,750,124, filed Sep. 28, 2007. The anti-DLL4 antibody OMP-21M18 comprises a heavy chain variable region comprising CDR amino acid sequences CDR1 (SEQ ID NO:1); CDR2 (SEQ ID NO:3); and CDR3 (SEQ ID NO:5); and a light chain variable region comprising CDR amino acid sequences CDR1 (SEQ ID NO:6); CDR2 (SEQ ID NO:7); and CDR3 (SEQ ID NO:8). In one embodiment, the OMP-21M18 antibody comprises the heavy chain variable region sequence of SEQ ID NO: 10 and the light chain variable region sequence of SEQ ID NO: 12.

In certain embodiments, the anti-DLL4 antibody is the antibody encoded by the plasmid deposited with ATCC on May 10, 2007, having ATCC deposit number PTA-8427, also known as 21M18 H19L2. The 21M18 H9L2 antibody is described in detail in U.S. Pat. No. 7,750,124, filed Sep. 28, 2007.

In certain embodiments, the DLL4 antagonist (e.g., an antibody) binds to the same epitope that an antibody comprising the heavy chain variable region comprising SEQ ID NO: 10, and/or a light chain variable region comprising SEQ ID NO: 12 binds. In certain embodiments, the DLL4 antagonist (e.g., an antibody) binds to the same epitope that an antibody comprising the heavy chain variable region comprising SEQ ID NO:9, and/or a light chain variable region comprising SEQ ID NO: 12 binds. In certain embodiments, the DLL4 antagonist (e.g., an antibody) binds to the same epitope that an antibody comprising the heavy chain variable region comprising SEQ ID NO: 11, and/or a light chain variable region comprising SEQ ID NO: 12 binds. In some embodiments, the DLL4 antagonist or antibody binds to the same epitope as murine antibody 21M18. In some embodiments, the DLL4 antagonist or antibody binds to the same epitope as humanized antibody 21M18 H7L2 (OMP-21M18). In some embodiments, the DLL4 antagonist or antibody binds to the same epitope as humanized antibody 21M18 H9L2.

In certain embodiments, the DLL4 antagonist (e.g., an antibody) competes for specific binding to an extracellular domain of human DLL4 with an antibody, wherein the antibody comprises a heavy chain variable region comprising SEQ ID NO: 10, and/or a light chain variable region comprising SEQ ID NO: 12. In certain embodiments, the DLL4 antagonist (e.g., an antibody) competes for specific binding to an extracellular domain of human DLL4 with an antibody, wherein the antibody comprises a heavy chain variable region comprising SEQ ID NO:9, and/or a light chain variable region comprising SEQ ID NO:12. In certain embodiments, the DLL4 antagonist (e.g., an antibody) competes for specific binding to an extracellular domain of human DLL4 with an antibody, wherein the antibody comprises a heavy chain variable region comprising SEQ ID NO: 11, and/or a light chain variable region comprising SEQ ID NO: 12. In some embodiments, the DLL4 antagonist competes for specific binding to an extracellular domain of human DLL4 with an antibody encoded by the plasmid deposited with ATCC having deposit no. PTA-8425. In some embodiments, the DLL4 antagonist or antibody competes for specific binding to an extracellular domain of human DLL4 with an antibody encoded by the plasmid deposited with ATCC having deposit no. PTA-8427. In some embodiments, the DLL4 antagonist or antibody competes for specific binding to an extracellular domain of human DLL4 with an antibody produced by the hybridoma deposited with ATCC having deposit no. PTA-8670. In some embodiments, the DLL4 antagonist or antibody competes for specific binding to an epitope within amino acids 27-217 of the extracellular domain of human DLL4 in a competitive binding assay. Other anti-DLL4 antibodies are known in the art and may be used in the methods described herein.

In certain embodiments, the DLL4 antagonist is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated (see, e.g., Cole et al. 1985, *Monoclonal Antibodies and Cancer Therapy*, Alan R. Liss, p. 77; Boerner et al., 1991, *J. Immunol.*, 147:86-95; and U.S. Pat. Nos. 5,750,373; 5,567,610; and 5,229,275).

In some embodiments, the human antibody can be selected from a phage library, wherein the phage library expresses human antibodies (Vaughan et al., 1996, *Nature Biotechnology*, 14:309-314; Sheets et al., 1998, *PNAS*, 95:6157-6162; Hoogenboom and Winter, 1991, *J. Mol. Biol.*, 227:381; Marks et al., 1991, *J. Mol. Biol.*, 222:581). Alternatively, phage display technology can be used to produce human antibodies and antibody fragments in vitro, from immunoglobulin variable domain gene repertoires from unimmunized donors. Techniques for the generation and use of antibody phage libraries are described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.*, 376:1182-1200.

Once antibodies are identified, affinity maturation strategies known in the art, including but not limited to, chain shuffling (Marks et al., 1992, *Bio/Technology*, 10:779-783) and site-directed mutagenesis, may be employed to generate high affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments, the DLL4 antagonist is a bispecific antibody. Bispecific antibodies are capable of specifically recognizing and binding to at least two different epitopes. The different epitopes can either be within the same molecule or on different molecules. In some embodiments, the antibodies can specifically recognize and bind a first antigen target, (e.g., DLL4) as well as a second antigen target, such as an effector molecule on a leukocyte (e.g., CD2, CD3, CD28, or B7) or a Fc receptor (e.g., CD64, CD32, or CD16) so as to focus cellular defense mechanisms to the cell expressing the first antigen target. In some embodiments, the antibodies can be used to direct cytotoxic agents to cells which express a particular target antigen, such as DLL4. These antibodies possess an antigen-binding arm and an arm which binds a cytotoxic agent or a radionuclide chelator, such as EOTUBE, DPTA, DOTA, or TETA. In certain embodiments, the antibodies can be used to affect angiogenesis. In certain embodiments, the bispecific antibody specifically binds DLL4, as well as a second Notch ligand (e.g., Jagged1 or Jagged2), or at least one Notch receptor selected from the group consisting of Notch1, Notch2, Notch3, and Notch4. In certain embodiments, the bispecific antibody specifically binds DLL4, as well as VEGF. In some embodiments, the bispecific antibody is a bispecific antibody disclosed in U.S. patent application Ser. No. 13/625,417, filed on Sep. 24, 2012. In some embodiments, the anti-VEGF/DLL4 bispecific antibody is 219R45-MB-21M18, 219R45-MB-21R79, 219R45-MB-21R75, or 219R45-MB-21R83 as disclosed in U.S. patent application Ser. No. 13/625,417, filed on Sep. 24, 2012.

Techniques for making bispecific antibodies are known by those skilled in the art, see for example, Millstein et al., 1983, *Nature*, 305:537-539; Brennan et al., 1985, *Science*, 229:81; Suresh et al, 1986, *Methods in Enzymol.*, 121:120; Traunecker et al., 1991, *EMBO J.*, 10:3655-3659; Shalaby et al., 1992, *J. Exp. Med.*, 175:217-225; Kostelny et al., 1992, *J. Immunol.* 148:1547-1553; Gruber et al., 1994, *J. Immunol.*, 152:5368; U.S. Pat. No. 5,731,168; and U.S. Patent Application Pub. No. 2011/0123532). Bispecific antibodies can be intact antibodies or antibody fragments. Antibodies with more than two valencies are also contemplated. For example, trispecific antibodies can be prepared (Tutt et al., 1991, *J. Immunol.*, 147:60). Thus, in certain embodiments the antibodies to DLL4 are multispecific.

In certain embodiments, the DLL4 antagonists (e.g., antibodies or other polypeptides) described herein may be monospecific. For example, in certain embodiments, each of the one or more antigen-binding sites that an antibody contains is capable of binding (or binds) a homologous epitope on DLL4.

In certain embodiments, the DLL4 antagonist is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in, and secreted from, E. coli or other host cells, allowing for the production of large amounts of these fragments. In some embodiments, antibody fragments are isolated from antibody phage libraries as discussed herein. For example, methods can be used for the construction of Fab expression libraries (Huse et al., 1989, Science, 246: 1275-1281) to allow rapid and effective identification of monoclonal Fab fragments with the desired specificity for DLL4, or derivatives, fragments, analogs or homologs thereof. In some embodiments, antibody fragments are linear antibody fragments. In certain embodiments, antibody fragments are monospecific or bispecific. In certain embodiments, the DLL4 antagonist is a scFv. Various techniques can be used for the production of single-chain antibodies specific to DLL4 (see, e.g., U.S. Pat. No. 4,946,778).

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

For the purposes of the present invention, it should be appreciated that modified antibodies, or fragments thereof, can comprise any type of variable region that provides for the association of the antibody with DLL4. In this regard, the variable region may be derived from any type of mammal that can be induced to mount a humoral response and generate immunoglobulins against a desired antigen (e.g., DLL4). As such, the variable region of the modified antibodies can be, for example, of human, murine, non-human primate (e.g., cynomolgus monkeys, macaques, etc.) or lepine origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification. Although the CDRs may be derived from an antibody of the same class or even subclass as the antibody from which the framework regions are derived, it is envisaged that the CDRs will be derived from an antibody of a different class and preferably from an antibody from a different species. It may not be necessary to replace all of the CDRs with all of the CDRs from the donor variable region to transfer the antigen binding capacity of one variable domain to another. Rather, it may only be necessary to transfer those residues that are necessary to maintain the activity of the antigen binding site.

Alterations to the variable region notwithstanding, those skilled in the art will appreciate that the modified antibodies of this invention will comprise antibodies (e.g., full-length antibodies or antigen-binding fragments thereof) in which at least a fraction of one or more of the constant region domains has been deleted or otherwise altered so as to provide desired biochemical characteristics, such as increased tumor localization, increased tumor penetration, reduced serum half-life or increased serum half-life when compared with an antibody of approximately the same immunogenicity comprising a native or unaltered constant region. In some embodiments, the constant region of the modified antibodies comprises a human constant region. Modifications to the constant region include additions, deletions, or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the entire CH2 domain has been removed (ΔCH2 constructs). In some embodiments, the omitted constant region domain is replaced by a short amino acid spacer (e.g., 10 as residues) that provides some of the molecular flexibility typically imparted by the absent constant region.

In certain embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase tumor localization and/or tumor penetration. Similarly, it may be desirable to simply delete the part of one or more constant region domains that control a specific effector function (e.g., complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells, release of inflammatory mediators, placental transfer and control of immunoglobulin production.

In certain embodiments, the DLL4 antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody (e.g., DLL4 antibody) thereby increasing tumor localization and/or penetration. In other embodiments, the constant region modifications increase or reduce the serum half-life of the antibody. In some embodiments, the constant region is modified to eliminate disulfide linkages or oligosaccharide moieties allowing for enhanced tumor localization and/or penetration.

In certain embodiments, a DLL4 antibody does not have one or more effector functions. In some embodiments, the antibody has no antibody-dependent cellular cytoxicity (ADCC) activity and/or no complement-dependent cytoxicity (CDC) activity. In certain embodiments, the antibody does not bind to an Fc receptor and/or complement factors. In certain embodiments, the antibody has no effector function.

The present invention further embraces variants and equivalents which are substantially homologous to the chimeric, humanized, and human antibodies, or antibody fragments thereof, set forth herein. These can contain, for example, conservative substitution mutations, i.e. the substitution of one or more amino acids by similar amino acids.

Thus, the present invention provides methods for generating an antibody that binds the extracellular domain of human DLL4. In some embodiments, the method for generating an antibody that binds DLL4 comprises using hybridoma techniques. In some embodiments, the method comprises using an extracellular domain of mouse DLL4 or human DLL4 as an immunizing antigen. In some embodiments, the method of generating an antibody that binds DLL4 comprises screening a human phage library. The present invention further provides methods of identifying an antibody that binds to DLL4. In some embodiments, the antibody is identified by screening for binding to DLL4 with flow cytometry (FACS). In some embodiments, the antibody is screened for binding to human DLL4. In some embodiments, the antibody is screened for binding to mouse DLL4. In some embodiments, the antibody is identified by screening for inhibition or blocking of DLL4-induced Notch activation. In some embodiments, the DLL4 is human DLL4. In some embodiments, the Notch is human Notch1, Notch2, Notch3, or Notch4.

In certain embodiments, the antibodies described herein are isolated. In certain embodiments, the antibodies described herein are substantially pure.

Certain anti-DLL4 antibodies have been described, for example, in U.S. Pat. No. 7,750,124. Additional anti-DLL4 antibodies are described in, e.g., International Patent Publication Nos. WO 2008/091222 and WO 2008/0793326, and U.S. Patent Application Publication Nos. 2008/0014196, 2008/0175847, 2008/0181899, 2008/0107648, and 2010/0196385.

In some embodiments of the present invention, the DLL4 antagonists are polypeptides. The polypeptides can be recombinant polypeptides, natural polypeptides, or synthetic polypeptides that bind an epitope comprising amino acids within the extracellular domain of human DLL4. In some embodiments, the polypeptides comprise an antibody or fragment thereof that binds an epitope within the extracellular domain of human DLL4. It will be recognized by those of skill in the art that some amino acid sequences of a polypeptide can be varied without significant effect on the structure or function of the protein. Thus, the polypeptides further include variations of the polypeptides which show substantial binding activity to an epitope of the human DLL4 protein. In some embodiments, amino acid sequence variations of polypeptides include deletions, insertions, inversions, repeats, and/or type substitutions.

The polypeptides and variants thereof, can be further modified to contain additional chemical moieties not normally part of the polypeptide. The derivatized moieties can improve the solubility, the biological half-life, or the absorption of the polypeptide. The moieties can also reduce or eliminate any undesirable side effects of the polypeptides and variants. An overview for such chemical moieties can be found in *Remington: The Science and Practice of Pharmacy, 21st Edition*, 2005, University of the Sciences in Philadelphia, Pa.

The isolated polypeptides described herein can be produced by any suitable method known in the art. Such methods range from direct protein synthesis methods to constructing a DNA sequence encoding isolated polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and by selecting those codons that are favored in the host cell in which the recombinant polypeptide of interest will be produced. Standard methods can be applied to synthesize a polynucleotide sequence encoding a polypeptide of interest. For example, a complete amino acid sequence can be used to construct a back-translated gene. Further, a DNA oligomer containing a nucleotide sequence coding for the particular polypeptide can be synthesized. For example, several small oligonucleotides coding for portions of the desired polypeptide can be synthesized and then ligated. The individual oligonucleotides typically contain 5' and/or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the polypeptide in a desired host. Proper assembly can be confirmed by nucleotide sequencing, restriction mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding DLL4 antagonists such as polypeptides or antibodies, or fragments thereof. For example, recombinant expression vectors can be replicable DNA constructs which have synthetic or cDNA-derived DNA fragments encoding a polypeptide chain of an anti-DLL4 antibody, or fragment thereof, operatively linked to suitable transcriptional or translational regulatory elements derived from mammalian, microbial, viral, or insect genes. A transcriptional unit generally comprises an assembly of (1) a regulatory element or elements having a role in gene expression, for example, transcriptional promoters and/or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can also be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of an expression vector and control elements depends upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of a DLL4 antagonist polypeptide or antibody (or a DLL4 protein to use as an antigen) include prokaryotes, yeast, insect, or higher eukaryotic cells under the control of appropriate promoters. Prokaryotes include gram-negative or gram-positive organisms, for example, *E. coli* or Bacilli. Higher eukaryotic cells include established cell lines of mammalian origin as described below. Cell-free translation systems can also be employed.

Various mammalian or insect cell culture systems are used to express recombinant protein. Expression of recombinant proteins in mammalian cells may be preferred because such proteins are generally correctly folded, appropriately modified, and biologically functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived) cell lines, and HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are well-known to those of skill in the art (see, e.g., Luckow and Summers, 1988, *Bio/Technology*, 6:47).

The proteins produced by a transformed host can be purified according to any suitable method. Such methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence and glutathione-S-transferase can be attached to the protein to allow easy purification by passage over an appropriate affinity column. Isolated proteins can be physically characterized using such techniques as proteolysis, high performance liquid chromatography (HPLC), nuclear magnetic resonance (NMR), and x-ray crystallography.

For example, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reversed-phase HPLC steps employing hydrophobic RP-HPLC media, (e.g., silica gel having pendant methyl or other aliphatic groups), is employed to further purify a protein. Some or all of the foregoing purification steps, in various combinations, can be employed to provide a homogeneous recombinant protein.

In some embodiments, recombinant protein produced in bacterial culture is isolated, for example, by initial extraction from cell pellets, followed by one or more concentration, salting-out, aqueous ion exchange, or size exclusion chromatography steps. In certain embodiments, HPLC is employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Application Pub. Nos. 2008/0312425, 2009/0187005, and U.S. Pat. No. 7,691,980.

In certain embodiments, the DLL4 antagonist is a polypeptide that is not an antibody. A variety of methods for identifying and producing non-antibody polypeptides that bind with high affinity to a protein target are known in the art. See, e.g., Skerra, 2007, *Curr. Opin. Biotechnol.*, 18:295-304; Hosse et al., 2006, *Protein Science*, 15:14-27; Gill et al., 2006, *Curr. Opin. Biotechnol.*, 17:653-658; Nygren, 2008, *FEBS J.*, 275:2668-76; and Skerra, 2008, *FEBS J.*, 275:2677-83. In certain embodiments, phage display technology may be used to produce and/or identify a DLL4 antagonist polypeptide. In certain embodiments, the DLL4 antagonist polypeptide comprises a protein scaffold of a type selected from the group consisting of protein A, protein G, a lipocalin, a fibronectin domain, an ankyrin consensus repeat domain, and thioredoxin.

In certain embodiments, the DLL4 antagonists or antibodies can be used in any one of a number of conjugated (e.g., an immunoconjugate or radioconjugate) or non-conjugated forms. In certain embodiments, the antibodies are used in non-conjugated form to harness the subject's natural defense mechanisms including CDC and/or ADCC to eliminate malignant or cancerous cells.

In certain embodiments, the DLL4 antagonist (e.g., an antibody or polypeptide) is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is a enzymatically active toxin of bacterial, fungal, plant, or animal origin, or fragments thereof, including but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, Sapaonaria officinalis inhibitor, gelonin, restrictocin, phenomycin, enomycin, and the tricothecenes. In certain embodiments, the cytotoxic agent is a radioactive isotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re and $^{212}$Bi. Conjugates of an antibody and one or more small molecule toxins, such as a calicheamicin, maytansine, maytansinoids, a trichothene, and CC1065, and the derivatives of these toxins that have toxin activity, can also be used. Conjugates of an antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazoniumn derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents.

In some embodiments, the DLL4 antagonist is a non-protein molecule. In certain embodiments, the DLL4 antagonist is a small molecule.

In vivo and in vitro assays for determining whether an agent is a DLL4 antagonist are known in the art. In some embodiments, a cell-based, luciferase reporter assay utilizing a TCF/Luc reporter vector containing multiple copies of the TCF-binding domain upstream of a firefly luciferase reporter gene may be used to measure DLL4-induced Notch signaling levels in vitro. In other embodiments, a cell-based, luciferase reporter assay utilizing a CBF/Luc reporter vector containing multiple copies of the CBF-binding domain upstream of a firefly luciferase reporter gene may be used. The level of Notch activation induced by DLL4 in the presence of a DLL4 antagonist is compared to the level of Notch activation induced by DLL4 in the absence of the DLL4 antagonist. In some embodiments, the effect of a DLL4 antagonist on DLL4/Notch signaling can be assessed by measuring the effect of the agent on the expression level of one or more Notch pathway target genes.

III. METHODS OF USE AND PHARMACEUTICAL COMPOSITIONS

The present invention provides methods of treating diseases such as cancer with a DLL4 antagonist, while screening for, monitoring, preventing, and/or controlling side effects and/or toxicities, including, but not limited to cardiovascular side effects and/or toxicities associated with the DLL4 antagonist. Side effects and/or toxicities associated with cancer treatment may include, but are not limited to, fatigue, vomiting, nausea, diarrhea, pain, hair loss, neutropenia, anemia, thrombocytopenia, cardiovascular complications, and any combination thereof. Cardiovascular complications (e.g., cardiovascular side effects and/or toxicities) may be grouped into three main categories: 1) vascular conditions, 2) cardiac structural problems, and 3) cardiac dysfunction and heart failure. As used herein, "vascular conditions" include but are not limited to, atherosclerosis, hypertension, arterial thrombosis, vasculitis, and deep venous thrombosis/pulmonary embolus. As used herein, "cardiac structural problems" and "cardiac dysfunction and heart failure" include but are not limited to, valvular heart disease, pericardial effusion, pericardial constriction, angina, coronary artery disease, cardiomyopathy, myocardial ischemia, myocardial infarction (MI), arrhythmias, myocarditis, left ventricular dysfunction, heart failure, congestive heart failure (CHF), and combinations thereof. Cardiac structural problems, cardiac dysfunction, and heart failure directly impact the heart, while, generally, vascular conditions (e.g., hypertension) are a more systemic complication. As used herein, "cardiotoxicity" refers to cardiac structural problems, cardiac dysfunction, and heart failure. Thus, in some aspects and/or embodiments of the methods described herein, the screening for, monitoring, preventing, and/or controlling cardiovascular side effects and/or toxicities is screening for, monitoring, preventing, and/or controlling cardiotoxicity. Often cardiotoxicity is asymptomatic and/or early signs of cardiotoxicity are not evident with, for example, Doppler echocardiograms and/or with left ventricular ejection fraction (LVEF) monitoring.

Natriuretic peptides are produced by the heart and vasculature and include 4 identified types. A-type natriuretic peptide (ANP) is secreted largely by the atrial myocardium, B-type natriuretic peptide (BNP) is produced mainly by the ventricular myocardium, C-type natriuretic peptide (CNP) is produced by endothelial cells that line the blood vessels, and D-type natriuretic peptide has been isolated in plasma and atrial myocardium. The precursor prohormone of each natriuretic peptide is encoded by a separate gene. proBNP is a 108 amino acid peptide that is cleaved by the proteolytic enzyme furin into a 32 amino acid C-terminal peptide (BNP) and a 76 amino acid N-terminal peptide (NT-proBNP). proANP is a 126 amino acid peptide that is cleaved by the serine protease enzyme corin into a 28 amino acid C-terminal peptide (ANP) and a 98 amino acid N-terminal peptide (NT-proANP). Increases in the levels of natriuretic peptides have been used in the diagnosis of heart failure. Accordingly, in some embodiments, the present invention provides methods for using natriuretic peptide levels to monitor cardiotoxicity in subjects being treated with a DLL4 antagonist. In some embodiments, the methods use natriuretic peptide levels to monitor and/or detect acute cardiotoxicity. In some embodiments, monitoring the level of a natriuretic peptide gives an early indication of cardiotoxicity and/or congestive heart failure (CHF). In some embodiments, the methods detect cardiotoxicity prior to any evidence of cardiac dysfunction as evaluated by Doppler echocardiograms and/or with LVEF monitoring.

In certain embodiments, the cardiovascular side effects and/or toxicities that are detected, identified, monitored, reduced, prevented, attenuated, and/or screened for are cardiovascular side effects and/or toxicities caused by, associated with, and/or related to administration of a DLL4 antagonist or treatment with a DLL4 antagonist. In certain embodiments, the cardiovascular side effects and/or toxicities are related to the DLL4 antagonist.

In certain embodiments, the cardiovascular side effects and/or toxicities (e.g., side effect and/or toxicity related to treatment with a DLL4 antagonist) that is detected, identified, monitored, reduced, prevented, attenuated, and/or screened for in a method described herein does not include hypertension. In some embodiments the cardiovascular side effect and/or toxicity does not include a vascular condition. In certain embodiments, the cardiovascular side effect and/or toxicity that is detected, identified, monitored, reduced, prevented, attenuated, and/or screened for in a method described herein is a cardiotoxicity such as a cardiac structural problem, cardiac dysfunction, or heart failure. In certain embodiments, the cardiotoxicity is left ventricular dysfunction. In certain embodiments, the cardiotoxicity is congestive heart failure. In some embodiments, the cardiotoxicity is in an early or reversible stage of development.

The invention provides methods for selecting a subject for treatment with a DLL4 antagonist, comprising: determining the level of a biomarker in a sample, and selecting the subject for treatment with the DLL4 antagonist if the level of the biomarker is below a predetermined level. In some embodiments, the methods for selecting a subject for treatment with a DLL4 antagonist, comprise: obtaining a biological sample from the subject, determining the level of a biomarker in the sample, and selecting the subject for treatment with the DLL4 antagonist if the level of the biomarker is below a predetermined level. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP.

In some embodiments, the method of selecting a subject for treatment with a DLL4 antagonist comprises: obtaining a biological sample from the subject, determining the level of a natriuretic peptide in the sample, and selecting the subject for treatment with the DLL4 antagonist if the level of the natriuretic peptide is below a predetermined level. In some embodiments, the biological sample is blood, serum, or plasma. In some embodiments, the natriuretic peptide is B-type natriuretic peptide (BNP). Thus, in some embodiments, the methods of selecting a subject for treatment with a DLL4 antagonist, comprising: obtaining a biological sample from the subject, determining the level of BNP in the sample, and selecting the subject for treatment with the DLL4 antagonist if the level of BNP is below a predetermined level.

The invention also provides methods of identifying a subject as eligible for treatment with a DLL4 antagonist, comprising: determining the level of a biomarker in a sample, and identifying the subject as eligible for treatment with the DLL4 antagonist if the level of the biomarker is below a predetermined level. In some embodiments, the methods of identifying a subject as eligible for treatment with a DLL4 antagonist comprise: obtaining a biological sample from the subject, determining the level of a biomarker in the sample, and identifying the subject as eligible for treatment with the DLL4 antagonist if the level of the biomarker is below a predetermined level. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the methods of identifying a subject as eligible for treatment with a DLL4 antagonist comprise: obtaining a biological sample from the subject, determining the level of BNP in the sample, and identifying the subject as eligible for treatment with the DLL4 antagonist if the level of BNP is below a predetermined level.

The invention also provides methods of monitoring a subject receiving treatment with a DLL4 antagonist for the development of cardiovascular side effects and/or toxicity, comprising: determining the level of a biomarker in a sample, and comparing the level of the biomarker in the sample to a predetermined level of the biomarker, wherein an increase in the level of the biomarker indicates development of cardiovascular side effects and/or toxicity. In some embodiments, the methods of monitoring a subject receiving treatment with a DLL4 antagonist for the development of cardiovascular side effects and/or toxicity comprise: obtaining a biological sample from the subject receiving treatment, determining the level of a biomarker in the sample, and comparing the level of the biomarker in the sample to a predetermined level of the biomarker, wherein an increase in the level of the biomarker indicates development of cardiovascular side effects and/or toxicity. In some embodiments, the cardiovascular side effect and/or toxicity is cardiotoxicity. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP. In some embodiments, a method of monitoring a subject receiving treatment with a DLL4 antagonist for the development of cardiotoxicity, comprises: obtaining a biological sample from the subject receiving treatment, determining the level of BNP in the sample, and comparing the level of BNP in the sample to a predetermined level of BNP, wherein an increase in the level of BNP indicates development of cardiotoxicity.

The invention also provides methods of detecting the development of cardiovascular side effects and/or toxicity in a subject receiving treatment with a DLL4 antagonist, comprising: determining the level of a biomarker in a sample, and comparing the level of a biomarker in the sample to a predetermined level of the biomarker, wherein an increase in the level of the biomarker indicates development of cardiovascular side effects and/or toxicity. In some embodiments, the methods of detecting the development of cardiovascular side effects and/or toxicity in a subject receiving treatment with a DLL4 antagonist comprise: obtaining a biological sample from the subject receiving treatment, determining the level of a biomarker in the sample, and comparing the level of a biomarker in the sample to a predetermined level of the biomarker, wherein an increase in the level of the biomarker indicates development of cardiovascular side effects and/or toxicity. In some embodiments, the cardiovascular side effect and/or toxicity is cardiotoxicity. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP. In some embodiments, the methods of detecting the development of cardiotoxicity in a subject receiving treatment with a DLL4 antagonist comprise: obtaining a biological sample from the subject receiving treatment, determining the level of BNP in the sample, and comparing the level of BNP in the sample to a predetermined level of BNP, wherein an increase in the level of BNP indicates development of cardiotoxicity.

The invention also provides methods for identifying cardiovascular side effects and/or toxicity in a subject receiving treatment with a DLL4 antagonist, comprising: determining the level of a biomarker in a sample, and comparing the level of the biomarker in the sample to a predetermined level of the biomarker, wherein if the level of the biomarker in the sample is higher than the predetermined level of the biomarker then a cardiovascular side effect and/or toxicity is indicated. In some embodiments, the methods for identifying cardiovascular side effects and/or toxicity in a subject receiving treatment with a DLL4 antagonist comprise: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then a cardiovascular side effect and/or toxicity is indicated. In some embodiments, the cardiovascular side effect and/or toxicity is cardiotoxicity. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP. In some embodiments, a method for identifying cardiotoxicity in a subject receiving treatment with a DLL4 antagonist comprises: obtaining a biological sample from the subject receiving treatment, determining the level of BNP in the sample, and comparing the level of BNP in the sample to a predetermined level of BNP, wherein if the level of BNP in the sample is higher than the predetermined level of BNP then cardiotoxicity is indicated.

The invention also provides methods for monitoring cardiovascular side effects and/or toxicity in a subject receiving treatment with a DLL4 antagonist, comprising: determining the level of a biomarker in a sample, and comparing the level of the biomarker in the sample to a predetermined level of the biomarker, wherein if the level of the biomarker in the sample is higher than the predetermined level of the biomarker then cardiovascular side effects and/or toxicity is indicated. In some embodiments, the methods for monitoring cardiovascular side effects and/or toxicity in a subject receiving treatment with a DLL4 antagonist comprise: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then cardiovascular side effects and/or toxicity is indicated. In some embodiments, the cardiovascular side effect and/or toxicity is cardiotoxicity. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP. In some embodiments, a method for monitoring cardiotoxicity in a subject receiving treatment with a DLL4 antagonist comprises: obtaining a biological sample from the subject receiving treatment, determining the level of BNP in the sample, and comparing the level of BNP in the sample to a predetermined level of BNP, wherein if the level of BNP in the sample is higher than the predetermined level of BNP then cardiotoxicity is indicated.

The invention also provides methods of reducing cardiovascular side effects and/or toxicity in a subject receiving treatment with a DLL4 antagonist, comprising: determining the level of a biomarker in a sample from the subject, comparing the level of the biomarker in the sample to a predetermined level of the biomarker, and administering to the subject a therapeutically effective amount of a cardioprotective medication such as an ACE inhibitor and/or a β-blocker if the level of the biomarker in the sample is higher than the predetermined level of the biomarker. In some embodiments, the methods of reducing cardiovascular side effects and/or toxicity in a subject receiving treatment with a DLL4 antagonist comprise: obtaining a biological sample from the subject receiving treatment, determining the level of a biomarker in the sample, comparing the level of the biomarker in the sample to a predetermined level of the biomarker, and administering to the subject a therapeutically effective amount of a cardioprotective medication such as an ACE inhibitor and/or a β-blocker if the level of the biomarker in the sample is higher than the predetermined level of the biomarker. In some embodiments, the cardiovascular side effect and/or toxicity is cardiotoxicity. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP. In some embodiments, a method for reducing cardiotoxicity in a subject receiving treatment with a DLL4 antagonist comprises: obtaining a biological sample from the subject receiving treatment, determining the level of BNP in the sample, and comparing the level of BNP in the sample to a predetermined level of BNP, and administering to the subject a therapeutically effective amount of a cardioprotective medication such as an ACE inhibitor and/or a β-blocker if the level of BNP in the sample is higher than the predetermined level of BNP.

The invention also provides methods of preventing or attenuating the development of cardiovascular side effects and/or toxicity in a subject receiving treatment with a DLL4 antagonist, comprising: determining the level of a biomarker in a sample from the subject, comparing the level of the biomarker in the sample to a predetermined level of the biomarker; administering to the subject a therapeutically effective amount of a cardioprotective medication such as an ACE inhibitor and/or a β-blocker, and administering to the subject the DLL4 antagonist. In some embodiments, the methods of preventing or attenuating the development of cardiovascular side effects and/or toxicity in a subject receiving treatment with a DLL4 antagonist comprise: obtaining a biological sample from the subject prior to treatment with the DLL4 antagonist, determining the level of a biomarker in the sample, comparing the level of the biomarker in the sample to a predetermined level of the biomarker; administering to the subject a therapeutically effective amount of a cardioprotective medication such as an ACE inhibitor and/or a β-blocker, and administering to the subject the DLL4 antagonist. In some embodiments, the cardiovascular side effect and/or toxicity is cardiotoxicity. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP, NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP. In some embodiments, a method of preventing or attenuating the development of cardiotoxicity in a subject receiving treatment with a DLL4 antagonist comprises: obtaining a biological sample from the subject prior to treatment with the DLL4 antagonist, determining the level of BNP in the sample, comparing the level of BNP in the sample to a predetermined level of BNP; administering to the subject a therapeutically effective amount of a cardioprotective medication such as an ACE inhibitor and/or a β-blocker if the level of BNP in the sample is higher than the predetermined level of BNP; and administering to the subject the DLL4 antagonist.

In some embodiments of the methods described herein, the predetermined level is about 300 pg/ml or less in a blood, serum, or plasma sample. In some embodiments, the predetermined level is about 200 pg/ml or less in a blood, serum, or plasma sample. In some embodiments, the predetermined level is about 250 pg/ml or less in a blood, serum, or plasma sample. In some embodiments, the predetermined level is about 200 pg/ml or less in a blood, serum, or plasma sample. In some embodiments, the predetermined level is about 150 pg/ml or less in a blood, serum, or plasma sample. In some embodiments, the predetermined level is about 100 pg/ml or less in a blood, serum, or plasma sample. In the context of predetermined levels of BNP, the term "about" means the referenced amount plus or minus 10% of that referenced amount.

In some embodiments, the predetermined level of a biomarker (e.g., natriuretic peptide or BNP) is the amount of the biomarker in a sample obtained at an earlier date. In some embodiments, the predetermined level of a biomarker (e.g., natriuretic peptide or BNP) is the amount of the biomarker in a sample obtained prior to treatment. In some embodiments, the predetermined level of a biomarker (e.g., natriuretic peptide or BNP) is a normal reference level. In some embodiments, the predetermined level for BNP is about 100 pg/ml or less in blood, serum, or plasma. In some embodiments, the normal reference level for BNP is about 100 pg/ml or less in blood, serum, or plasma.

In any of the methods described herein, a biological sample is obtained approximately every week, every 2 weeks, every 3 weeks, or every 4 weeks.

In some embodiments, if the BNP level in the sample is above a predetermined level for two consecutive samples, the subject is administered a therapeutically effective amount of a cardioprotective medication such as an ACE inhibitor and/or a β-blocker. In some embodiments, if the BNP level in the biological sample is above 100 pg/ml for two consecutive samples, the subject is administered a therapeutically effective amount of a cardioprotective medication such as an ACE inhibitor and/or a β-blocker. In some embodiments of the methods described herein, if the BNP level in the biological sample is above a predetermined level for any one sample, the subject is administered a therapeutically effective amount of a cardioprotective medication such as an ACE inhibitor and/or β-blocker. In some embodiments of the methods described herein, if the BNP level in the biological sample is above 200 pg/ml for any one sample, the subject is administered a therapeutically effective amount of a cardioprotective medication such as an ACE inhibitor and/or a β-blocker. In some embodiments of the methods described herein, if the BNP level in the biological sample is above a predetermined level for any one sample, the subject is administered a therapeutically effective amount of a cardioprotective medication such as an ACE inhibitor and/or a β-blocker and the DLL4 antagonist is withheld. In some embodiments of the methods described herein, if the BNP level in the biological sample is above 300 pg/ml for any one sample, the subject is administered a therapeutically effective amount of a cardioprotective medication such as an ACE inhibitor and/or a β-blocker and the DLL4 antagonist is withheld. In some embodiments, if the BNP level decreases to below 200 pg/ml after administration of an ACE inhibitor and/or a β-blocker, then administration of the DLL4 antagonist is resumed.

In some embodiments of any of the methods described herein, the subjects are evaluated by LVEF monitoring. The LVEF represents the volumetric fraction of blood pumped out of the left ventricle of the heart with each heart beat or cardiac cycle. Generally a normal range for LVEF is 55-70%, and a significantly reduced ejection fraction typically indicates a cardiac dysfunction and/or heart failure. In some embodiments, cardiovascular dysfunction and/or cardiotoxicity is indicated if the LVEF is less than about 60%. In some embodiments, cardiovascular dysfunction and/or cardiotoxicity is indicated if the LVEF is less than about 55%. In some embodiments, cardiovascular dysfunction and/or cardiotoxicity is indicated if the LVEF is less than about 50%. In some embodiments, cardiovascular dysfunction and/or cardiotoxicity is indicated if there is a 10% or greater decline in LVEF. In some embodiments, cardiovascular dysfunction and/or cardiotoxicity is indicated if there is a 20% or greater decline in LVEF. In some embodiments, cardiovascular dysfunction and/or cardiotoxicity is indicated if there is a 20% or greater decline in LVEF to a value greater than 50%. In some embodiments, cardiovascular dysfunction and/or cardiotoxicity is indicated if there is a 10% or greater decline in LVEF to a value less than 50%.

In some embodiments of any of the methods described herein, the subjects are evaluated using a Doppler echocardiogram. Doppler echocardiography is a method for detecting the direction and velocity of moving blood within the heart and can be used to detect pulmonary hypertension. Pulmonary hypertension is high blood pressure that occurs in the arteries in the lungs. It is a different measurement altogether from systemic blood pressure and what is generally called "high blood pressure" or "hypertension". In some embodiments, cardiovascular dysfunction and/or cardiotoxicity is indicated if the subject has a peak tricuspid velocity (PTV) greater than 3.4 m/s on Doppler echocardiogram. In some embodiments, cardiovascular dysfunction and/or cardiotoxicity is indicated if the subject has a peak tricuspid velocity (PTV) greater than 3.4 m/s on Doppler echocardiogram that persists for more than 4 weeks. In some embodiments, cardiovascular dysfunction and/or cardiotoxicity is indicated if the subject has a peak tricuspid velocity (PTV) greater than 3.4 m/s on Doppler echocardiogram that persists for more than 8 weeks.

The invention also provides methods of ameliorating cardiotoxicity in a subject administered a DLL4 antagonist, comprising: administering to the subject a therapeutically effective amount of a cardioprotective medication such as an ACE inhibitor and/or a β-blocker. As described herein, the cardiotoxicity is not systemic hypertension (i.e., high blood pressure).

The invention also provides methods of screening a subject for the risk of cardiovascular side effects and/or toxicity from treatment with a DLL4 antagonist, comprising: determining the level of a biomarker in a sample from the subject, and comparing the level of the biomarker in the sample to a predetermined level of the biomarker, wherein if the level of the biomarker in the sample is higher than the predetermined level of the biomarker then the subject is at risk for cardiovascular side effects and/or toxicity. In some embodiments, the methods of screening a subject for the risk of cardiovascular side effects and/or toxicity from treatment with a DLL4 antagonist comprise: obtaining a biological sample from the subject prior to treatment with the DLL4 antagonist, determining the level of a biomarker in the sample, and comparing the level of the biomarker in the sample to a predetermined level of the biomarker, wherein if the level of the biomarker in the sample is higher than the predetermined level of the biomarker then the subject is at risk for cardiovascular side effects and/or toxicity. In some embodiments, the cardiovascular side effect and/or toxicity is cardiotoxicity. In some embodiments, the biomarker is a natriuretic peptide. In some embodiments, the natriuretic peptide is an atrial natriuretic peptide (ANP)-type peptides, a brain natriuretic peptide (BNP)-type peptides, or variants thereof. ANP-type peptides include pre-proANP, proANP. NT-proANP, and ANP. BNP-type peptides include pre-proBNP, proBNP, NT-proBNP, and BNP. In some embodiments, the natriuretic peptide is BNP. In some embodiments, the natriuretic peptide is NT-proBNP. In some embodiments, the natriuretic peptide is ANP. In some embodiments, a method of screening a subject for the risk of cardiotoxicity from treatment with a DLL4 antagonist comprises: obtaining a biological sample from the subject prior to treatment with the DLL4 antagonist, determining the level of BNP in the sample, and comparing the level of BNP in the sample to a predetermined level of BNP, wherein if the level of BNP in the sample is higher than the predetermined level of BNP then the subject is at risk for cardiotoxicity. In some embodiments, the predetermined level of BNP is about 100 pg/ml. In some embodiments, if the subject is at risk for cardiotoxicity, the subject is administered a therapeutically effective amount of a cardioprotective medication such as an ACE inhibitor and/or a β-blocker prior to treatment with the DLL4 antagonist.

In some embodiments of the methods described herein, the ACE inhibitor is selected from the group consisting of: captopril, zofenopril, enalapril, ramipril, quinapril, perindopril, lisinopril, benazepril, fosinopril, ceronapril, casokinins, lactokinins, teprotide, alacepril, cilazapril, delapril, imidapril, moexipril, rentiapril, spirapril, temocapril, moveltipril, and trandolapril.

In some embodiments of the methods described herein, the β-blocker is selected from the group consisting of: carvedilol, atenolol, metoprolol, nadolol, oxprenolol, pindolol, propranolol, timolol, acebutolol, bisoprolol, esmolol, labetalol, bucindolol, nebivolol, alprenolol; amosulalol, arotinolol, befunolol, betaxolol, bevantolot, bopindolol, bucumolol, bufetolol, bufuralol, bunitrolol, bupranolol, butidrine hydrochloride, butofilolol, carazolol, carteolol, celiprolol, cetamolol, cloranololdilevalol, epanolol, indenolol, levobunolol, mepindolol, metipranolol, moprolol, nadoxolol, nipradilol, penbutolol, practolol, pronethalol, sotalol, sulfinalol, talinolol, tertatolol, tilisolol, toliprolol, and xibenolol. In some embodiments, the β-blocker is carvedilol.

In any of the methods described herein, the DLL4 antagonist specifically binds human DLL4. In some embodiments, the DLL4 antagonist is an antibody that specifically binds the extracellular domain of human DLL4. In some embodiments, the DLL4 antagonist specifically binds an epitope within amino acids 27-217 of the extracellular domain of human DLL4 (SEQ ID NO:17). In some embodiments, the DLL4 antagonist binds an epitope comprising amino acids 66-73 (QAVVSPGP, SEQ ID NO: 18) of human DLL4. In some embodiments, the DLL4 antagonist binds an epitope comprising amino acids 139-146 (LISKIAIQ, SEQ ID NO:19) of human DLL4. In some embodiments, the DLL4 antagonist binds an epitope comprising amino acids 66-73 (QAVVSPGP, SEQ ID NO:18) and amino acids 139-146

(LISKIAIQ, SEQ ID NO:19) of human DLL4. In some embodiments, the DLL4 antagonist binds human DLL4 with a dissociation constant ($K_D$) of about 10 nM to about 0.1 nM.

In certain embodiments, the DLL4 antagonist is an anti-DLL4 antibody. In certain embodiments, the DLL4 antagonist is an antibody comprising a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5), and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In certain embodiments, the DLL4 antagonist is an antibody comprising a heavy chain variable region comprising the amino acids of SEQ ID NO: 10. In certain embodiments, the DLL4 antagonist is an antibody which further comprises a light chain variable region comprising the amino acids of SEQ ID NO: 12. In certain embodiments, the DLL4 antagonist comprises the same heavy and light chain amino acid sequences as an antibody encoded by a plasmid deposited with ATCC having deposit no. PTA-8425 or PTA-8427. In certain embodiments, the DLL4 antagonist comprises the heavy chain CDR amino acid sequences and the light chain CDR amino acid sequences that are contained in the 21M18 antibody produced by the hybridoma deposited with ATCC having deposit no. PTA-8670. In certain embodiments, the DLL4 antagonist is encoded by the plasmid having ATCC deposit no. PTA-8425 which was deposited with American Type Culture Collection (ATCC), at 10801 University Boulevard, Manassas, Va., 20110, under the conditions of the Budapest Treaty on May 10, 2007. In certain embodiments, the DLL4 antagonist is encoded by the plasmid having ATCC deposit no. PTA-8427 which was deposited with American Type Culture Collection (ATCC), at 10801 University Boulevard, Manassas, Va. 20110, under the conditions of the Budapest Treaty on May 10, 2007. In some embodiments, the DLL4 antagonist is the antibody produced by the hybridoma having ATCC deposit no. PTA-8670 which was deposited with the ATCC under the conditions of the Budapest Treaty on Sep. 28, 2007. In some embodiments, the DLL4 antagonist is a humanized version of the antibody produced by the hybridoma having ATCC deposit no. PTA-8670. In certain embodiments, the DLL4 antagonist competes for specific binding to human DLL4 with an antibody encoded by the plasmid deposited with ATCC having deposit no. PTA-8425 or PTA-8427.

In some embodiments, the subject has cancer. In some embodiments, the cancer is selected from the group consisting of: lung cancer, breast cancer, colon cancer, colorectal cancer, melanoma, pancreatic cancer, gastrointestinal cancer, renal cancer, ovarian cancer, liver cancer, endometrial cancer, kidney cancer, prostate cancer, thyroid cancer, neuroendocrine cancer, neuroblastoma, glioma, glioblastoma multiforme, cervical cancer, stomach cancer, bladder cancer, hepatoma, and head and neck cancer. In certain embodiments, the cancer is a hematological cancer, such as a lymphoma or leukemia. In certain embodiments, the cancer is non-small cell lung cancer (NSCLC). In certain embodiments, the cancer is ovarian cancer. In certain embodiments, the cancer is pancreatic cancer.

In some embodiments, the biological sample is a body fluid. In some embodiments, the biological sample is blood, plasma, serum, or urine. In some embodiments, the biological sample is a venous whole blood specimen. In some embodiments, the biological sample is a venous whole blood specimen using EDTA as an anticoagulant. In some embodiments, the biological sample is a plasma specimen. In some embodiments, the biological sample is a plasma specimen using EDTA as an anticoagulant. Samples of body fluids may be obtained by any method known in the art. In some embodiments, the biological sample is a frozen tissue sample or is fresh tissue sample.

Assays for measuring or determining the level of a natriuretic peptide (e.g., NT-proBNP or BNP) in a sample are known to those of skilled in the art. For example, in some embodiments a fluorescent immunoassay that quantitatively measures BNP levels in whole blood or plasma specimens is used. In some embodiments, the sample contains EDTA as an anticoagulant. In some embodiments, the test is performed at the bedside. In some embodiments, a sample is placed in a test device and the sample moves by capillary action into a reaction chamber containing murine fluorescent antibodies to BNP. The reaction mixture then flows through an elution column. Analyte and fluorescent antibody-BNP conjugates are captured in discrete zones along the column. Bound fluorescent material represents the serum BNP concentration. After about 15 minutes, the test device is placed in an immunofluorescence reader and the BNP concentration is determined. BNP levels less than or equal to 100 pg/ml are considered representative of normal values in patients without congestive heart failure (CHF) by those skilled in the art. BNP levels above 100 pg/ml to 300 ug/ml are suggestive of heart failure, BNP levels above 300 pg/ml indicate mild heart failure, BNP levels above 600 pg/ml indicate moderate heart failure, and BNP levels above 900 pg/ml indicate severe heart failure.

In some embodiments, the DLL4 antagonist is administered as an initial dose of about 2.5 mg/kg. For example, antibody OMP-21M18 is diluted with 5% dextrose in water (USP) to a total volume of 250 mL. The OMP-21M18 is delivered through a 0.22-micron filter over 30 minutes as an intravenous infusion. In some embodiments, subsequent doses are administered in a similar manner.

In another aspect of the invention, the methods described herein may further comprise administering one or more additional therapeutic agents. An additional therapeutic agent can be administered prior to, concurrently with, and/or subsequently to, administration of the DLL4 antagonist. Pharmaceutical compositions comprising a DLL4 antagonist and an additional therapeutic agent(s) are also provided. In some embodiments, the one or more additional therapeutic agents comprise 1, 2, 3, or more additional therapeutic agents.

Combination therapy with at least two therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing side effects and/or toxicities. Combination therapy may increase the therapeutic index of one or both of the therapeutic agents. Combination therapy may decrease the likelihood that resistant cancer cells will develop. In some embodiments, combination therapy comprises a therapeutic agent that primarily affects (e.g. inhibits or kills) non-tumorigenic cells and a therapeutic agent that primarily affects (e.g., inhibits or kills) tumorigenic CSCs.

It will be appreciated that the combination of a DLL4 antagonist and an additional therapeutic agent may be administered in any order or concurrently. In some embodiments, the DLL4 antagonist is administered to subjects that have previously undergone treatment with a second therapeutic agent. In certain other embodiments, the DLL4 antagonist and a second therapeutic agent is administered substantially simultaneously or concurrently. For example, a subject may be given a DLL4 antagonist (e.g., an antibody) while undergoing a course of treatment with a second therapeutic agent (e.g., chemotherapy). In certain embodiments, a DLL4 antagonist is administered within 1 year of the treatment with a second therapeutic agent. In certain alternative embodiments, a DLL4 antagonist is administered within 10, 8, 6, 4, or 2 months of any treatment with a second therapeutic agent. In certain other embodiments, a DLL4 antagonist is administered within 4, 3, 2, or 1 weeks of any treatment with a second therapeutic agent. In some embodiments, a DLL4 antagonist is administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the subject either has to stop therapy, or if possible, suffer from the unpleasant side effects associated with the therapeutic agent.

Side effects from therapeutic agents may include, but are not limited to, hives, skin rashes, itching, nausea, vomiting, decreased appetite, diarrhea, chills, fever, fatigue, muscle aches and pain, headaches, low blood pressure, high blood pressure, hypokalemia, low blood counts, bleeding, and cardiac problems.

Thus, in some embodiments, the methods described herein include using an intermittent dosing regimen, which may reduce side effects and/or toxicities associated with administration of a DLL4 antagonist. As used herein, "intermittent dosing" refers to a dosing regimen using a dosing interval of more than once a week, e.g., dosing once every 2 weeks, once every 3 weeks, once every 4 weeks, etc. In some embodiments, a method for treating a subject comprises administering to the subject an effective dose of a DLL4 antagonist (e.g. an anti-DLL4 antibody) according to an intermittent dosing regimen. In some embodiments, the method comprises administering to the subject an effective dose of a DLL4 antagonist (e.g., an anti-DLL4 antibody) according to an intermittent dosing regimen, and increasing the therapeutic index of the DLL4 antagonist. In some embodiments, the intermittent dosing regimen comprises administering an initial dose of a DLL4 antagonist to the subject, and administering subsequent doses of the DLL4 antagonist about once every 2 weeks. In some embodiments, the intermittent dosing regimen comprises administering an initial dose of a DLL4 antagonist to the subject, and administering subsequent doses of the DLL4 antagonist about once every 3 weeks. In some embodiments, the intermittent dosing regimen comprises administering an initial dose of a DLL4 antagonist to the subject, and administering subsequent doses of the DLL4 antagonist about once every 4 weeks.

In some embodiments, the subsequent doses in an intermittent dosing regimen are about the same amount or less than the initial dose. In other embodiments, the subsequent doses are a greater amount than the initial dose. As is known by those of skill in the art, doses used will vary depending on the clinical goals to be achieved. In some embodiments, the initial dose is about 0.25 mg/kg to about 20 mg/kg. In some embodiments, the initial dose is about 0.25, 0.5, 1, 2, 3, 4, 5, 6, 7, 8, 9, 10, 11, 12, 13, 14, 15, 16, 17, 18, 19, or 20 mg/kg. In certain embodiments, the initial dose is about 0.5 mg/kg. In certain embodiments, the initial dose is about 1 mg/kg. In certain embodiments, the initial dose is about 2.5 mg/kg. In certain embodiments, the initial dose is about 5 mg/kg. In certain embodiments, the initial dose is about 7.5 mg/kg. In certain embodiments, the initial dose is about 10 mg/kg. In certain embodiments, the initial dose is about 12.5 mg/kg. In certain embodiments, the initial dose is about 15 mg/kg. In certain embodiments, the initial dose is about 20 mg/kg. In some embodiments, the subsequent doses are about 0.25 mg/kg to about 15 mg/kg. In certain embodiments, the subsequent doses are about 0.5, 1, 2, 3, 4, 5, 6, 7, 8, 9, 10, 11, 12, 13, 14 or 15 mg/kg. In certain embodiments, the subsequent doses are about 0.5 mg/kg. In certain embodiments, the subsequent doses are about 1 mg/kg. In certain embodiments, the subsequent doses are about 2.5 mg/kg. In certain embodiments, the subsequent doses are about 5 mg/kg. In some embodiments, the subsequent doses are about 7.5 mg/kg. In some embodiments, the subsequent doses are about 10 mg/kg. In some embodiments, the subsequent doses are about 12.5 mg/kg.

In some embodiments, the intermittent dosing regimen comprises: (a) administering to the subject an initial dose of a DLL4 antagonist of about 2.5 mg/kg and (b) administering subsequent doses of about 2.5 mg/kg once every 2 weeks. In some embodiments, the intermittent dosing regimen comprises: (a) administering to the subject an initial dose of a DLL4 antagonist of about 5 mg/kg and (b) administering subsequent doses of about 5 mg/kg once every 2 weeks. In some embodiments, the intermittent dosing regimen comprises: (a) administering to the subject an initial dose of a DLL4 antagonist of about 2.5 mg/kg and (b) administering subsequent doses of about 2.5 mg/kg once every 3 weeks. In some embodiments, the intermittent dosing regimen comprises: (a) administering to the subject an initial dose of a DLL4 antagonist of about 5 mg/kg and (b) administering subsequent doses of about 5 mg/kg once every 3 weeks. In some embodiments, the intermittent dosing regimen comprises: (a) administering to the subject an initial dose of a DLL4 antagonist of about 2.5 mg/kg and (b) administering subsequent doses of about 2.5 mg/kg once every 4 weeks. In some embodiments, the intermittent dosing regimen comprises: (a) administering to the subject an initial dose of a DLL4 antagonist of about 5 mg/kg and (b) administering subsequent doses of about 5 mg/kg once every 4 weeks. In certain embodiments, the initial dose and the maintenance doses are different, for example, the initial dose is about 5 mg/kg and the subsequent doses are about 2.5 mg/kg. In certain embodiments, an intermittent dosing regimen may comprise a loading dose, for example, the initial dose is about 20 mg/kg and the subsequent doses are about 2.5 mg/kg or about 5 mg/kg administered once every 2 weeks, once every 3 weeks, or once every 4 weeks.

Another aspect of the present invention is directed to methods for reducing toxicity of a DLL4 antagonist in a human subject comprises administering to the subject the DLL4 antagonist using an intermittent dosing regimen. Another aspect of the present invention is directed to methods for reducing side effects of a DLL4 antagonist in a human subject comprises administering to the subject the DLL4 antagonist using an intermittent dosing regimen. Another aspect of the present invention is directed to methods for increasing the therapeutic index of a DLL4 antagonist in a human subject comprises administering to the subject the DLL4 antagonist using an intermittent dosing regimen.

The choice of delivery method for the initial and subsequent doses is made according to the ability of the subject to tolerate introduction of the DLL4 antagonist into the body. Thus, in any of the aspects and/or embodiments described herein, the administration of the DLL4 antagonist may be by intravenous injection or intravenously. In some embodiments, the administration is by intravenous infusion. In any of the aspects and/or embodiments described herein, the administration of the DLL4 antagonist may be by a non-intravenous route.

Therapeutic agents that may be administered in combination with the DLL4 antagonist include chemotherapeutic agents. Thus, in some embodiments, the method or treatment involves the administration of a DLL4 antagonist of the present invention in combination with a chemotherapeutic agent or cocktail of multiple different chemotherapeutic agents. Treatment with a DLL4 antagonist (e.g., an antibody) can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book*, 4th Edition, 2008, M. C. Perry, Editor, Lippincott, Williams & Wilkins, Philadelphia, Pa.

Chemotherapeutic agents useful in the instant invention include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2''-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylomithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including, for example, tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin. In certain embodiments, the additional therapeutic agent is paclitaxel. In certain embodiments, where the chemotherapeutic agent administered in combination with a DLL4 antagonist is carboplatin, the cancer or tumor being treated is lung cancer or a lung tumor.

In certain embodiments, the chemotherapeutic agent is a topoisomerase inhibitor. Topoisomerase inhibitors are chemotherapeutic agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In certain embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine. In some embodiments, the additional therapeutic agent is pemetrexed. In certain embodiments, where the chemotherapeutic agent administered in combination with a DLL4 antagonist is gemcitabine, the cancer or tumor being treated is pancreatic cancer or a pancreatic tumor. In certain embodiments, where the chemotherapeutic agent administered in combination with a DLL4 antagonist is pemetrexed, the cancer or tumor being treated is lung cancer or a lung tumor. In some embodiments, the DLL4 antagonist is administered in combination with pemetrexed and carboplatin.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, where the chemotherapeutic agent administered in combination with a DLL4 antagonist is an anti-mitotic agent, the cancer or tumor being treated is breast cancer or a breast tumor.

In some embodiments, an additional therapeutic agent comprises an agent such as a small molecule. For example, treatment can involve the combined administration of a DLL4 antagonist (e.g. an antibody) of the present invention with a small molecule that acts as an inhibitor against additional tumor-associated proteins including, but not limited to, EGFR, ErbB2, HER2, and/or VEGF. In certain embodiments, the additional therapeutic agent is a small molecule that inhibits a cancer stem cell pathway. In some embodiments, the additional therapeutic agent is a small molecule inhibitor of the Notch pathway. In some embodiments, the additional therapeutic agent is a small molecule inhibitor of the Wnt pathway. In some embodiments, the additional therapeutic agent is a small molecule inhibitor of the BMP pathway. In some embodiments, the additional therapeutic agent is a small molecule that inhibits β-catenin signaling.

In some embodiments, an additional therapeutic agent comprises a biological molecule, such as an antibody. For example, treatment can involve the combined administration of a DLL4 antagonist (e.g. an antibody) of the present invention with other antibodies against additional tumor-associated proteins including, but not limited to, antibodies that bind EGFR, ErbB2, HER2, and/or VEGF. In certain embodiments, the additional therapeutic agent is an antibody that is an anti-cancer stem cell marker antibody. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an antibody inhibitor of the Notch pathway. In some embodiments, the additional therapeutic agent is an antibody inhibitor of the Wnt pathway. In some embodiments, the additional therapeutic agent is an antibody inhibitor of the BMP pathway. In some embodiments, the additional therapeutic agent is an antibody that inhibits β-catenin signaling. In certain embodiments, the additional therapeutic agent is an antibody that is an angiogenesis inhibitor or modulator (e.g., an anti-VEGF or VEGF receptor antibody). In certain embodiments, the additional therapeutic agent is bevacizumab (AVASTIN), trastuzumab (HERCEPTIN), panitumumab (VECTIBIX), or cetuximab (ERBITUX). Combined administration can include co-administration, either in a single pharmaceutical formulation or using separate formulations, or consecutive administration in either order but generally within a time period such that all active agents can exert their biological activities simultaneously.

Furthermore, treatment with a DLL4 antagonist described herein can include combination treatment with other biologic molecules, such as one or more cytokines (e.g., lymphokines, interleukins, tumor necrosis factors, and/or growth factors) or can be accompanied by surgical removal of tumors, cancer cells, or any other therapy deemed necessary by a treating physician.

In certain embodiments, the treatment involves the administration of a DLL4 antagonist (e.g. an antibody) of the present invention in combination with radiation therapy. Treatment with a DLL4 antagonist can occur prior to, concurrently with, or subsequent to administration of radiation therapy. Dosing schedules for such radiation therapy can be determined by the skilled medical practitioner.

Embodiments of the present disclosure can be further defined by reference to the following non-limiting examples, which describe the use of a DLL4 antagonist for treatment of cancer. It will be apparent to those skilled in the art that many modifications, both to materials and methods, may be practiced without departing from the scope of the present disclosure.

EXAMPLES

Example 1

Phase 1 Study of OMP-21M18 in Subjects with Previously Treated Solid Tumors

The study was an open-label Phase 1 dose-escalation study of OMP-21M18 in subjects with advanced solid tumors. The primary objective of the study was to determine the maximum tolerated dose of OMP-21M18. The secondary objectives were to determine the safety, the rate of immunogenicity, the preliminary efficacy, and the pharmacokinetics of OMP-21M18.

The subjects in the initial portion of the trial were treated at dose levels of 0.5 (n=3), 1.0 (n=3), 2.5 (n=6), and 5.0 mg/kg (n=3) once a week for nine doses and then every other week; 2.5 (n=6), 5 (n=6) and 10 mg/kg (n=12) once every other week; and 10 mg/kg on Days 0, 7, and 14 as a loading dose and then once every other week. In the expansion portion of the study, 15 additional subjects were treated with 10 mg/kg once every other week. Cohorts of 3 subjects were treated and evaluated for dose-limiting toxicities (DLTs) through Day 28. If 0 of 3 subjects had a DLT, escalation to the next dose cohort occurred. If 1 of 3 subjects had a DLT, 3 additional subjects were treated and escalation to the next cohort occurred if less than 2 of 6 subjects experienced a DLT. Subjects continued on treatment until Day 56, when an assessment of the tumor respond was performed.

The maximum tolerated dose was not reached at a dose of 10 mg/kg every other week, however several subjects treated with 10 mg/kg every other week for longer than 100 days showed signs of cardiotoxicity that exceeded the level of acceptable chronic toxicity and enrollment in the study was stopped early.

During the conduct of the Phase 1 study, cardiotoxicity was identified as a potential toxicity in an ongoing monkey study. Based on the initial Phase 1 study results and the monkey study results, the Phase 1 study protocol was amended to include monitoring for cardiac dysfunction and/or cardiotoxicity with BNP measurements and echocardiograms. As discussed herein, BNP (or NT-proBNP) levels in blood/serum samples may be used to detect cardiac dysfunction and/or heart failure. Increases in BNP levels to greater than 400 pg/ml or NT-proBNP levels to greater than 800 pg/ml considered to be possibly related to OMP-21M18 treatment were observed in six patients who received 10 mg/kg once every other week. Five of the patients who received 10 mg/kg once every other week had LVEF declines as evaluated by echocardiograms and four of these patients developed congestive heart failure. OMP-21M18 treatment was discontinued for all four patients and they were administered medications for heart failure. The symptoms of heart failure subsequently diminished in all subjects. No instances of significant increases in BNP levels or other signs of cardiotoxicity were observed in the lower dose cohorts, except for one patient who received 2.5 mg/kg once every other week and developed pulmonary hypertension.

Example 2

Phase 1b Study of OMP-21M18 in Combination with Carboplatin and Pemetrexed in Subjects with NSCLC The study is a Phase 1b dose-escalation study of OMP-21M18 plus carboplatin and pemetrexed (carbo/PEM) in subjects with unresectable, locally advanced, recurrent, or metastatic non-squamous non-small cell lung cancer (NSCLC). Subjects had not received prior chemotherapy for the cancer. The primary objective of the study was to determine the maximum tolerated dose of OMP-21M18 plus carbo/PEM in subjects with NSCLC. The secondary objectives were to determine the safety, the rate of immunogenicity, the preliminary efficacy, and the pharmacokinetics of OMP-21M18 in combination with carbo/PEM as a first line treatment in subjects with NSCLC.

Carboplatin (6 mg/ml×min×[creatinine clearance (ml/min)+25]) and pemetrexed (500 mg/m$^2$) were administered once every 21 days for a total of 6 cycles (or for less than 6 full cycles if toxicity necessitates reducing or holding a dose or terminating treatment). Patients with stable disease or a response at the end of the 6 cycles continued to receive OMP-21M18 once every 3 weeks as maintenance therapy. OMP-21M18 was supplied at a concentration of 10 mg/ml in a 25-ml single-use glass vial filled to 20 ml to deliver a total of 200 mg per vial. OMP-21M18 was administered by intravenous (IV) infusion over 30 minutes once every 21 days (on the same day as the scheduled carbo/PEM administration) until disease progression.

Patient demographics are summarized in Table 1.

TABLE 1

| | Dose Cohort (mg/kg Q3W) | | | |
| --- | --- | --- | --- | --- |
| | 5* | 2.5 | 5 | Total |
| No. of patients | 6 | 6 | 8 | 20 |
| Median age (years) | 66.5 | 59.5 | 65.0 | 64.0 |
| Male/Female | 2/4 | 2/4 | 2/6 | 6/14 |
| Prior Surgery | 0 | 0 | 1 | 1 |
| Prior Neoadjuvant/Adjuvant Therapy | 0 | 0 | 0 | 0 |
| Prior Radiotherapy | 2 | 1 | 5 | 8 |

*Prior to risk mitigation

The first cohort of 6 patients was administered OMP-21M18 at a dosage of 5 mg/kg once every 3 weeks. Treatment in this cohort was paused due to emerging evidence of cardiotoxicity secondary to administration of OMP-21M18 in other ongoing studies (see Example 1). The Phase 1b protocol was amended to include a risk mitigation plan to enhance the therapeutic index of OMP-21M18 and manage tolerability. The second cohort of six patients was administered OMP-21M18 at a dosage of 2.5 mg/kg once every 3 weeks and the third cohort of eight patients was administered OMP-21M18 at a dosage of 5 mg/kg once every 3 weeks. As part of the safety evaluation and risk mitigation, subjects were monitored for B-type natriuretic peptide (BNP) levels in blood/serum samples every 14 days using an Alere Triage BNP test and device. Patients were administered a cardioprotective ACE inhibitor and/or carvedilol if their BNP levels were greater than or equal to 100 pg/ml in two consecutive samples or greater than or equal to 200 pg/ml in one sample, while still receiving OMP-21M18. Patients were administered an ACE inhibitor or carvedilol if their BNP level was greater than or equal to 300 pg/ml in any one sample and treatment with OMP-21M18 was withheld. Treatment with OMP-21M18 was restarted when BNP levels decreased below 300 pg/ml. If a subject's BNP level was greater than 400 pg/ml in any one sample, treatment with OMP-21M18 was discontinued. In addition, subjects had Doppler echocardiograms every 28 days to assess cardiac function and monitor left ventricular ejection fraction (LVEF) and peak tricuspid velocity (PTV). Baseline BNP and echocardiogram readings were taken just prior to administration of the first dosage.

During the study, subjects were assessed for adverse events from the time of enrollment through 30 days after the last dose of OMP-21M18. Adverse events were assessed using the National Cancer Institute (NCI) Common Terminology Criteria for Adverse Events (CTCAE), version 4.02.

In the first cohort (OMP-21M18 5 mg/kg once every 3 weeks), two patients had a partial response, two patients had stable disease, and two patients were not evaluable. Two patients had no progressive disease for greater than 20 months. One of the six patients had an increase in BNP, with no cardiac impairment observed on echocardiograms and no evidence of congestive heart failure. As noted above, initial treatment of this cohort predated implementation of the risk mitigation strategy for cohorts 2 and 3.

In the second cohort (OMP-21M18 2.5 mg/kg once every 3 weeks), four patients had a partial response and two patients had stable disease, with the response lasting from 112 to 225 days. Three of six patients had an increase in their BNP levels and two of those patients met the criteria for administration of a cardioprotective ACE inhibitor and/or carvedilol. The third patient only had one sample with a BNP level above 100 pg/ml, and was not treated with an ACE inhibitor and/or carvedilol. There was no cardiac impairment in these patients observed on echocardiograms and no evidence of congestive heart failure.

In the third cohort (OMP-21M18 5 mg/kg once every 3 weeks), two patients had a partial response, four patients had stable disease, one patient had progressive disease due to a new lesion, and one patient was not evaluable (this cohort is ongoing). Four of eight patients had an increase in their BNP levels and three patients were treated with a cardioprotective ACE inhibitor and/or carvedilol. The fourth patient only had one sample with a BNP level at or above 100 pg/ml, and was not treated with an ACE inhibitor and/or carvedilol. There was no cardiac impairment in these patients observed on echocardiograms and no evidence of congestive heart failure. These results are summarized in FIG. 1.

In regard to efficacy as measured by the percentage change in target tumor lesions including cohorts 1, 2 and 3, the response of evaluable patients was: 8/17 (47%) patients had a partial response, 8/17 (47%) patients had stable disease, and 1/17 (6%) patients had progressive disease (FIG. 2).

In regard to safety in cohorts 2 and 3 with risk mitigation, five patients were started on a cardioprotective ACE inhibitor and/or carvedilol. Three of the patients continued treatment with OMP-21M18 and their BNP levels were controlled, while one patient was taken off OMP-21M18 treatment due to an increased BNP level above 400 pg/ml. None of the patients had a decline in LVEF or evidence of congestive heart failure. Other aspects of the safety profile were similar to what has been observed with standard carboplatin/pemetrexed chemotherapy treatment. In addition, in a preliminary analysis of patient samples (n=10), pemetrexed and carboplatin did not appear to influence the pharmacokinetics of OMP-21M18.

Example 3

Phase 1b Study of OMP-21M18 in Combination with Gemcitabine in Subjects with Pancreatic Cancer The study is a Phase 1b dose-escalation study of OMP-21M18 plus gemcitabine in subjects with locally advanced or metastatic pancreatic cancer. Subjects had not received prior chemotherapy for the cancer. The primary objective of the study was to determine the maximum tolerated dose of OMP-21M18 plus gemcitabine in subjects with pancreatic cancer. The secondary objectives were to determine the safety, the rate of immunogenicity, the preliminary efficacy, and the pharmacokinetics of OMP-21M18 in combination with gemcitabine as a first line treatment in subjects with pancreatic.

Gemcitabine (1000 mg/m2) was administered once every week for up to 7 weeks (or until toxicity necessitates reducing or holding a dose), followed by a week of rest from treatment. Subsequent cycles consisted of once weekly infusions for 3 consecutive weeks out of every 4 weeks. OMP-21M18 was supplied at a concentration of 10 mg/ml in a 25-ml single-use glass vial filled to 20 ml to deliver a total of 200 mg per vial. OMP-21M18 was administered by intravenous (IV) infusion over 30 minutes once every 14 days or once every 4 weeks until disease progression.

The first cohort of eight patients was administered OMP-21M18 at a dosage of 2.5 mg/kg once every 2 weeks. Treatment in this cohort was paused due to emerging evidence of cardiotoxicity secondary to administration of OMP-21M18 in other ongoing studies (see Example 1). The protocol was amended to include a risk mitigation plan to enhance the therapeutic index of OMP-21M18 and manage tolerability. The second cohort of eight patients was administered OMP-21M18 at a dosage of 2.5 mg/kg once every 4 weeks and the third cohort of eight patients will be administered OMP-21M18 at a dosage of 5 mg/kg once every 4 weeks. As part of the safety evaluation and risk mitigation, subjects were monitored for B-type natriuretic peptide (BNP) levels in blood samples every 14 days. Patients were administered a cardioprotective ACE inhibitor or carvedilol if their BNP levels were greater than or equal to 100 pg/ml in two consecutive samples or greater than or equal to 200 pg/ml in one sample, while still receiving OMP-21M18. Patients were administered an ACE inhibitor or carvedilol if their BNP level was greater than or equal to 300 pg/ml in any one sample and treatment with OMP-21M18 was withheld. Treatment with OMP-21M18 was restarted when BNP levels decreased below 300 pg/ml. If a subject's BNP level was greater than 400 pg/ml in any one sample, treatment with OMP-21M18 was discontinued. In addition, subjects had Doppler echocardiograms every 28 days to assess cardiac function and monitor left ventricular ejection fraction (LVEF) and peak tricuspid velocity (PTV). Baseline BNP and echocardiogram readings were taken just prior to administration of the first dosage.

During the study, subjects were assessed for adverse events from the time of enrollment through 30 days after the last dose of OMP-21M18. Adverse events were assessed using the National Cancer Institute (NCI) Common Terminology Criteria for Adverse Events (CTCAE), version 4.02.

In the first cohort (OMP-21M18 2.5 mg/kg once every 2 weeks), one patient had a partial response, four patients had stable disease, and three patients were not evaluable. Six of eight patients had no progressive disease for 22 to 147 days, before study was put on hold. Six of the eight patients had an increase in their BNP, with no cardiac impairment observed on echocardiograms and no evidence of congestive heart failure. As noted above, initial treatment of this cohort predated implementation of the risk mitigation strategy for cohorts 2 and 3.

In the second cohort (OMP-21M18 2.5 mg/kg once every 4 weeks), one patient had a partial response, two patients had stable disease, three patients had progressive disease, and two patients were not evaluable. This cohort is ongoing. Four of eight patients had an increase in their BNP levels and one of those patients met the criteria for administration of an ACE inhibitor and/or carvedilol. There was no cardiac impairment in these patients observed on echocardiograms and no evidence of congestive heart failure.

Figure 3:
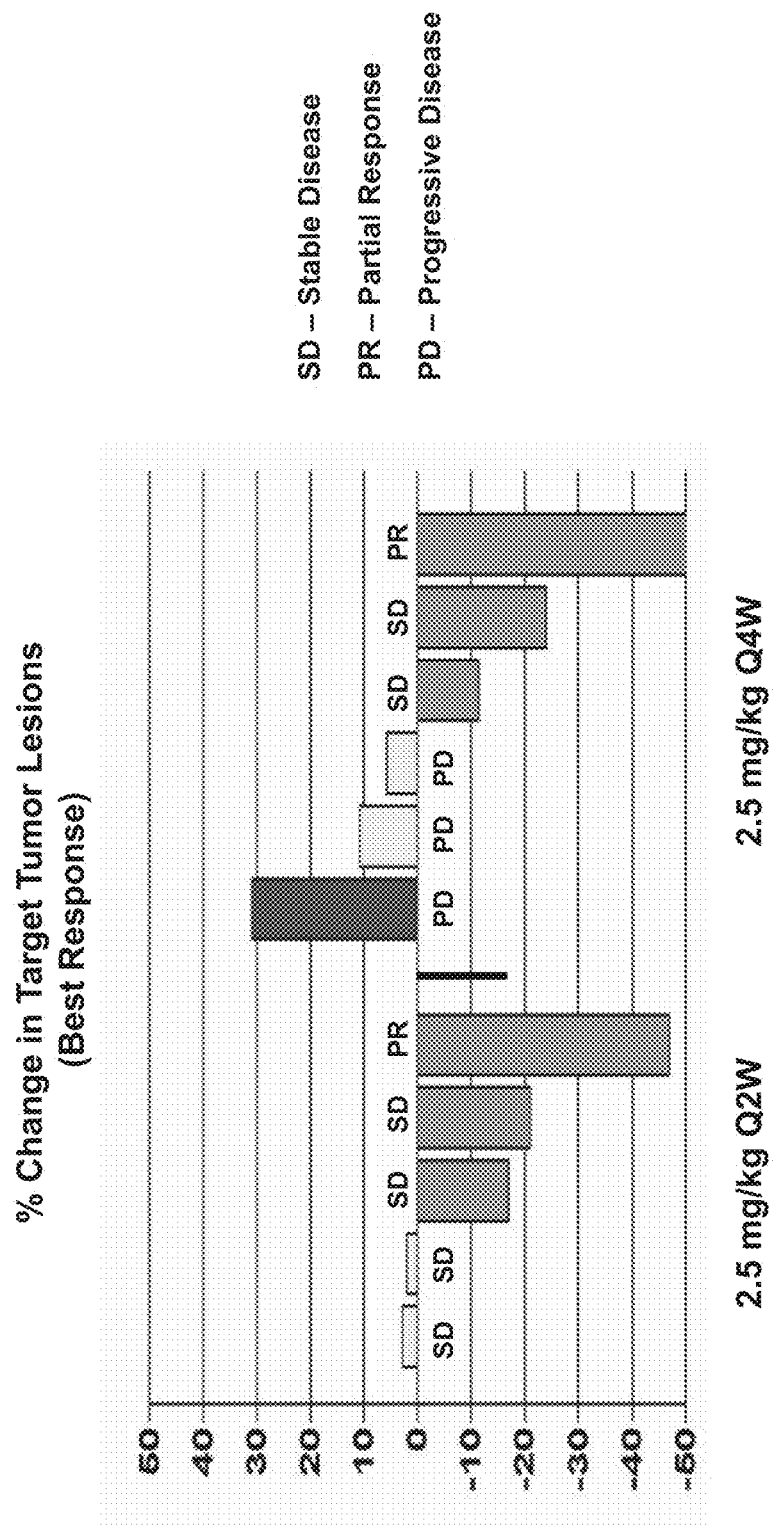
FIG. 3. Percent change in target tumor lesions in subjects enrolled in the Phase 1b clinical trial for treatment of pancreatic cancer with OMP-21M18 in combination with gemcitabine.

In regard to efficacy as measured by the percentage change in target tumor lesions including cohorts 1, and 2, the response for evaluable patients was: 2/11 (18%) patients had a partial response, 6/11 (54%) patients had stable disease, and 3/11 (27%) patients had progressive disease (FIG. 3). In regard to safety in cohort 2 with risk mitigation, 1 patient was started on a cardioprotective ACE inhibitor and/or carvedilol while continuing treatment with OMP-21M18 and their BNP levels were controlled. In all patients, there was no decline seen in LVEF or evidence of congestive heart failure. Other aspects of the safety profile were similar to what has been observed with standard gemcitabine chemotherapy treatment.

It is understood that the examples and embodiments described herein are for illustrative purposes only and that various modifications or changes in light thereof will be suggested to persons skilled in the art and are to be included within the spirit and purview of this application.

All publications, patents, and patent applications cited herein are hereby incorporated by reference in their entirety for all purposes to the same extent as if each individual publication, patent, or patent application were specifically and individually indicated to be so incorporated by reference.

---

SEQUENCES

21M18 Heavy chain CDR1
(SEQ ID NO: 1)
TAYYIH

21M18 - H2 Heavy chain CDR2
(SEQ ID NO: 2)
YISCYNGATNYNQK EKG

SEQUENCES

21M18 - H7 Heavy chain CDR2
(SEQ ID NO: 3)
YISSYNGATNYNQKFKG

21M18 - H9 Heavy chain CDR2
(SEQ ID NO: 4)
YISVYNGATNYNQKFKG

21M18 Heavy chain CDR3
(SEQ ID NO: 5)
RDYDYDVGMDY

21M18 Light chain CDR1
(SEQ ID NO: 6)
RASESVDNYGISFMK

21M18 Light chain CDR2
(SEQ ID NO: 7)
AASNQGS

21M18 Light chain CDR3
(SEQ ID NO: 8)
QQSKEVPWTFGG

21M18 - H2 Heavy chain variable region
(SEQ ID NO: 9)
QVQMPQSGAEVKKPGASVKISCKASGYSFTAYYIHWVKQAPGQGLEWIGY
ISCYNGATNYNQKFKGRVTFTTDTSTSTAYMELRSLRSDDTAVYYCARDY
DYDVGMDYWGQGTLVTVSS 21M18 - H7 Heavy chain variable region
(SEQ ID NO: 10)
QVQLVQSGAEVKKPGASVKISCKASGYSETAYYIHWVKQAPGQGLEWIGY
ISSYNGATNYNQKFKGRVTFTTDTSTSTAYMELRSLRSDDTAVYYCARDY
DYDVGMDYWGQGTLVTVSS 21M18 - H9 Heavy chain variable region
(SEQ ID NO: 11)
QVQMPQSGAEVKKPGASVKISCKASGYSFTAYYIHWVKQAPGQGLEWIGY
ISVYNGATNYNQKFKGRVTFTTDTSTSTAYMELRSLRSDDTAVYYCARDY
DYDVGMDYWGQGTLVTVSS 21M18 Light chain variable region
(SEQ ID NO: 12)
DIVMTQSPDSLAVSLGERATISCRASESVDNYGISFMLWFQQKPGQPPKL
LIYAASNQGSGVPDRFSGSGSGTDFTLTISSLQAEDVAVYYCQQSKEVPW
TFGGGTKVEIK Human DLL4 extracellular domain with putative signal sequence underlined
(SEQ ID NO: 13)
MAAASPSASGWALLLLVALWQQRAAGSGVFQLQLQEFINERGVLASGRPC
EPGCRTFFRVCLKHFQAVVSPGPCTFGTVSTPVLGTNSFAVRDDSSGGGR
LNPLQPFNFTWPGTFSLIIEAWHAPGDDLRPEALPPDALISKIAIQGSLA
VGQNWLLDEQTSTLTRLRYSYRVICSDNYYGDNCSRLCKKRNDHFGHYVC
QPDGNLSCLPGWTGEYCQQPICLSGCHEQNGYCSKPAECLCRPGWQGRLC
HNECIPHNGCRGTCSTPWQCTCDEGWGGLFCDQDLNYCTHHSPCKNGATC
SNSGQRSYTCTCRPGYTGVDCELELSECDSNPCRNGGSCKDQEDGYHCLC
SPPGYYGLHCEHSTLCADSPCFNGGSCRERNQGANYACECPPNFTGSNCE
CKKVDRCTSNPCANGGQLNRGPSRMCRCRPGFTGTYCELHVSDCARNPCA
HGGTCHDLENGLMCTCPAGFSGRRCEVRTSIDACASSPCFNRATCYTDLS
TDTFVCNCPYGFVGSRCEFPVG Human DLL4 N-terminal region with putative signal sequence underlined
(SEQ ID NO: 14)
MAAASRSASGWALLLLVALWQQRAAGSGVEQLQLQEFINERGVLASGRPC
EPGCRTFFRVCLKHFQAVVSPGPCTEGTVSTPVLGTNSFAVRDDSSGGGR
NPLQLPFNETWPGIFSLIIEAWHAPGDDLRPEALPPDALISKIAIQGSLA
VGQN Human DLL4 DST, Region
(SEQ ID NO: 15)
WLLDEQTSTLTRLRYSYRVICSDNYYGDNCSRLCKKRNDHFGHYVCQPDG
NLSCLPGWTGEYC Human DLL4 amino acids 1-217 with putative signal sequence underlined
(SEQ ID NO: 16)
MAAASRSASGWALLLLVALWQQRAAGSGVFQLQLQEFINERGVLASGRPC
EPGCRIFFRVCLKHFQAVVSPGPCTEGTVSTPVLGTNSFAVRDDSSGGGR
NPLQLPENFTWPGTESLIIEAWHAPGDDLRPEALPPDALISKIAIQGSLA
VGQNWLLDEQTSTLTRLRYSYRVICSDNYYGDNCSRLCKKRNDHFGHYVC
QPDGNLSCLPGWTGEYC Human DLL4 amino acids 27-217
(SEQ ID NO: 17)
SGVFQLQLQEFINERGVLASGRPCEPGCRTFFRVCLKHFQAVVSPGPCTF
GTVSTPVLGTNSFAVRDDSSGGGRNPLQLPFNETWPGTFSLIIEAWHAPG
DDLRPEALPPDALISKIAIQGSLAVGQNWLLDEQTSTLTRLRYSYRVICS
DNYYGDNCSRLCKKRNDHFGHYVCQPDGNLSCLPGWTGEYC Human DLL4 amino acids 66-73
(SEQ ID NO: 18)
QAVVSPGP Human DLL4 amino acids 139-146
(SEQ ID NO: 19)
LISKIAIQ

What is claimed is:

1. A method of monitoring and reducing the development of cardiotoxicity related to treatment with a delta-like protein 4 (DLL4) antagonist and unrelated to hypertension, comprising:
   (a) determining the level of a natriuretic peptide in a sample from a human subject who has cancer and has been receiving treatment with the DLL4 antagonist;
   (b) comparing the level of the natriuretic peptide in the sample to a predetermined level of the natriuretic peptide; and
   (c) administering to the subject a therapeutically effective amount of a cardioprotective medication if the level of the natriuretic peptide is above the predetermined level of the natriuretic peptide;
   and wherein the DLL4 antagonist is an antibody that specifically binds human DLL4.

2. The method of claim 1, wherein the natriuretic peptide is B-type natriuretic peptide (BNP).

3. The method of claim 1, wherein the sample is blood, serum, or plasma.

4. The method of claim 1, wherein a sample is obtained approximately every 2 weeks.

5. The method of claim 1, wherein the predetermined level of the natriuretic peptide is:
   (a) the amount of the natriuretic peptide in a sample obtained at an earlier date;
   (b) the amount of the natriuretic peptide in a sample obtained prior to treatment; or
   (c) a normal reference level.

6. The method of claim 5, wherein the normal reference level for the natriuretic peptide is about 100 pg/ml or less in blood, serum, or plasma.

7. The method of claim 1, wherein the predetermined level of the natriuretic peptide is about 100 pg/ml or less, about 150 pg/ml or less, about 200 pg/ml or less, or about 300 pg/ml or less.

8. The method of claim 1, wherein the predetermined level of the natriuretic peptide is about 100 pg/ml or less.

9. The method of claim 1, wherein the cardioprotective medication is an ACE inhibitor and/or a β-blocker.

10. The method of claim 1, wherein the cardioprotective medication is carvedilol.

11. The method of claim 6, wherein the natriuretic peptide is BNP.

12. The method of claim 1, wherein the cancer is selected from the group consisting of: lung cancer, breast cancer, colon cancer, colorectal cancer, melanoma, pancreatic cancer, gastrointestinal cancer, renal cancer, ovarian cancer, liver cancer, endometrial cancer, kidney cancer, prostate cancer, thyroid cancer, neuroblastoma, glioma, glioblastoma multiforme, cervical cancer, stomach cancer, bladder cancer, hepatoma, and head and neck cancer.

13. The method of claim 1, wherein the subject has been receiving treatment with the DLL4 antagonist in combination with one or more additional therapeutic agents.

14. The method of claim 13, wherein the additional therapeutic agent is a chemotherapeutic agent.

15. The method of claim 13, wherein the additional therapeutic agent(s) is:
   (a) carboplatin and pemetrexed;
   (b) gemcitabine;
   (c) gemcitabine and albumin-bound paclitaxel; or
   (d) paclitaxel.

16. The method of claim 1, wherein the cardiotoxicity is left ventricular dysfunction or congestive heart failure.

17. The method of claim 1, further comprising withholding treatment with the DLL4 antagonist if the level of the natriuretic peptide is above the predetermined level of the natriuretic peptide.

18. The method of claim 17, wherein if the level of the natriuretic peptide decreases after administration of the cardioprotective medication, then treatment with the DLL4 antagonist is resumed.

19. The method of 1, wherein the steps (a)-(c) are performed at least every four weeks during treatment with the DLL4 antagonist.

20. A method of monitoring and reducing the development of cardiotoxicity caused by treatment with a delta-like protein 4 (DLL4) antagonist and not caused by hypertension, comprising:
   (a) determining the level of a natriuretic peptide in a sample from a human subject who has cancer and has been receiving treatment with the DLL4 antagonist;
   (b) comparing the level of the natriuretic peptide in the sample to a predetermined level of the natriuretic peptide; and
   (c) administering to the subject a therapeutically effective amount of a cardioprotective medication if the level of the natriuretic peptide is above the predetermined level of the natriuretic peptide;
      wherein the DLL4 antagonist is an antibody that specifically binds human DLL4.

21. The method of 20, wherein the steps (a)-(c) are performed at least every four weeks during treatment with the DLL4 antagonist.

\* \* \* \* \*

SEQUENCE LISTING

```
<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: 21M18 Heavy chain CDR1

<400> SEQUENCE: 1

Thr Ala Tyr Tyr Ile His
1               5

<210> SEQ ID NO 2
<211> LENGTH: 17
<212> TYPE: PRT
<213> ORGANISM: Artificial Sequence
```

```
<220> FEATURE:
<223> OTHER INFORMATION: 21M18 - H2 Heavy chain CDR2

<400> SEQUENCE: 2

Tyr Ile Ser Cys Tyr Asn Gly Ala Thr Asn Tyr Asn Gln Lys Phe Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: 21M18 - H7 Heavy chain CDR2

<400> SEQUENCE: 3

Tyr Ile Ser Ser Tyr Asn Gly Ala Thr Asn Tyr Asn Gln Lys Phe Lys
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: 21M18 - H9 Heavy chain CDR2

<400> SEQUENCE: 4

Tyr Ile Ser Val Tyr Asn Gly Ala Thr Asn Tyr Asn Gln Lys Phe Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: 21M18 Heavy chain CDR3

<400> SEQUENCE: 5

Arg Asp Tyr Asp Tyr Asp Val Gly Met Asp Tyr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: 21M18 Light chain CDR1

<400> SEQUENCE: 6

Arg Ala Ser Glu Ser Val Asp Asn Tyr Gly Ile Ser Phe Met Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: 21M18 Light chain CDR2

<400> SEQUENCE: 7

Ala Ala Ser Asn Gln Gly Ser
1               5
```

```
<210> SEQ ID NO 8
<211> LENGTH: 12
<212> TYPE: PRT
<213> ORGANISM: Artificial Sequence
<220> FEATURE:
<223> OTHER INFORMATION: 21M18 Light chain CDR3

<400> SEQUENCE: 8

Gln Gln Ser Lys Glu Val Pro Trp Thr Phe Gly Gly
1               5                   10

<210> SEQ ID NO 9
<211> LENGTH: 119
<212> TYPE: PRT
<213> ORGANISM: Artificial Sequence
<220> FEATURE:
<223> OTHER INFORMATION: 21M18 - H2 Heavy chain variable

<400> SEQUENCE: 9

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ser Cys Tyr Asn Gly Ala Thr Asn Tyr Asn Gln Lys Phe
        50                  55                  60

Lys Gly Arg Val Thr Phe Thr Thr Asp Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: 21M18 - H7 Heavy chain variable region

<400> SEQUENCE: 10

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ser Ser Tyr Asn Gly Ala Thr Asn Tyr Asn Gln Lys Phe
        50                  55                  60

Lys Gly Arg Val Thr Phe Thr Thr Asp Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
```

```
<210> SEQ ID NO 11
<211> LENGTH: 119
<212> TYPE: PRT
<213> ORGANISM: Artificial Sequence
<220> FEATURE:
<223> OTHER INFORMATION: 21M18 - H9 Heavy chain variable region

<400> SEQUENCE: 11

Gln Val Gln Leu Val Gln Ser Gly Ala Glu Val Lys Lys Pro Gly Ala
 1               5                  10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Val Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 12
<211> LENGTH: 111
<212> TYPE: PRT
<213> ORGANISM: Artificial Sequence
<220> FEATURE:
<223> OTHER INFORMATION: 21M18 Light chain variable region

<400> SEQUENCE: 12

Asp Ile Val Met Thr Gln Ser Pro Asp Ser Leu Ala Val Ser Leu Gly
 1               5                  10                  15

Glu Arg Ala Thr Ile Ser Cys Arg Ala Ser Gly Ser Val Asp Asn Tyr
            20                  25                  30

Gly Ile Ser Phe Met Lys Trp Phe Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys
            100                 105                 110

<210> SEQ ID NO 13
<211> LENGTH: 522
<212> TYPE: PRT
<213> ORGANISM: Homo sapiens

<400> SEQUENCE: 13

Met Ala Ala Ala Ser Arg Ser Ala Ser Gly Trp Ala Leu Leu Leu Leu
 1               5                  10                  15

Val Ala Leu Trp Gln Gln Arg Ala Ala Gly Ser Gly Val Phe Gln Leu
```

```
            20                  25                  30
Gln Leu Gln Glu Phe Ile Asn Glu Arg Gly Val Leu Ala Ser Gly Arg
        35                  40                  45
Pro Cys Glu Pro Gly Cys Arg Thr Phe Phe Arg Val Cys Leu Lys His
 50                  55                  60
Phe Gln Ala Val Val Ser Pro Gly Pro Cys Thr Phe Gly Thr Val Ser
 65                  70                  75                  80
Thr Pro Val Leu Gly Thr Asn Ser Phe Ala Val Arg Asp Asp Ser Ser
                 85                  90                  95
Gly Gly Gly Arg Asn Pro Leu Gln Leu Pro Phe Asn Phe Thr Trp Pro
            100                 105                 110
Gly Thr Phe Ser Leu Ile Ile Glu Ala Trp His Ala Pro Gly Asp Asp
        115                 120                 125
Leu Arg Pro Glu Ala Leu Pro Pro Asp Ala Leu Ile Ser Lys Ile Ala
        130                 135                 140
Ile Gln Gly Ser Leu Ala Val Gly Gln Asn Trp Leu Leu Asp Glu Gln
145                 150                 155                 160
Thr Ser Thr Leu Thr Arg Leu Arg Tyr Ser Tyr Arg Val Ile Cys Ser
                165                 170                 175
Asp Asn Tyr Tyr Gly Asp Asn Cys Ser Arg Leu Cys Lys Lys Arg Asn
            180                 185                 190
Asp His Phe Gly His Tyr Val Cys Gln Pro Asp Gly Asn Leu Ser Cys
        195                 200                 205
Leu Pro Gly Trp Thr Gly Glu Tyr Cys Gln Gln Pro Ile Cys Leu Ser
        210                 215                 220
Gly Cys His Glu Gln Asn Gly Tyr Cys Ser Lys Pro Ala Glu Cys Leu
225                 230                 235                 240
Cys Arg Pro Gly Trp Gln Gly Arg Leu Cys Asn Glu Cys Ile Pro His
                245                 250                 255
Asn Gly Cys Arg His Gly Thr Cys Ser Thr Pro Trp Gln Cys Thr Cys
            260                 265                 270
Asp Glu Gly Trp Gly Gly Leu Phe Cys Asp Gln Asp Leu Asn Tyr Cys
        275                 280                 285
Thr His His Ser Pro Cys Lys Asn Gly Ala Thr Cys Ser Asn Ser Gly
        290                 295                 300
Gln Arg Ser Tyr Thr Cys Thr Cys Arg Pro Gly Tyr Thr Gly Val Asp
305                 310                 315                 320
Cys Glu Leu Glu Leu Ser Glu Cys Asp Ser Asn Pro Cys Arg Asn Gly
                325                 330                 335
Gly Ser Cys Lys Asp Gln Glu Asp Gly Tyr His Cys Leu Cys Pro Pro
            340                 345                 350
Gly Tyr Tyr Gly Leu His Cys Glu His Ser Thr Leu Ser Cys Ala Asp
        355                 360                 365
Ser Pro Cys Phe Asn Gly Gly Ser Cys Arg Glu Arg Asn Gln Gly Ala
        370                 375                 380
Asn Tyr Ala Cys Glu Cys Pro Pro Asn Phe Thr Gly Ser Asn Cys Glu
385                 390                 395                 400
Lys Lys Val Asp Arg Cys Thr Ser Asn Pro Cys Ala Asn Gly Gly Gln
                405                 410                 415
Cys Leu Asn Arg Gly Pro Ser Arg Met Cys Arg Cys Arg Pro Gly Phe
            420                 425                 430
Thr Gly Thr Tyr Cys Glu Leu His Val Ser Asp Cys Ala Arg Asn Pro
        435                 440                 445
```

Cys Ala His Gly Gly Thr Cys His Asp Leu Glu Asn Gly Leu Met Cys
            450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly
            515                 520

<210> SEQ ID NO 14
<211> LENGTH: 154
<212> TYPE: PRT
<213> ORGANISM: Homo sapiens

<400> SEQUENCE: 14

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
130                 135                 140

Ile Gln Gly Ser Leu Ala Val Gly Gln Asn
145                 150

<210> SEQ ID NO 15
<211> LENGTH: 63
<212> TYPE: PRT
<213> ORGANISM: Homo sapiens

<400> SEQUENCE: 15

Trp Leu Leu Asp Glu Gln Thr Ser Thr Leu Thr Arg Leu Arg Tyr Ser
1               5                   10                  15

Tyr Arg Val Ile Cys Ser Asp Asn Tyr Tyr Gly Asp Asn Cys Ser Arg
            20                  25                  30

Leu Cys Lys Lys Arg Asn Asp His Phe Gly His Tyr Val Cys Gln Pro
        35                  40                  45

Asp Gly Asn Leu Ser Cys Leu Pro Gly Trp Thr Gly Glu Tyr Cys
50                  55                  60

<210> SEQ ID NO 16
<211> LENGTH: 217
<212> TYPE: PRT
<213> ORGANISM: Homo sapiens

<400> SEQUENCE: 16

```
Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys
    210                 215
```

<210> SEQ ID NO 17
<211> LENGTH: 191
<212> TYPE: PRT
<213> ORGANISM: Homo sapiens

<400> SEQUENCE: 17

```
Ser Gly Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
    130                 135                 140
```

```
Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys
            180                 185                 190

<210> SEQ ID NO 18
<211> LENGTH: 8
<212> TYPE: PRT
<213> ORGANISM: Homo sapiens

<400> SEQUENCE: 18

Gln Ala Val Val Ser Pro Gly Pro
1               5

<210> SEQ ID NO 19
<211> LENGTH: 8
<212> TYPE: PRT
<213> ORGANISM: Homo sapiens

<400> SEQUENCE: 19

Leu Ile Ser Lys Ile Ala Ile Gln
1               5
```